(12) United States Patent
Leventer et al.

(10) Patent No.: US 11,723,890 B2
(45) Date of Patent: *Aug. 15, 2023

(54) METHODS OF TREATMENT USING AN MTORC1 MODULATOR

(71) Applicant: Navitor Pharmaceuticals, Inc., Cambridge, MA (US)

(72) Inventors: Steven Leventer, Cambridge, MA (US); Steven D. Targum, Cambridge, MA (US)

(73) Assignee: Navitor Pharmaceuticals, Inc., Boston, MA (US)

(*) Notice: Subject to any disclaimer, the term of this patent is extended or adjusted under 35 U.S.C. 154(b) by 112 days.

This patent is subject to a terminal disclaimer.

(21) Appl. No.: 17/086,639

(22) Filed: Nov. 2, 2020

(65) Prior Publication Data

US 2021/0169835 A1  Jun. 10, 2021

Related U.S. Application Data

(60) Provisional application No. 62/929,449, filed on Nov. 1, 2019.

(51) Int. Cl.
*A61K 31/198* (2006.01)
*A61P 25/24* (2006.01)
*A61K 9/00* (2006.01)

(52) U.S. Cl.
CPC .......... *A61K 31/198* (2013.01); *A61K 9/0053* (2013.01); *A61P 25/24* (2018.01)

(58) Field of Classification Search
CPC .................................................. A61K 31/198
See application file for complete search history.

(56) References Cited

U.S. PATENT DOCUMENTS

| | | | |
|---|---|---|---|
| 4,346,110 A | 8/1982 | Palfreyman et al. | |
| 5,639,600 A | 6/1997 | McGrath et al. | |
| 6,458,781 B1 | 10/2002 | Connor et al. | |
| 6,613,934 B1 | 9/2003 | Jegelka et al. | |
| 7,087,648 B1 | 8/2006 | McGrath | |
| 7,390,799 B2 | 6/2008 | Bruncko et al. | |
| 8,138,347 B2 | 3/2012 | Knight et al. | |
| 10,100,066 B2 * | 10/2018 | Fetalvero | C07C 229/14 |
| 10,414,782 B2 * | 9/2019 | Fetalvero | C07C 233/07 |
| 10,752,644 B2 * | 8/2020 | Fetalvero | C07C 311/14 |
| 10,912,750 B2 * | 2/2021 | Saiah | A61K 31/198 |
| 11,325,924 B2 | 5/2022 | Fetalvero et al. | |
| 11,354,654 B2 | 5/2022 | Lenzini | |
| 2003/0203900 A1 | 10/2003 | Quibell | |
| 2004/0110982 A1 | 6/2004 | Anderson et al. | |
| 2007/0082894 A1 | 4/2007 | Burns et al. | |
| 2010/0093706 A1 | 4/2010 | Hauske | |
| 2010/0240663 A1 | 9/2010 | Christos et al. | |
| 2012/0219596 A1 | 8/2012 | Limbach et al. | |
| 2012/0225859 A1 | 9/2012 | Burger et al. | |
| 2012/0231993 A1 | 9/2012 | Gazic Smilovic et al. | |
| 2013/0116430 A1 | 5/2013 | Fujiwara et al. | |
| 2013/0296245 A1 | 11/2013 | Li et al. | |
| 2014/0186453 A1 | 7/2014 | Zale et al. | |
| 2015/0105386 A1 | 4/2015 | Mack et al. | |
| 2016/0137606 A1 | 5/2016 | Bissantz et al. | |
| 2017/0114080 A1 | 4/2017 | Fetalvero et al. | |
| 2017/0369435 A1 | 12/2017 | Pourgholami et al. | |
| 2018/0333381 A1 | 11/2018 | Salah et al. | |
| 2019/0240174 A1 | 8/2019 | During | |
| 2020/0079800 A1 | 3/2020 | Fetalvero et al. | |
| 2020/0131114 A1 | 4/2020 | Lenzini | |
| 2021/0047347 A1 | 2/2021 | Fetalvero et al. | |
| 2021/0228523 A1 | 7/2021 | Saiah et al. | |
| 2022/0340604 A1 | 10/2022 | Fetalvero et al. | |
| 2022/0371985 A1 | 11/2022 | Lenzini | |

FOREIGN PATENT DOCUMENTS

| | | |
|---|---|---|
| EP | 0372816 A1 | 6/1990 |
| EP | 1389617 A1 | 2/2004 |
| EP | 2154139 A1 | 2/2010 |
| WO | WO-1998008853 A1 | 3/1998 |
| WO | 2000026259 A1 | 5/2000 |
| WO | WO-2003063794 A2 | 8/2003 |
| WO | WO-2004019973 A1 | 3/2004 |
| WO | WO-2004089925 A1 | 10/2004 |
| WO | WO-2004106328 A1 | 12/2004 |
| WO | WO-2005007623 A2 | 1/2005 |
| WO | WO-2005113554 A2 | 12/2005 |
| WO | WO-2006078846 A1 | 7/2006 |
| WO | WO-2006117696 A2 | 11/2006 |
| WO | WO-2006122806 A2 | 11/2006 |
| WO | WO-2007016176 A2 | 2/2007 |
| WO | WO-2007044729 A2 | 4/2007 |
| WO | WO-2007053452 A1 | 5/2007 |

(Continued)

OTHER PUBLICATIONS

Abe et al., "Mammalian target of Rapamycin (mTOR) Activation Increases Axonal Growth Capacity of Injured Peripheral Nerves," The Journal of Biological Chemistry, vol. 285, No. 36, Sep. 3, 2010 (pp. 28034-28043).

Ali et al., "IL-15-PI3K-AKT-mTOR: A Critical Pathway in the Life Journey of Natural Killer Cells," Frontiers in Immunology, vol. 6, No. 355, Jul. 20, 2015 (9 pages).

Andrzejewska et al., "Cystinosin is a Component of the Vacuolar H+-ATPase-Ragulator-Rag Complex Controlling Mammalian Target of Rapamycin Complex 1 Signaling," Journal of the American Society of Nephrology, vol. 27, No. 6, Jun. 2016 (pp. 1678-1688).

Bar-Peled et al., "Regulation of mTORC1 by amino acids", Trends in Cell Biology, Jul. 2014, vol. 24, No. 7, pp. 400-406.

(Continued)

Primary Examiner — Rei Tsang Shiao

(74) Attorney, Agent, or Firm — Dechert LLP; Andrea L. C. Reid; Todd K. Macklin

(57) ABSTRACT

The present invention relates to methods, compositions, and unit dosage forms useful for selectively modulating mTORC1 activity.

18 Claims, 13 Drawing Sheets

(56) References Cited

FOREIGN PATENT DOCUMENTS

| | | |
|---|---|---|
| WO | WO-2007070514 A1 | 6/2007 |
| WO | WO-2007084786 A1 | 7/2007 |
| WO | WO-2007129161 A2 | 11/2007 |
| WO | 2008044691 A1 | 4/2008 |
| WO | WO-2008039218 A2 | 4/2008 |
| WO | WO-2008109943 A1 | 9/2008 |
| WO | WO-2008118802 A1 | 10/2008 |
| WO | WO-2009114512 A1 | 9/2009 |
| WO | 2011102964 A1 | 8/2011 |
| WO | WO-2013142229 A1 | 9/2013 |
| WO | WO-2014127052 A1 | 8/2014 |
| WO | WO-2014201111 A1 | 12/2014 |
| WO | WO-2017070518 A1 | 4/2017 |
| WO | WO-2017083823 A1 | 5/2017 |
| WO | WO-2018200625 A1 | 11/2018 |
| WO | WO-2020086816 A1 | 4/2020 |

OTHER PUBLICATIONS

Bar-Peled et al., "A Tumor suppressor complex with GAP activity for the RAG GTPases that signal amino acid sufficiency to mTORC1," Science, vol. 340, No. 6136, May 2013 (1100-1106).
Bar-Peled et al., "An expanded Ragulator is a GEF forthe rag GTPases that signal amino acid levels to mTORC1," Cell, vol. 150, No. 6, Sep. 2012 (pp. 1196-1208).
Berge et al., "Pharmaceutical Salts," Journal of Pharmaceutical Sciences, vol. 66, Jan. 1977 (pp. 1-19).
Bidinosti et al., "CLK2 inhibition ameliorates autistic features associated with SHANK3 deficiency," Science, vol. 351, No. 6278, Mar. 2016 (pp. 1199-1203).
Bowling et al., "Antipsychotics Activate mTORC1-Dependent Translation to Enhance Neuronal Morphological Complexity," Science Signaling vol. 7, No. 308, Jan. 2014 (31 pages).
Brugarolas et al., "Regulation of mTOR function in response to hypoxia by REDD1 and the TSC1/TSC2 tumor suppressor complex," Genes & Development, vol. 18. Nov. 2004 (pp. 2893-2904).
Buckbinder et al., "Gene regulation by temperature-sensitive p53 mutants: identification of p53 response genes," Proceedings of the National Academy of Sciences of the United States of America, vol. 91, No. 22, Oct. 1994 (pp. 10640-10644).
Budanov et al., "The p53 target genes sestrin1 and sestrin2 connect genotoxic stress and mTOR signaling," Cell, vol. 134, No. 3, Aug. 2008 (pp. 451-460).
Buerger et al., "Localization of Rheb to the endomembrane is critical for its signaling function," Biochemical and Biophysical Research Communications, vol. 344, No. 3, Jun. 2006 (pp. 869-880).
Bull et al, "Conjugate additions of organocuprates to a 3-methylene-6-isopropyldiketopiperazine acceptor for the asymmetric synthesis of homochiral a-amino acids", J. Chem. Soc, Perkins Trans. 1, 2001, 3281-3287.
Bures et al, "Chiral imidazole derivatives synthesis from enentiopure N-protected a-amino acids", Asymmetry 16, Jan. 2005, pp. 1347-1354.
Cao et al., "Autophagy Is Disrupted in a Knock-in Mouse Model of Juvenile Neuronal Ceroid Lipofuscinosis," Journal of Biological Chemistry, vol. 281, No. 29, Jul. 2006 (pp. 20483-20493).
Cao et al., "Translational control of entrainment and synchrony of the suprachiasmatic circadian clock by mTOR/4E-BP1 signaling," Neuron, vol. 79, No. 4, Aug. 2013 (pp. 712-724).
CAS STN Abstract, RN 1555441-22-9 (Pub. Feb. 25, 2014).
CAS STN Abstract, RN 1698493-03-6 (Pub. May 5, 2015).
CAS STN Abstract, RN 1779709-85-1 (Pub. Jun. 14, 2015).
CAS STN Abstract, RN 1780718-09-3 (Pub. Jun. 15, 2015).
Chantranupong et al., "The Sestrins interact with GATOR2 to negatively regulate the amino-acid-sensing pathway upstream of mTORC1," Cell Reports, vol. 9, No. 1, Oct. 2014 (pp. 1-8).
Chauhan et al., "Muscle-specific regulation of the mTOR signaling pathway in MuSK antibody seropositive (MuSK+) experimental autoimmune Myasthenia gravis (EAMG)," Neuroscience Research, vol. 77, No. 1-2, Sep.-Oct. 2013 (pp. 102-109).
Chen et al., "Design, Synthesis, Activity, and Structuire of a Novel Class of Matrix Metalloproteinase Inhibitors containing a Heterocyclic P2-P3 Amide Bond Isotere", Bioorganic & Medicinal Chemistry Letters, 1996, vol. 6, No. 13, pp. 1601-1606.
Chi, "Regulation and function of mTOR signaling in T cell fate decisions," National Reviews Immunology, vol. 12, No. 5, Apr. 2012 (pp. 325-338).
Child et al., "Cardiac mTORC1 Dysregulation Impacts Stress Adaptation and Survival in Huntington's Disease," Cell Rep. 2018;23(4):1020-1033.
Ching et al., "mTOR dysfunction contributes to vacuolar pathology and weakness in valosin-containing protein associated inclusion body myopathy," Human Molecular Genetics, vol. 22, No. 6, Mar. 2013 (pp. 1167-1179).
Cuthbertson et al., "Anabolic signaling deficits underlie amino acid resistance of wasting, aging muscle," FASEB Journal, vol. 19, No. 3, Mar. 2005 (pp. 422-424).
Deboves et al., "A new route to hydrophobic amino acids using copper-promoted reactions of serine-derived organozinc reagents", J. Chem. Soc., Perkins Tran. 1, 2000, pp. 4284-4292.
Delgoffe et al., "The mTOR kinase differentially regulates effector and regulatory T cell lineage commitment," Immunity, vol. 30, No. 6, Jun. 2009 (pp. 832-844).
Di Polo, "Dendrite pathology and neurodegeneration: focus on mTOR," Neural Regeneration Research, vol. 10, No. 4, Apr. 2015 (pp. 559-561).
Dibble et al., "TBC1D7 is a third subunit of the TSC1-TSC2 complex upstream of mTORC1m" Molecular Cell, vol. 47, No. 4, Aug. 2012 (pp. 535-546).
Efeyan et al., "Amino acids and mTORC1: from lysosomes to disease," Trends in Molecular Medicine, vol. 18, No. 9, Sep. 2012 (pp. 524-533).
Fossale et al., "Membrane trafficking and mitochondrial abnormalities precede subunit c deposition in a cerebellar cell model of juvenile neuronal ceroid lipofuscinosis," BMC Neurosci. 2004;5(1):57.
Garami et al., "Insulin Activation of Rheb, a Mediator of mTOR/S6K/4E-BP Signaling, Is Inhibited by TSC1 and 2," Molecular cell, vol. 11, Jun. 2003 (pp. 1457-1466).
Gordon et al., "Regulation of muscle protein synthesis and the effects of catabolic states," International Journal of Biochemistry and Cell Biology, vol. 45, No. 10, Oct. 2013 (pp. 2147-2157).
Gurpur et al., "Valproic acid activates the PI3K/Akt/mTOR pathway in muscle and ameliorates pathology in a mouse model of Duchenne muscular dystrophy," The American Journal of Pathology, vol. 174, No. 3, Mar. 2009 (pp. 999-1008).
Ham et al., "Leucine as a treatment for muscle wasting: A critical review," Clinical Nutrition, vol. 33, No. 6, Dec. 2014 (pp. 937-945).
Hirose et al., "RagA is a functional homologue of S. cerevisiae Gtr1p involved in the Ran/Gsp1-GTPase pathway," Journal of Cell Science, vol. 111, Pt. 1, Jan. 1998 (pp. 11-21).
Howell et al., "A growing role for mTOR in promoting anabolic metabolism," Biochemical Society Transactions, vol. 41, No. 4, Jul. 2013 (pp. 906-912).
Ignácio et al., "New perspectives on the involvement of mTOR in depression as well as in the action of antidepressant drugs," British Journal of Clinical Pharmacology, vol. 82, No. 5, Nov. 2015 (pp. 1280-1290).
Inoki et al., "Rheb GTPase is a direct target of TSC2 GAP activity and regulates mTOR signaling," Genes & Development, vol. 17, No. 15, Aug. 2003 (pp. 1829-1834).
International Search Report and Written Opinion issued by the United States Patent and Trademark Office as International Searching Authority for International Application No. PCT/US2018/029288, dated Jul. 6, 2018 (13 pages).
Ito et al., "A medium-term rat liver bioassay for rapid in vivo detection of carcinogenic potential of chemicals," Cancer Science, vol. 94, No. 1, Jan. 2003 (pp. 3-8).
Ivanova et al., "Altered mTOR signalling in nephropathic cystinosis," Journal of Inherited Metabolic Disease, vol. 39, No. 3, May 2016 (pp. 457-464).

(56) References Cited

OTHER PUBLICATIONS

Kang et al., "mTORC1 phosphorylation sites encode their sensitivity to starvation and rapamycin," Science, vol. 341, No. 6144, Jul. 2013 (16 pages).
Katholnig et al., "Immune responses of macrophages and dendritic cells regulated by mTOR signaling," Biochemical Society Transactions, vol. 41, No. 4, Aug. 2013 (pp. 927-933).
Kim et al., "mTOR: a pharmacologic target for autophagy regulation," The Journal of Clinical Investigation, vol. 125, No. 1, Jan. 2015 (pp. 25-32).
Kim et al., "Nutrient Regulation of the mTOR Complex 1 Signaling Pathway," Molecules and Cells, vol. 35, No. 6, Jun. 2013 (pp. 463-473).
Kim et al., "Regulation of TORC1 by Rag GTPases in nutrient response," Nature, Cell Biology, vol. 10, No. 8, Jul. 2008 (pp. 935-945).
Kye et al., "SMN regulates axonal local translation via miR-183/mTOR pathway," Human Molecular Genetics, vol. 23, No. 23, Dec. 2014 (pp. 6318-6331).
Köhler et al., "Inflammation in Depression and the Potential for Anti-Inflammatory Treatment," Current Neuropharmacol. 2016;14(7):732-742.
Lambe et al., "Hypocretin (Orexin) Induces Calcium Transients in Single Spines Postsynaptic to Identified Thalamocortical Boutons in Prefrontal Slice," Neuron, vol. 40, No. 1, Sep. 2003 (pp. 139-150).
Laplante et al., "mTOR signaling in growth control and disease," Cell, vol. 149, No. 2, Apr. 2012 (pp. 274-293).
Lee et al., "Functional effects of a pathogenic mutation in Cereblon (CRBN) on the regulation of protein synthesis via the AMPK-mTOR cascade," J. Biol. Chem. 2014;289(34):23343-23352.
Lee et al., "Platelets Support Extracellular Sialylation by Supplying the Sugar Donor Substrate," Journal of Biological Chemistry, vol. 289, No. 13, Mar. 2014 (pp. 8742-8748).
Lee et al., "reinstating aberrant mTORC1 activity in Huntington's disease mice improves disease phenotypes," Neuron, vol. 85, No. 2, Jan. 2015 (pp. 303-315).
Leger et al., "Atrogin-1, MuRF1, and FoXO, as well as phosphorylated GSK-3beta and 4E-BP1 are reduced in skeletal muscle of chronic spinal cord-injured patients," Muscle Nerve, vol. 40, No. 1, Jul. 2009 (pp. 69-78).
Li et al., "Glutamate N-methyl-D-aspartate receptor antagonists rapidly reverse behavioral and synaptic deficits caused by chronic stress exposure," Biological Psychiatry, vol. 69, No. 8, Apr. 2011 (pp. 754-761).
Li et al., "mTOR-dependent synapse formation underlies the rapid antidepressant effects of NMDA antagonists," Science, vol. 329, No. 5994, Aug. 2010 (pp. 959-964).
Liebau et al., "Dysregulated Autophagy Contributes to Podocyte Damage in Fabry's Disease," PLoS One, vol. 8, No. 5, May 2013 (10 pages).
Lin et al., "Activation of mTOR Ameliorates Fragile X Premutation rCGG Repeat-Mediated Neurodegeneration," PLOS One, vol. 8, No. 4, e62572, Apr. 2013 (pp. 1-8).
Liu et al., "GLYX-13 Produces Rapid Antidepressant Responses with Key Synaptic and Behavioral Effects Distinct from Ketamine," Neuropharmacology, vol. 42, No. 6, May 2017 (pp. 1231-1242).
Liu et al., "Hypocretins (Orexins) Regulate Serotonin Neurons in the Dorsal Raphe Nucleus by Excitatory Direct and Inhibitory Indirect Actions," Journal of Neuroscience, vol. 22, No. 21, Nov. 2002 (pp. 9453-9464).
Long et al., "Rheb Binds and Regulates the mTOR Kinase," Current Biology, vol. 15, No. 8, Apr. 2005 (pp. 702-713).
Love, "Demyelinating diseases," The Journal of Clinical Pathology, vol. 59, No. 11, Nov. 2006 (pp. 1151-1159).
Macovei et al, "Polyclonal antibodies: a cheap and efficient tool for screening of enantioselective catalysts", Chem. Dommun, 2012, vol. 48, pp. 4411-4413.
Malkesman et al., "The female urine sniffing test: a novel approach for assessing reward-seeking behavior in rodents," Biological Psychiatry, vol. 67, No. 9, May 2010 (pp. 864-871).

Manzi and Wasko, "Inflammation-mediated rheumatic diseases and atherosclerosis," Annals of the Rheumatic Diseases, vol. 59, No. 5, May 2000 (pp. 321-325).
McVey et al., "CHO cells knocked out for TSC2 display an improved productivity of antibodies underfed batch conditions," Biotechnology and Bioengineering, vol. 113, No. 9, Sep. 2016 (pp. 1942-1952).
Nakamura et al., "Role of the mTOR complex 1 pathway in the in vivo maintenance of the intestinal mucosa by oral intake of amino acids," Geriatric & Gerontology International, vol. 12, No. 1, Jan. 2012 (pp. 131-139).
Napolitano et al., "Impairment of chaperone-mediated autophagy leads to selective lysosomal degradation defects in the lysosomal storage disease cystinosis," EMBO Molecular Medicine, vol. 7, No. 2, Feb. 2015 (pp. 158-174).
Nelson et al., "Autophagy-lysosome pathway associated neuropathology and axonal degeneration in the brains of alpha-galactosidase A-deficient mice," Acta Neuropathologica Communications, vol. 2, No. 20, Feb. 2014 (pp. 1-15).
Zoncu et al., "mTORC1 senses lysosomal amino acids through an inside-out mechanism that requires the vacuolar H(+)-ATPase," Science, vol. 344, No. 6056, Nov. 2011 (pp. 678-683).
No Author, "substance Record for SID 219681321," PubChem, NIH U.S. National Library of Medicine, National Center for Biotechnology Information, retrieved only at <https://pubchem.ncbi.nlm.nih.gov/substance/219681321#section=Top> accessed Nov. 22, 2016 (6 pages).
No Author, "Substance Record for SID 4757389," PubChem, NIH U.S. National Library of Medicine, National Center for Biotechnology Information, retrieved only at <https://pubchem.ncbi.nlm.nih.gov/substance/4757389#section=Top> accessed Feb. 16, 2017 (5 pages).
No Author, "Substance Record for SID 8685219," PubChem, NIH U.S. National Library of Medicine, National Center for Biotechnology Information, retrieved only at <https://pubchem.ncbi.nlm.nih.gov/substance/8685219/version/1> accessed Nov. 22, 2016, (7 pages).
Nobukuni et al., "Amino acids mediate mTOR/raptor signaling through activation of class 3 phosphatidylinositol 3OH-kinase," Proceedings of the National Academy of Sciences of the United States of America, vol. 102, No. 40, Oct. 2005 (pp. 14238-14243).
Norrmen et al., "mTORC1 controls PNS myelination along the mTORC1-RXR-SREBP-lipid biosynthesis axis in Schwann cells," Cell Reports, vol. 9, No. 2, Oct. 2014 (pp. 646-660).
Novarino et al., "Mutation in BCKD-kinase Lead to a Potentially Treatable Form of Autism with Epilepsy," Science, vol. 338, No. 6105, Sep. 2012 (pp. 394-397).
O'Brien et al., "Regulation of T-cell survival and mitochondrial homeostasis by TSC1," European Journal of immunology, vol. 41, No. 11, Nov. 2011 (pp. 3361-3370).
Panchaud et al., "Amino Acid Deprivation Inhibits TORC1 Through a GTPase-Activating Protein Complex for the Rag Family GTPase Gtr1," Science Signaling, vol. 6, No. 277, May 2013 (p. ra42).
Park et al., "TSC1 regulates the balance between effector and regulatory T cells," The Journal of Clinical Investigation, vol. 123, No. 12, Dec. 2013 (pp. 5165-5178).
Pasiakos et al., "Leucine-enriched essential amino acid supplementation during moderate steady state exercise enhances postexercise muscle protein synthesis," The American Journal Clinical Nutrition, vol. 94, No. 3, Sep. 2011 (pp. 809-818).
Payne et al., "L-Leucine improves the anemia and developmental defects associates with Diamond-Blackfan anemia and del(5q) MDS by activating the mTOR pathway," Blood, vol. 120, No. 11, Sep. 2012 (pp. 2214-2224).
PCT International Search Report and Written Opinion from PCT/US2019/057815 dated Jan. 6, 2020.
PCT International Search Report and Written Opinion from PCT/US2020/058475 dated Feb. 1, 2021.
Pearce et al., "Action of BTN1, the yeast orthologue of the gene mutated in Batten disease," Nature, Genetics, vol. 22, No. 1, May 1999 (pp. 55-58).

(56) References Cited

OTHER PUBLICATIONS

Pedroso et al., "Reviewing the Effects of L-Leucine Supplementation in the Regulation of Food Intake, energy Balance, and Glucose Homeostasis," Nutrients, vol. 7, No. 5, May 2015 (pp. 3914-3937).
Peeters et al., "PA26 is a candidate gene for heterotaxia in humans: identification of a novel PA26-related gene family in human and mouse," Human Genetics, vol. 112, No. 5-6, Feb. 2003 (pp. 573-580).
Peng et al., "Sestrins function as guanine nucleotide dissociation inhibitors for Rag GTPases to control mTORC1 signaling," vol. 159, No. 1, Sep. 2014 (pp. 122-133).
Pollizzi et al., "mTORC1 and mTORC2 selectively regulate CD8+ T cell differentiation," The Journal of Clinical Investigation, vol. 125, No. 5, May 2015 (pp. 2090-2108).
Punzo et al., "Stimulation of the insulin/,TOR pathway delays cone death in a mouse model of retinitis pigmentosa," Nature Neuroscience, vol. 12, No. 1, Jan. 2009 (pp. 44-52).
Rennie, "Anabolic resistance: the effects of aging, sexual dimorphism, and immobilization on human muscle protein turnover," Applied Physiology, Nutrition, and Metabolism, vol. 34, No. 3, Jun. 2009 (pp. 377-381).
Roccio et al., "Regulation of the small GTPase Rheb by amino acids," Oncogene, vol. 25, No. 5. Feb. 2006 (pp. 657-664).
Saito et al., "Novel Role of the Small GTPase Rheb: Its Implication in Endocytic Pathway Independent of the Activation of Mammalian Target of Rapamycin," Journal of Biochemistry, vol. 137, No. 3, Mar. 2005 (pp. 423-430).
Sancak et al., "Ragulator-Rag complex targets mTORC1 to the lysosomal surface and is necessary for its activation by amino acids," Cell, vol. 141, No. 2, Apr. 2010 (pp. 290-303).
Sancak et al., "The Rag GTPases bind raptor and mediate amino acid signaling to mTORC1," Science, vol. 320, No. 5882, Jun. 2008 (pp. 1496-1501).
Saucedo et al., "Rheb promotes cell growth as a component of the insulin/TOR signalling network," Nature, Cell Biology, vol. 5, No. 6, Jun. 2003 (pp. 566-571).
Schürmann et al., "Cloning of a Novel Family of Mammalian GTP-binding Proteins (RagA, RagBs, RagB1) with Remote Similarity to the Ras-related GTPases ," Journal of Biological Chemistry, vol. 270, No. 48, Dec. 1995 (pp. 28982-28988).
Sekiguchi et al., "Novel G Proteins, Rag C and Rag D, Interact with GTP-binding Proteins, Rag A and Rag B," Journal of Biological Chemistry, vol. 276, No. 10, Mar. 2001 (pp. 7246-7257).
Smith et al., "The Tuberous Sclerosis Protein TSC2 Is Not Required forthe Regulation of the Mammalian Target of Rapamycin by Amino Acids and Certain Cellular Stresses," Journal of Biological Chemistry, vol. 280, No. 19, May 2005 (pp. 18717-18727).
Song et al., "A simple method for preparation of N-mono- and N,N-di-alkylated a-amino acids", Tetrahedron Letters, vol. 41, 2000, pp. 8225-8230.
Song et al., "mTOR Attenuates the Inflammatory Response in Cardiomyocytes and Prevents Cardiac Dysfunction in Pathological Hypertrophy," The American Journal of Physiology Cell Physiology, vol. 299, No. 6, Sep. 2010 (pp. C1256-C1266).
Stein et al., "Protein kinetics during and after long-duration spaceflight on MIR," The American Journal of Physiology Endocrinology Metabolism, vol. 276, No. 6 Part 1, Jun. 1999 (pp. E1014-E1021).
Stocker et al., "Rheb is an essential regulator of S6K in controlling cell growth in *Drosophila*," Nature, Cell Biology, vol. 5, No. 6, Jun. 2003 (pp. 559-565).
Takikita et al., "Pertubed myelination process of premyelinating oligodendrocyte in Niemann-Pick type C mouse," The Journal Neuropathology and Experimental Neurology, vol. 63, No. 6, Jun. 2004 (pp. 660-673).

Tarlungeanu et al., "Impaired Amino Acid Transport at the Blood Brain Barrier Is a Cause of Autism Spectrum Disorder," Cell. 2016;167(6):1481-1494.
Tee et al., "Tuberous sclerosis complex-1 and -2 gene products function together to inhibit mammalian target of rapamycin (mTOR)-mediated downstream signaling," Proceedings of the National Academy of Sciences of the United States of America, vol. 99, No. 21, Oct. 2002 (pp. 13571-13576).
Tsun et al., "The folliculin tumor suppressor is a GAP for the RagC/D GTPases that signal amino acid levels to mTORC1," Molecular Cell, vol. 52, No. 4, Nov. 2013 (pp. 495-505).
Tyler et al., "Activation of the mammalian target of rapamycin (mTOR) is essential for oligodendrocyte differentiation," The Journal of Neuroscience, vol. 29, No. 19, May 13, 2009 (pp. 6367-6378).
Vergarajauregui et al., "Autophagic dysfunction in mucolipidosis type IV patients," Human Molecular Genetics, vol. 17, No. 17, Sep. 2008 (pp. 2723-2737).
Wang et al., "Lysosomal amino acid transporter SLC38A9 signals arginine sufficiency to mTORC1," Science, vol. 347, No. 6218, Jan. 2015 (pp. 188-194).
Wang et al., "The amino acid transporter SLC38A9 is a key component of a lysosomal membrane complex that signals arginine sufficiency to mTORC1," Science, vol. 347, No. 6218, Jan. 2015 (pp. 188-194).
Wang et al., "Tuberous sclerosis 1 (Tsc1)-dependent metabolic checkpoint controls development of dendritic cells," Proceedings of the National Academy of Science U.S.A., vol. 110, No. 50, Dec. 2013 (pp. E4894-E4903).
Warner-Schmidt and Duman, "VEGF is an essential mediator of the neurogenic and behavioral actions of antidepressants," Proceedings of the National Academy of Sciences of the United States of America, vol. 104, No. 11, Mar. 2007 (pp. 4647-4652).
Wolfson et al., "Sestrin2 is a leucine sensor for the mTORC1 pathway," Science, vol. 351, No. 6268, Jan. 2016 (pp. 43-48).
Wong et al., "*Drosophila* TRPML is Required for TORC1 Activation," Current Biology, vol. 22, No. 17, Sep. 2012 (pp. 1616-1621).
Xu et al., "A Mental Retardation-linked Nonsense Mutation in Cereblon Is Rescued by Proteasome Inhibition," Journal of Biological Chemistry, vol. 288, No. 41, Oct. 2013 (pp. 29573-29585).
Xu et al., "Improved transcription and translation with L-leucine stimulation of mTORC1 in Roberts syndrome," BMC Genomics, vol. 17, No. 25, No Month Listed 2016 (18 pages).
Yang et al., "Reduced Excitatory Neurotransmission and Mild Autism-Relevant Phenotypes in Adolescent Shank3 Null Mutant Mice," Journal of Neuroscience, vol. 32, No. 19, May 2012 (pp. 6525-6541).
Yang et al., "The tumor suppressor Tsc1 enforces quiescence of naive T cells to promote immune homeostasis and function," Nature Immunology, vol. 12, No. 9, Jul. 2011 (pp. 888-897).
Ye et al., "Chemical aminoacylation of tRNAs with fluorinated amino acids for in vitro protein mutagenesis", Bellstein Journal of Organic Chemistry, 2010, vol. 6, No. 40, pp. 1-6.
CAS STN Abstract, RN 1378266-29-5 (Pub. Jun. 14, 2012).
Lehnert, "Knoevenagel-Kondensation Mit TiCl4/Base-V, 3-Alkyliden-und-3-Aryliden-2, 4-Pentandione aus Aldehyden und Acetylaceton," Synthesis, 1974, pp. 667-669.
Nagamori et al., "Structure-Activity Relations of Leucine Derivatives Reveal Critical Moieties for Cellular Uptake and Activation of mTORC1-Mediated Signaling," Amino Acids, 2016, vol. 48, No. 4, pp. 1045-1048.
Pela et al., "Racemic Synthesis and Solid Phase Peptide Synthesis Application of the Chimeric Valine/Leucine Derivative 2-Amino-3,3,4-Trimethyl-Pentanoic Acid," Pharmazie, 2014, vol. 69, No. 7, pp. 496-499.

\* cited by examiner

Abbreviations: CSF = cerebrospinal fluid; PK = pharmacokinetic.
a  Time-matched CSF and blood samples were collected for 36 hours post dose.
b  Subjects remained in the clinic for at least 36 hours following the removal of the intradural catheter.

| Endpoint | Eyes Closed | | | | Eyes Open | | | |
|---|---|---|---|---|---|---|---|---|
| | Oscillatory | | Fractal | | Oscillatory | | Fractal | |
| | Compound A | Placebo | Compound A | Placebo | Compound A | Placebo | Compound A | Placebo |
| Delta (1.0 - 4.0 Hz) | ↓↓ | -- | | -- | | -- | | -- |
| Theta (4.0 - 8.0 Hz) | ↓↓↓ | -- | | -- | ↓↓** | -- | | -- |
| Alpha (8.0 - 12.0 Hz) | ↑ | -- | | -- | | -- | | -- |
| Alpha 1 (8.0 - 10.0 Hz) | ↑↑ | -- | | -- | ↓↑ | -- | | -- |
| Alpha 2 (10.0 - 12.0 Hz) | ↑ | -- | | -- | ↓↑↑ | -- | | -- |
| Beta (12.0 - 25.0 Hz) | | -- | | -- | | -- | | -- |
| Beta 1 (12.0 - 15.0 Hz) | | -- | | -- | ↓↑ | -- | | -- |
| Beta 2 (15.0 - 18.0 Hz) | ↑** | | | -- | | -- | | -- |
| Beta 3 (18.0 - 25.0 Hz) | | -- | | -- | | -- | | -- |
| Hi-Beta (25.0 - 30.0 Hz) | | | ↑** | -- | | | | -- |
| Gamma (30.0 - 50.0 Hz) | | | ↑ | -- | | | ↑ | -- |
| Gamma 1 (30.0 - 35.0 Hz) | | | ↑ | -- | | | ↑ | -- |
| Gamma 2 (35.0 - 40.0 Hz) | | | ↑ | -- | | | ↑ | -- |
| Gamma 3 (40.0 - 50.0 Hz) | | | ↑↑ | -- | | | ↑↑ | -- |
| Total (1.0 - 50.0 Hz) | | | | -- | | | | -- |
| Alpha Slow Wave Index (ASI) | ↑ | ↓↑ | | -- | ↓↑↑ | -- | | -- |
| Theta-Beta Ratio (TBR) | ↓↓ | -- | | -- | ↓↓↓** | -- | | -- |
| Dominant frequency (IAF) | | -- | | | | -- | | |

Figure 11

| Endpoint | Eyes Closed | | Eyes Open | |
|---|---|---|---|---|
| | Compound A | Placebo | Compound A | Placebo |
| Delta (1.0 - 4.0 Hz) | | -- | | -- |
| Theta (4.0 - 8.0 Hz) | | -- | | -- |
| Alpha (8.0 - 12.0 Hz) | ↑** | -- | | -- |
| Alpha 1 (8.0 - 10.0 Hz) | ↑** | -- | | -- |
| Alpha 2 (10.0 - 12.0 Hz) | ↑** | -- | | -- |
| Beta (12.0 - 25.0 Hz) | ↑ | -- | | -- |
| Beta 1 (12.0 - 15.0 Hz) | ↑ | -- | | -- |
| Beta 2 (15.0 - 18.0 Hz) | ↑ | -- | | -- |
| Beta 3 (18.0 - 25.0 Hz) | ↑↑** | ↓**↑ | | -- |
| Hi-Beta (25.0 - 30.0 Hz) | ↑↑ | ↓↑ | ↑** | -- |
| Gamma (30.0 - 50.0 Hz) | ↑↑↑** | -- | ↑ | -- |
| Gamma 1 (30.0 - 35.0 Hz) | ↑↑ | -- | ↑ | -- |
| Gamma 2 (35.0 - 40.0 Hz) | ↑↑↑ | -- | ↑↑ | -- |
| Gamma 3 (40.0 - 50.0 Hz) | ↑↑↑ | -- | ↑↑ | -- |
| Total (1.0 - 50.0 Hz) | ↑ | -- | ↑ | -- |

Figure 12

METHODS OF TREATMENT USING AN MTORC1 MODULATOR

CROSS-REFERENCE TO RELATED APPLICATIONS

This application claims the benefit of U.S. Provisional Application No. 62/929,449, filed on Nov. 1, 2019, the contents of which are hereby incorporated by reference in their entirety.

TECHNICAL FIELD OF THE INVENTION

The present invention relates to methods useful for modulating mTORC1 activity. The present invention relates to methods useful for selectively modulating mTORC1 activity. The present invention relates to methods useful for activating mTORC1.

BACKGROUND OF THE INVENTION

The mechanistic target of rapamycin complex 1 (mTORC1) protein kinase is a master growth regulator that senses diverse environmental cues, such as growth factors, cellular stresses, and nutrient and energy levels. When activated, mTORC1 phosphorylates substrates that potentiate anabolic processes, such as mRNA translation and lipid synthesis, and limits catabolic ones, such as autophagy. mTORC1 dysregulation occurs in a broad spectrum of diseases, including diabetes, epilepsy, neurodegeneration, immune response, suppressed skeletal muscle growth, and cancer among others (Howell et al., (2013) Biochemical Society transactions 41, 906-912; Kim et al., (2013) Molecules and cells 35, 463-473; Laplante and Sabatini, (2012) Cell 149, 274-293).

There is urgent and compelling unmet medical need for more effective treatments for diseases, disorders or conditions associated with mTORC1.

SUMMARY OF THE INVENTION

The present invention provides, inter alia, methods of treating depression comprising administering to a patient in need thereof a therapeutically effective amount of ((S)-2-amino-5,5-difluoro-4,4-dimethylpentanoic acid), i.e., compound A:

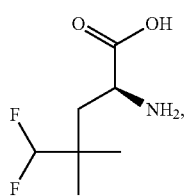

A or a pharmaceutically acceptable salt or composition thereof. In some embodiments, the depression is major depressive disorder (MDD). In some embodiments, the depression is treatment-resistant depression (TRD).

In some embodiments, the present invention further provides a composition comprising compound A, or a pharmaceutically acceptable salt thereof.

In some embodiments, the present invention further provides a unit dosage form comprising compound A, or a pharmaceutically acceptable salt thereof.

BRIEF DESCRIPTION OF THE FIGURES

FIG. 11 depicts a chart showing changes in qEEG band amplitudes after administration of a single dose of compound A. Symbols indicate either no salient changes (–), small to large increases (↑, ↑↑, ↑↑↑), small to large decreases (↓, ↓↓, ↓↓↓) or mixed decreases and increases (↓↑) in mean value differences. Changes that were confirmed to be significant treatment effects in formal ANOVA models are indicated with a double asterisk (**).

FIG. 12 depicts a chart showing changes in qEEG band coherences after administration of a single dose of compound A. Symbols indicate either no salient changes (–), small to large increases (↑, ↑↑, ↑↑↑), small to large decreases (↓, ↓↓, ↓↓↓) or mixed decreases and increases (↓↑) in mean value differences. Changes that were confirmed to be significant treatment effects in formal ANOVA models are indicated with a double asterisk (**).

DETAILED DESCRIPTION OF THE INVENTION

Figure 1:
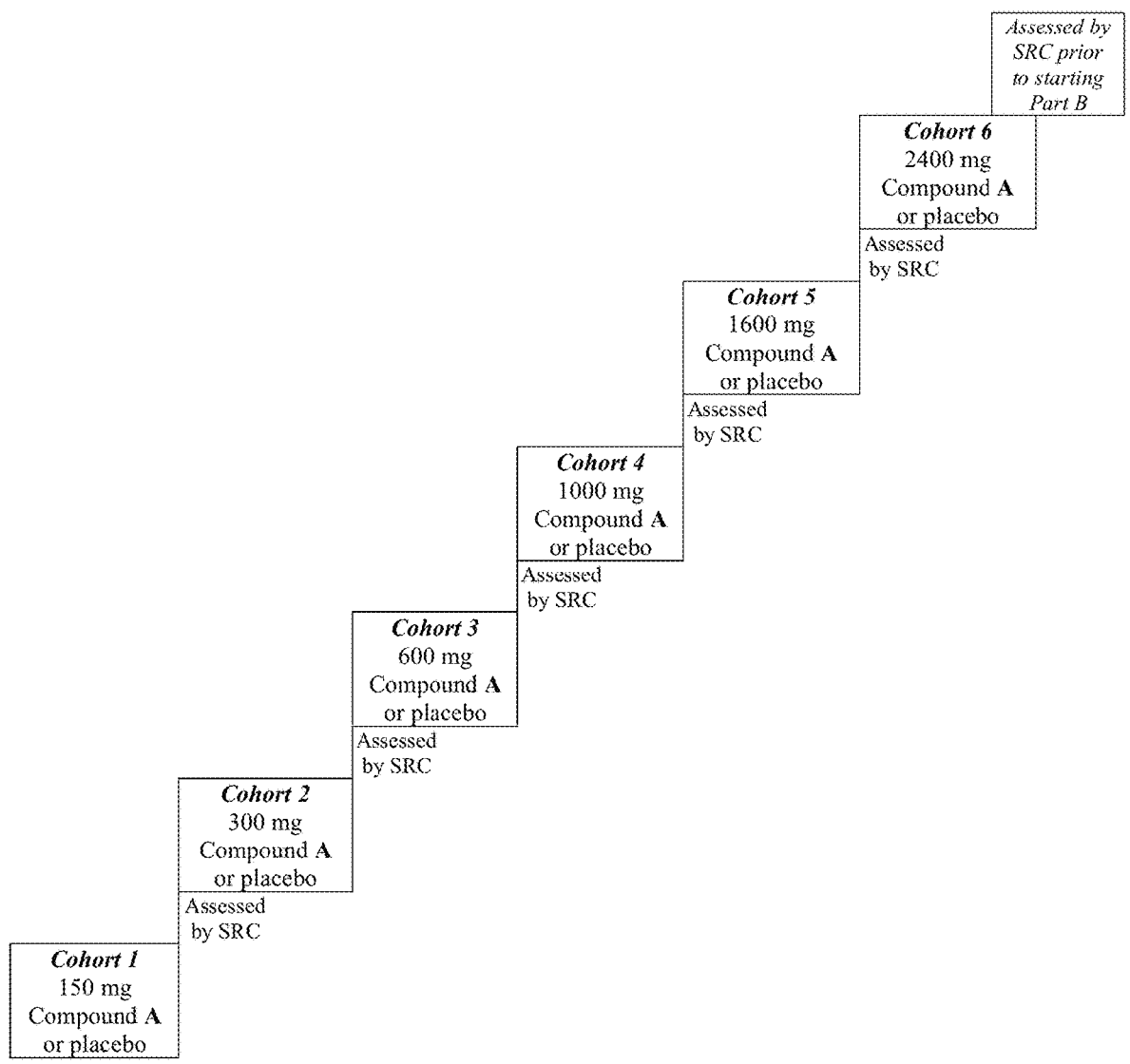
FIG. 1 depicts the dose ascension scheme for Part A of the clinical trial study described in Example 1.

General Description of Certain Embodiments of the Invention

Major depressive disorder (MDD) is a common psychiatric disorder, with a lifetime prevalence rate of ~13-17% in the United States. Although options for pharmacologic treatment have expanded significantly in the past 25 years, between one third and two thirds of patients will not respond to the first antidepressant prescribed, and up to 33 percent will not respond to multiple interventions. Novel antidepressants that relieve the symptoms of MDD in patients who have failed to respond adequately to one or more treatments, without producing significant side effects, would represent an important advance in the treatment of treatment-resistant depression (TRD).

mTORC1, also known as mechanistic target of rapamycin complex 1, is a multiprotein complex that functions as a cellular nutrient/energy/redox sensor and regulates overall metabolic homeostasis through multiple anabolic and catabolic activities, including protein, lipid, and nucleic acid synthesis. Recent data support a key role for mTORC1 activity in neurons, including regulation of spine enlargement, axon elongation, dendritic arborization, and the involvement of mTORC1 in cognition, mood, and learning and memory. Two compounds that require the activation of mTORC1 for their antidepressant activity in animal models, ketamine and rapastinel (also known as GLYX-13), have demonstrated efficacy in placebo-controlled trials in subjects with TRD.

Compound A [(S)-2-amino-5,5-difluoro-4,4-dimethylpentanoic acid] is a novel, orally bioavailable, specific, small molecule that activates mTORC1 pathway signaling in the brain, including those centers responsible for mood. In multiple preclinical rodent models of stress-induced depressive behavior, when compared head-to-head with ketamine, compound A demonstrated rapid antidepressant effects comparable to those of ketamine without producing significant adverse effects. The pharmacological activity of compound A was also found to be comparable to that of ketamine in a nonhuman primate model of anxiolytic/depressive behavioral responses. Lastly, like ketamine, the antidepressant effects of compound A were shown to be dependent on the post-synaptic activation of mTORC1 and were associated with an increase in mTORC1 downstream signaling, synaptic protein expression (e.g., GluR1 and synapsin), and synaptic arborization in layer V pyramidal neurons in the medial pre-frontal cortex of rats. Unlike ketamine, however, the pharmacological efficacy of compound A was not associated with N-methyl-D-aspartate (NMDA) receptor modulation. Taken together, these data demonstrate the antidepressant potential for compound A for the treatment of TRD.

Nonclinical toxicology studies have been performed with compound A in the rat and cynomolgus monkey. Adverse effects were not observed after single oral doses of up to 500 mg/kg in rat and up to 2000 mg/kg in cynomolgus monkey. In rats, ataxia was noted after a single oral dose of 2000 mg/kg; the ataxia resolved by 24 hours postdose.

In rats administered 160, 500, or 1000 mg/kg PO every 3 days (Q3D) for 14 days (5 doses total), the no-observed-adverse-effect level (NOAEL) was 160 mg/kg. At 500 mg/kg, findings included lymphocyte atrophy in paracortex of mesenteric nodes, but not other lymphoid tissues, and decreased eosinophil counts. At 1000 mg/kg, adverse effects included regenerative anemia in one male, considered likely an episode of gastrointestinal (GI) bleeding, and hepatocellular injury in one male, without associated histopathology findings. Other findings, not considered adverse, included slightly decreased lymphocyte, monocyte, and neutrophil counts.

In cynomolgus monkeys administered 160, 500, or 2000 mg/kg PO Q3D for 14 days (5 doses total), the NOAEL was 160 mg/kg. At ≥500 mg/kg, adverse effects included decreased heart rate and vomiting. At 2000 mg/kg, adverse effects included dehydration in one animal, likely secondary to vomiting, and increased aspartate aminotransferase (AST) in one animal.

The nonclinical safety assessment from these studies supports clinical evaluation of Compound A in humans. The initial planned dose of compound A for this study was 150 mg once daily (QD), based on evaluation of the compound A nonclinical safety data.

Accordingly, in some embodiments the present invention provides a method of treating depression in a patient in need thereof, comprising the step of administering to the patient a therapeutically effective amount of compound A, or a pharmaceutically acceptable salt thereof.

In some embodiments, the depression is Major depressive disorder ("MDD").

In some embodiments, the depression is treatment-resistant depression ("TRD").

In some embodiments, the depression is resistant to first line treatments.

In some embodiments, the depression is resistant to second line treatments.

In some embodiments, the present invention provides a composition as described herein, comprising compound A or a pharmaceutically acceptable salt thereof.

In some embodiments, the present invention provides a unit dosage form as described herein, comprising compound A or a pharmaceutically acceptable salt thereof.

Definitions

As used herein, the term "compound A" refers to ((S)-2-amino-5,5-difluoro-4,4-dimethylpentanoic acid), i.e.:

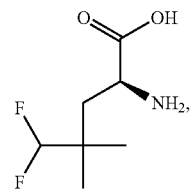

or a pharmaceutically acceptable salt thereof. U.S. Pat. No. 10,100,066 ("the '066 patent") filed Oct. 21, 2016 as U.S. patent application Ser. No. 15/331,362 and published as U.S. Pat. App. Pub. No. U.S. 2017/0114080 ("the '080 publication"), the entirety of each is incorporated herein by reference, describe certain mTORC1 modulating compounds, including compound A. Compound A is designated as compound 1-90 in the '066 patent and the synthesis of compound A is described in detail at Example 90 of the '066 patent.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}\text{ alkyl})_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the terms "about" or "approximately" have the meaning of within 20% of a given value or range. In some embodiments, the term "about" refers to within 20%, 19%, 18%, 17%, 16%, 15%, 14%, 13%, 12%, 11%, 10%, 9%, 8%, 7%, 6%, 5%, 4%, 3%, 2%, or 1% of a given value.

Description of Exemplary Methods and Uses

As used herein, the term "patient," means an animal, preferably a mammal, and most preferably a human.

As used herein, the terms "treatment," "treat," and "treating" refer to reversing, alleviating, delaying the onset of, or inhibiting the progress of a disease, disorder, or condition or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

As used herein, the phrase "mTORC1-mediated disease, disorder, or condition" refers to any disease or other deleterious condition in which mTORC1 is known to play a role. Accordingly, another embodiment of the present invention relates to treating or lessening the severity of one or more diseases in which mTORC1 is known to play a role.

Unless otherwise specified, it should be understood that when methods of the present invention described above and herein refer to administering compound A, or a pharmaceutically acceptable salt thereof, said methods also contemplate administering a pharmaceutically acceptable composition comprising compound A, or a pharmaceutically acceptable salt thereof.

As described above and herein, in some embodiments the present invention provides a method of modulating mTORC1 activity in a patient in need thereof, comprising administering to the patient a therapeutically effective amount of compound A, or a pharmaceutically acceptable salt thereof.

In some embodiments, the present invention provides a method of activating mTORC1 in a patient in need thereof, comprising administering to the patient a therapeutically effective amount of compound A, or a pharmaceutically acceptable salt thereof.

In some embodiments, the present invention provides a method of treating depression in a patient in need thereof, comprising administering to the patient a therapeutically effective amount of compound A, or a pharmaceutically acceptable salt thereof.

In some embodiments, the present invention provides a method of treating depression in a patient in need thereof, comprising administering to the patient a therapeutically effective amount of a pharmaceutically acceptable composition comprising compound A, or a pharmaceutically acceptable salt thereof.

In some embodiments, the patient is diagnosed with major depressive disorder ("MDD"). In some such embodiments, the patient is diagnosed with major depressive disorder (MDD) without psychotic features, as described by DSM-5 criteria. In some embodiments, the patient does not have a history of psychotic disorder, for instance a psychotic disorder as described and defined in the Examples included herein.

In some embodiments, the depression is treatment-resistant depression ("TRD").

In some embodiments, the depression is resistant to first line treatments.

In some embodiments, the treatment resistant depression is resistant to second line treatments.

In some embodiments, the patient is experiencing a depressive episode and has had at least one inadequate response to at least one antidepressant during the depressive episode. In some embodiments, the patient is experiencing a depressive episode and has had an inadequate response to two, three, or four different antidepressants during the depressive episode.

In some embodiments, the patient is assessed to have a Montgomery-Asberg Depression Rating Scale (MADRS) total score of ≥21 prior to treatment with compound A.

In some embodiments, the patient is assessed to have a Raskin Depression Rating Scale score of ≥9 prior to treatment with compound A.

In some embodiments, the patient has not used an antidepressant for at least one, two, three, or four weeks prior to treatment with compound A, or a pharmaceutically acceptable salt thereof.

In some embodiments, the patient is 18 years or older.

In some embodiments, the patient does not have a seizure disorder.

In some embodiments, the patient does not have a clinically significant abnormality on electroencephalogram (EEG).

In some embodiments, a patient does not have one or more of the exclusion criteria as set forth in the Examples included herein.

In some embodiments, a patient has one or more of the inclusion criteria as set forth in the Examples included herein.

In some embodiments, the present invention provides a method of treating depression in a patient in need thereof, comprising administering to the patient a therapeutically effective amount of compound A, or a pharmaceutically acceptable salt thereof, wherein the patient experiences at least a 50% reduction in depression scale score. In some embodiments, the patient experiences at least a 50% reduction in depression scale score within fewer than six weeks of administration of compound A, or pharmaceutically acceptable salt thereof. In some embodiments, the patient experiences at least a 50% reduction in depression scale score within fewer than four weeks of administration of compound A, or pharmaceutically acceptable salt thereof. In some embodiments, the patient experiences at least a 50% reduction in depression scale score within two weeks of administration of compound A, or pharmaceutically acceptable salt thereof. In some embodiments, the patient experiences at least a 50% reduction in depression scale score within fewer than two weeks of administration of compound A, or pharmaceutically acceptable salt thereof. In some embodiments, the patient experiences at least a 50% reduction in depression scale score within one week of administration of compound A, or pharmaceutically acceptable salt thereof. In some embodiments, the patient experiences at least a 50% reduction in depression scale score within seven days of administration of compound A, or pharmaceutically acceptable salt thereof. In some embodiments, the patient experiences at least a 50% reduction in depression scale score within six days of administration of compound A, or pharmaceutically acceptable salt thereof. In some embodiments, the patient experiences at least a 50% reduction in depression scale score within five days of administration of compound A, or pharmaceutically acceptable salt thereof. In some embodiments, the patient experiences at least a 50% reduction in depression scale score within four days of administration of compound A, or pharmaceutically acceptable salt thereof. In some embodiments, the patient experiences at least a 50% reduction in depression scale score within three days of administration of compound A, or pharmaceutically acceptable salt thereof. In some embodiments, the patient experiences at least a 50% reduction in depression scale score within two days of administration of compound A, or pharmaceutically acceptable salt thereof. In some embodiments, the patient experiences at least a 50% reduction in depression scale score within one day of administration of compound A, or pharmaceutically acceptable salt thereof. In some embodiments, the patient experiences at least a 50% reduction in depression scale score within twenty-four hours of administration of compound A, or pharmaceutically acceptable salt thereof. In some embodiments, the patient experiences at least a 10%, 20%, 30%, or 40% reduction in depression scale score within twenty-four hours of administration of compound A, or pharmaceutically acceptable salt thereof. In some embodiments, the patient experiences at least a 10%, 20%, 30%, or 40% reduction in depression scale score within twelve hours of administration of compound A, or pharmaceutically acceptable salt thereof. In some embodiments, the patient experiences at least a 10%, 20%, 30%, or 40% reduction in depression scale score within two, three, four, five, six, seven, eight, nine, ten, or eleven hours of administration of compound A, or pharmaceutically acceptable salt thereof. In some embodiments, the depression scale score is selected from the Montgomery-Asberg Depression Rating Scale (MADRS), the Hamilton Depression Rating Scale (HAMD-6), the Inventory of Depression Symptomatology Self-Rated Scale (IDS-SR), and the Clinical Global Impression Severity Scale (CGI-S). In some embodiments, the depression scale score is selected from any of the depression rating scales described above and herein.

In some embodiments, a method of the present invention is characterized as achieving a clinically significant antidepressant effect, as measured using standardized effect size statistics, wherein an effect size of 0.40 or higher is considered to be indicative of a clinically significant effect. For instance, in some embodiments, an effect size is measured according to any of the depression scales described above and herein, wherein the effect size at a particular time interval is ≥0.20, 0.30, 0.40, 0.50, 0.60, 0.70, 0.80, 0.90, or 1.0. In some embodiments, an effect size is measured according to any of the depression scales described above and herein, wherein the effect size at 2-4 hours is ≥0.20, 0.30, 0.40, 0.50, 0.60, 0.70, 0.80, 0.90, or 1.0. In some embodiments, an effect size is measured according to any of the depression scales described above and herein, wherein the effect size at 4-8 hours is ≥0.20, 0.30, 0.40, 0.50, 0.60, 0.70, 0.80, 0.90, or 1.0. In some embodiments, an effect size is measured according to any of the depression scales described above and herein, wherein the effect size at 8-12 hours is ≥0.20, 0.30, 0.40, 0.50, 0.60, 0.70, 0.80, 0.90, or 1.0. In some embodiments, an effect size is measured according to any of the depression scales described above and herein, wherein the effect size as measured at 12, 24, 36, 48, or 72 hours is ≥0.20, 0.30, 0.40, 0.50, 0.60, 0.70, 0.80, 0.90, or 1.0. In some such embodiments, the size effect is ≥0.40. In some such embodiments, the size effect is ≥0.50.

In some embodiments, the present invention provides a method of treating depression in a patient in need thereof, comprising administering to the patient a therapeutically effective amount of compound A, or a pharmaceutically acceptable salt thereof, wherein the patient experiences a reduction in depression scale score comparable to ketamine administered via i.p. injection. In some embodiments, the reduction in depression scale score results from a single administration. In some such embodiments, administration is oral. In some embodiment, the reduction in depression scale score results from at least two administrations. In some such embodiments, administration is oral. In some embodiments, the reduction in depression scale score results from a plurality of oral administrations. In some such embodiments, administration is oral.

In some embodiments, the present invention provides a method of eliciting a rapid onset antidepressant activity in a patient in need thereof, comprising administering to the patient a therapeutically effective amount of compound A, or a pharmaceutically acceptable salt thereof. In some such embodiments, the patient suffers from TRD. In some embodiments, the rapid onset antidepressant activity occurs within two weeks of administration of compound A, or pharmaceutically acceptable salt thereof. In some embodiments, the rapid onset antidepressant activity occurs within one week of administration of compound A, or pharmaceutically acceptable salt thereof. In some embodiments, the rapid onset antidepressant activity occurs within seven days of administration of compound A, or pharmaceutically acceptable salt thereof. In some embodiments, the rapid onset antidepressant activity occurs within six days of administration of compound A, or pharmaceutically acceptable salt thereof. In some embodiments, the rapid onset antidepressant activity occurs within five days of administration of compound A, or pharmaceutically acceptable salt thereof. In some embodiments, the rapid onset antidepressant activity occurs within four days of compound A, or pharmaceutically acceptable salt thereof. In some embodiments, the rapid onset antidepressant activity occurs within three days of administration of compound A, or pharmaceutically acceptable salt thereof. In some embodiments, the rapid onset antidepressant activity occurs within two days of administration of compound A, or pharmaceutically acceptable salt thereof. In some embodiments, the rapid onset antidepressant activity occurs within one day of administration of compound A, or pharmaceutically acceptable salt thereof. In some embodiments, the rapid onset antidepressant activity occurs within less than 24 hours of administration of compound A, or pharmaceutically acceptable salt thereof. In some embodiments, the rapid onset antidepressant activity occurs within less than 23, 22, 21, 20, 19, 18, 17, 16, 15, 14, 13, 12, 11, 10, 9, 8, 7, 6, 5, 4, 3, or 2 hours of administration of compound A, or pharmaceutically acceptable salt thereof.

In some embodiments, the present invention provides a method of eliciting a long-lasting, sustained antidepressant activity, in a patient in need thereof, comprising administering to the patient a therapeutically effective amount of compound A, or a pharmaceutically acceptable salt thereof.

In some embodiments, the patient in need thereof suffers from TRD. In some embodiments, the long-lasting, sustained antidepressant activity persists for at least twenty-four hours after a single administration of compound A or a pharmaceutically acceptable salt thereof. In some embodiments, the long-lasting, sustained antidepressant activity persists for at least two days. In some embodiments, the long-lasting, sustained antidepressant activity persists for at least three days. In some embodiments, the long-lasting, sustained antidepressant activity persists for at least four days. In some embodiments, the long-lasting, sustained antidepressant activity persists for at least five days. In some embodiments, the long-lasting, sustained antidepressant activity persists for at least six days. In some embodiments, the long-lasting, sustained antidepressant activity persists for at least seven days.

In some embodiments, the present invention provides a method of eliciting antidepressant activity that is both rapid onset and long-lasting, sustained.

In some embodiments, the present invention provides a method of eliciting a positive behavioral response in a patient in need thereof, comprising administering to the patient a composition comprising compound A, or a pharmaceutically acceptable salt thereof. In some embodiments, the patient suffers from TRD. In some embodiments, the positive behavioral response correlates with an improvement in mood. In some embodiments, the positive behavioral response correlates with a reduction of anxiety. In some embodiments, the positive behavioral response correlates with an improved ability to cope with stress. In some embodiments, the positive behavioral response correlates with an improvement in apparent sadness. In some embodiments, the positive behavioral response correlates with an improvement in reported sadness. In some embodiments, the positive behavioral response correlates with an improvement in sleep. In some embodiments, the positive behavioral response correlates with an improvement in appetite. In some embodiments, the positive behavioral response correlates with an improvement in ability to concentrate. In some embodiments, the positive behavioral response correlates with an improvement in self-esteem. In some embodiments, the positive behavioral response correlates with an improvement in level of lassitude. In some embodiments, the positive behavioral response correlates with a reduction pessimistic or suicidal thoughts. In some embodiments, the positive behavioral response correlates with an increased interest in work or other activities. In some embodiments, the positive behavioral response correlates with a reduction in somatic symptoms. In some embodiments, the positive behavioral response correlates with a reduction in symptoms of psychomotor retardation.

In some embodiments, the present invention provides a method of eliciting a rapid onset, positive behavioral response is a patient in need thereof, comprising administering to the patient a therapeutically effective amount of compound A, or a pharmaceutically acceptable salt thereof. In some embodiments, the patient suffers from TRD. In some embodiments, the positive behavioral response occurs within less than twenty-four hours of administration. In some embodiments, the positive behavioral response occurs within one day of administration. In some embodiments, the positive behavioral response occurs within two days of administration. In some embodiments, the positive behavioral response occurs within three days of administration. In some embodiments, the positive behavioral response occurs within four days of administration. In some embodiments, the positive behavioral response occurs within five days of administration. In some embodiments, the positive behavioral response occurs within six days of administration. In some embodiments, the positive behavioral response occurs within seven days of administration. In some embodiments, the positive behavioral response occurs within one week of administration.

In some embodiments, the present invention provides a method of eliciting a long-lasting, sustained positive behavioral response in a patient in need thereof, comprising administering to the patient a therapeutically effective amount of compound A, or a pharmaceutically acceptable salt thereof. In some embodiments, the patient suffers from TRD. In some embodiments, the long-lasting, sustained positive behavioral response persists for longer than one day. In some embodiments, the long-lasting, sustained positive behavioral response persists for at least two days. In some embodiments, the long-lasting, sustained positive behavioral response persists for at least three days. In some embodiments, the long-lasting, sustained positive behavioral response persists for at least four days. In some embodiments, the long-lasting, sustained positive behavioral response persists for at least five days. In some embodiments, the long-lasting, sustained positive behavioral response persists for at least six days. In some embodiments, the long-lasting, sustained positive behavioral response persists for at least seven days.

In some embodiments, the present invention provides a method of eliciting a positive behavioral response that is both rapid onset and long-lasting, sustained.

Dosing

In some embodiments, a method of the present invention comprises administering to a patient in need thereof a therapeutically effective amount of compound A, or pharmaceutically acceptable salt thereof, wherein the therapeutically effective amount comprises a total daily dose of about 10 mg to about 5000 mg, or about 20 mg to about 4000 mg, or about 40 mg to about 4000 mg, or about 60 mg to about 4000 mg, or about 80 mg to about 4000 mg, or about 100 mg to about 4000 mg, or about 120 mg to about 4000 mg, or about 130 mg to about 4000 mg, or about 140 mg to about 4000 mg, or about 100 mg to about 3000 mg, or about 150 mg to about 3000 mg, or about 160 mg to about 3000 mg, or about 170 mg to about 3000 mg, or about 180 mg to about 3000 mg, or about 190 mg to about 3000 mg, or about 200 mg to about 3000 mg, or about 210 mg to about 3000 mg, or about 220 mg to about 3000 mg, or about 230 mg to about 3000 mg, or about 240 mg to about 3000 mg, or about 250 mg to about 3000 mg, or about 260 mg to about 3000 mg, or about 270 mg to about 3000 mg, or about 280 mg to about 3000 mg, or about 290 mg to about 3000 mg, or about 300 mg to about 3000 mg, or about 310 mg to about 3000 mg, or about 320 mg to about 3000 mg, or about 330 mg to about 3000 mg, or about 340 mg to about 3000 mg, or about 350 mg to about 3000 mg, or about 360 mg to about 3000 mg, or about 370 mg to about 3000 mg, or about 380 mg to about 3000 mg, or about 390 mg to about 3000 mg, or about 400 mg to about 3000 mg, or about 410 mg to about 3000 mg, or about 420 mg to about 3000 mg, or about 430 mg to about 3000 mg, or about 440 mg to about 3000 mg, or about 450 mg to about 3000 mg, or about 460 mg to about 3000 mg, or about 470 mg to about 3000 mg, or about 480 mg to about 3000 mg, or about 490 mg to about 3000 mg, or about 500 mg to about 3000 mg, or about 510 mg to about 3000 mg, or about 520 mg to about 3000 mg, or about 530 mg to about 3000 mg, or about 540 mg to about 3000 mg, or about 550 mg to about 3000 mg, or about 560 mg to about 3000 mg, or about 570 mg to about 3000 mg, or about 580 mg to about 3000 mg, or about 590 mg to about 3000 mg, or about 600 mg to about 3000 mg, or about 610 mg to about 3000 mg, or about 620 mg to about 3000 mg, or about 630 mg to about 3000 mg, or about 640 mg to about 3000 mg, or about 650 mg to about 3000 mg, or about 660 mg to about 3000 mg, or about 670 mg to about 3000 mg, or about 680 mg to about 3000 mg, or about 690 mg to about 3000 mg, or about 700 mg to about 3000 mg, or about 710 mg to about 3000 mg, or about 720 mg to about 3000 mg, or about 730 mg to about 3000 mg, or about 740 mg to about 3000 mg, or about 750 mg to about 3000 mg, or about 760 mg to about 3000 mg, or about 770 mg to about 3000 mg, or about 780 mg to about 3000 mg, or about 790 mg to about 3000 mg, or about 800 mg to about 3000 mg, or about 810 mg to about 3000 mg, or about 820 mg to about 3000 mg, or about 830 mg to about 3000 mg, or about 840 mg to about 3000 mg, or about 850 mg to about 3000 mg, or about 860 mg to about 3000 mg, or about 870 mg to about 3000 mg, or about 880 mg to about 3000 mg, or about 890 mg to about 3000 mg, or about 900 mg to about 3000 mg, or about 910 mg to about 3000 mg, or about 920 mg to about 3000 mg, or about 930 mg to about 3000 mg, or about 940 mg to about 3000 mg, or about 950 mg to about 3000 mg, or about 960 mg to about 3000 mg, or about 970 mg to about 3000 mg, or about 980 mg to about 3000 mg, or about 990 mg to about 3000 mg, or about 1000 mg to about 3000 mg, or about 1000 mg to about 2500 mg, or about 1000 mg to about 2000 mg, or about 400 mg to about 2400 mg, or about 800 mg to about 2400 mg, or about 800 mg to about 1600 mg, or about 1600 mg to about 2400 mg.

In some embodiments, a method of the present invention comprises administering to a patient in need thereof a therapeutically effective amount of compound A, or pharmaceutically acceptable salt thereof, wherein the therapeutically effective amount comprises a total daily dose of about 50 mg to about 1600 mg, or about 50 mg to about 1500 mg, or about 50 mg to about 1400 mg, or about 50 mg to about 1300 mg, or about 50 mg to about 1200 mg, or about 50 mg to about 1100 mg, or about 50 mg to about 1000 mg, or about 50 mg to about 900 mg, or about 50 mg to about 800 mg, or about 50 mg to about 700 mg, or about 50 mg to about 400 mg, or about 50 mg to about 300 mg, or about 50 mg to about 200 mg, or about 50 mg to about 100 mg, or about 100 mg to about 500 mg, or about 100 mg to about 400 mg, or about 100 mg to about 300 mg, or about 100 mg to about 200 mg, or about 200 mg to about 1000 mg, or about 200 mg to about 900 mg, or about 200 mg to about 800 mg, or about 200 mg to about 700 mg, or about 200 mg to about 600 mg, or about 200 mg to about 500 mg, or about 200 mg to about 400 mg.

In some embodiments, a method of the present invention comprises administering to a patient in need thereof a therapeutically effective amount of compound A, or pharmaceutically acceptable salt thereof, wherein the therapeutically effective amount comprises a total daily dose of about 50 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, about 2000 mg, about 2050 mg, about 2100 mg, about 2150 mg, about 2200 mg, about 2250 mg, about 2300 mg, about 2350 mg, about 2400 mg, about 2450 mg, about 2500 mg, about 2550 mg, about 2600 mg, about 2650 me, about 2700 mg, about 2750 mg, about 2800 mg, about 2850 mg, about 2900 mg, about 2950 mg, or about 3000 mg. In some such embodiments, a total daily dose is about 150, about 300, about 400, about 600, about 800, about 1000, about 1600, about 2400, or about 3000 mg.

In some embodiments, a method of the present invention comprises administering to a patient in need thereof a therapeutically effective amount of compound A, or pharmaceutically acceptable salt thereof, wherein the therapeutically effective amount comprises a total daily dose between about 1 to about 100 mg/kg, or about 1 to about 90 mg/kg, or about 1 to about 80 mg/kg, or about 1 to about 70 mg/kg, or about 1 to about 60 mg/kg, or about 1 to about 50 mg/kg, or about 1 to about 40 mg/kg, or about 1 to about 35 mg/kg, or about 1 to about 30 mg/kg, or about 1 to about 25 mg/kg, or about 1 to about 20 mg/kg, or about 1 to about 19 mg/kg, or about 1 to about 18 mg/kg, or about 1 to about 17 mg/kg, or about 1 to about 16 mg/kg, or about 1 to about 15 mg/kg, or about 1 to about 14 mg/kg, or about 1 to about 13 mg/kg, or about 1 to about 12 mg/kg, or about 1 to about 11 mg/kg, or about 1 to about 10 mg/kg, or about 1 to about 9 mg/kg, or about 1 to about 8 mg/kg, or about 1 to about 7 mg/kg, or about 1 to about 6 mg/kg, or about 1 to about 5 mg/kg, or about 1 to about 4 mg/kg, or about 1 to about 3 mg/kg. In some embodiments, a total daily dose is between about 2 mg/kg and about 40 mg/kg, or about 5 mg/kg and about 40 mg/kg, or about 10 mg/kg and about 40 mg/kg, or about 15 mg/kg and about 40 mg/kg, or about 20 mg/kg and about 40 mg/kg, or about 25 mg/kg and about 40 mg/kg, or about 30 mg/kg and about 40 mg/kg, or about 35 mg/kg and about 40 mg/kg of the patient's body weight per day.

In some embodiments, a total daily dose of compound A, or pharmaceutically acceptable salt thereof, is administered as once a day (QD). In some such embodiments, a total daily dose is any of those described above and herein. In some such embodiments, a total daily dose is about 150, about 300, about 400, about 600, about 800, about 1000, about 1600, about 2400, or about 3000 mg.

In some embodiments, a total daily dose is administered as two, three, or four doses in one day. In some such embodiments, each dose is identical. In some such embodiments, at least one dose is different from another dose. In some embodiments, a total daily dose is any of those described above and herein, wherein the dose is administered "BID". In some embodiments, a total daily dose is any of those described above and herein, wherein the dose is administered "TID". In some embodiments, a total daily dose is any of those described above and herein, wherein the dose is administered "QID".

In some embodiments, a total daily dose is administered to a patient under fed conditions. In some such embodiments, a total daily dose is any of those described above and herein. In some such embodiments, a total daily dose is administered QD. In some such embodiments, a total daily dose is administered orally. In some embodiments, a total daily dose is administered daily for at least 1, 2, 3, 4, 5, 6, or 7 consecutive days.

In some embodiments, a total daily dose is administered to a patient under fasted conditions. In some such embodiments, a total daily dose is any of those described above and herein. In some such embodiments, a total daily dose is administered QD. In some such embodiments, a total daily dose is administered orally. In some such embodiments, the patient fasts for at least about 1, 2, 3, 4, 5, 6, 7, 8, 9, 10, 11, 12, 13, 14, 15, 16, 17, 18, 19, 20, 21, 22, 23, or 24 hours prior to administration. In some such embodiments, the patient fasts for at least about two to eight hours prior to administration. In some such embodiments, the patient fasts for about two hours, about four hours, or about eight hours prior to administration.

In some embodiments, the patient fasts for an amount of time after administration. For instance, in some embodiments a patient fasts for about 1, 2, 3, 4, 5, 6, 7, or 8 hours after administration. In some embodiments, a patient fasts for about two hours after administration.

In some embodiments, a total daily dose of about 150 mg of compound A, or pharmaceutically acceptable salt thereof, is administered to a patient once a day under fasted conditions. In some embodiments, a total daily dose of about 150 mg of compound A, or pharmaceutically acceptable salt thereof, is administered to a patient once a day under fed conditions. In some embodiments, a total daily dose of about 300 mg of compound A, or pharmaceutically acceptable salt thereof, is administered to a patient once a day under fasted conditions. In some embodiments, a total daily dose of about 300 mg of compound A, or pharmaceutically acceptable salt thereof, is administered to a patient once a day under fed conditions. In some embodiments, a total daily dose of about 400 mg of compound A, or pharmaceutically acceptable salt thereof, is administered to a patient once a day under fasted conditions. In some embodiments, a total daily dose of about 400 mg of compound A, or pharmaceutically acceptable salt thereof, is administered to a patient once a day under fed conditions. In some embodiments, a total daily dose of about 600 mg of compound A, or pharmaceutically acceptable salt thereof, is administered to a patient once a day under fasted conditions. In some embodiments, a total daily dose of about 600 mg of compound A, or pharmaceutically acceptable salt thereof, is administered to a patient once a day under fed conditions. In some embodiments, a total daily dose of about 800 mg of compound A, or pharmaceutically acceptable salt thereof, is administered to a patient once a day under fasted conditions. In some embodiments, a total daily dose of about 800 mg of compound A, or pharmaceutically acceptable salt thereof, is administered to a patient once a day under fed conditions. In some embodiments, a total daily dose of about 1000 mg of compound A, or pharmaceutically acceptable salt thereof, is administered to a patient once a day under fasted conditions. In some embodiments, a total daily dose of about 1000 mg of compound A, or pharmaceutically acceptable salt thereof, is administered to a patient once a day under fed conditions. In some embodiments, a total daily dose of about 1600 mg of compound A, or pharmaceutically acceptable salt thereof, is administered to a patient once a day under fasted conditions. In some embodiments, a total daily dose of about 1600 mg of compound A, or pharmaceutically acceptable salt thereof, is administered to a patient once a day under fed conditions. In some embodiments, a total daily dose of about 2400 mg of compound A, or pharmaceutically acceptable salt thereof, is administered to a patient once a day under fasted conditions. In some embodiments, a total daily dose of about 2400 mg of compound A, or pharmaceutically acceptable salt thereof, is administered to a patient once a day under fed conditions. In some embodiments, a total daily dose of greater than about 2400 mg of compound A, or pharmaceutically acceptable salt thereof, is administered to a patient once a day under fasted conditions. In some embodiments, a total daily dose of greater than about 2400 mg of compound A, or pharmaceutically acceptable salt thereof, is administered to a patient once a day under fed conditions.

In some embodiments, provided methods comprise administering to a patient in need thereof a therapeutically effective amount of compound A, or pharmaceutically acceptable salt thereof, comprising administering a single dose. In some embodiments, provided methods comprise administering to a patient in need thereof a therapeutically effective amount of compound A, or pharmaceutically acceptable salt thereof, comprising administering at least two doses. In some such embodiments, administering the at least two doses comprises administering a first dose about 24 hours prior to administering a second dose. In some such embodiments, administering at least two doses comprises administering a first dose about 48 hours prior to administering a second dose. In some embodiments, provided methods comprise administering to a patient in need thereof a therapeutically effective amount of compound A, or pharmaceutically acceptable salt thereof, comprising administering a plurality of doses. In some embodiments, provided methods comprise administering to a patient in need thereof a therapeutically effective amount of compound A, or pharmaceutically acceptable salt thereof, comprising administering compound A daily, weekly, or monthly. In some embodiments, provided methods comprise administering to a patient in need thereof a therapeutically effective amount of compound A, or pharmaceutically acceptable salt thereof, comprising administering compound A at the same time each day. For instance, in some embodiments, compound A is administered at the same time each morning. In some embodiments, compound A is administered at the same time each evening.

Unit Dosage Forms

In some embodiments, methods of the present invention comprise administering to a patient in need thereof a pharmaceutical composition comprising one or more unit doses of compound A, or pharmaceutically acceptable salt thereof. In some such embodiments, a unit dose is about 10 mg to about 5000 mg, or about 20 mg to about 4000 mg, or about 40 mg to about 4000 mg, or about 60 mg to about 4000 mg, or about 80 mg to about 4000 mg, or about 100 mg to about 4000 mg, or about 120 mg to about 4000 mg, or about 130 mg to about 4000 mg, or about 140 mg to about 4000 mg, or about 150 mg to about 3000 mg, or about 160 mg to about 3000 mg, or about 170 mg to about 3000 mg, or about 180 mg to about 3000 mg, or about 190 mg to about 3000 mg, or about 200 mg to about 3000 mg, or about 210 mg to about 3000 mg, or about 220 mg to about 3000 mg, or about 230 mg to about 3000 mg, or about 240 mg to about 3000 mg, or about 250 mg to about 3000 mg, or about 260 mg to about 3000 mg, or about 270 mg to about 3000 mg, or about 280 mg to about 3000 mg, or about 290 mg to about 3000 mg, or about 300 mg to about 3000 mg, or about 310 mg to about 3000 mg, or about 320 mg to about 3000 mg, or about 330 mg to about 3000 mg, or about 340 mg to about 3000 mg, or about 350 mg to about 3000 mg, or about 360 mg to about 3000 mg, or about 370 mg to about 3000 mg, or about 380 mg to about 3000 mg, or about 390 mg to about 3000 mg, or about 400 mg to about 3000 mg, or about 410 mg to about 3000 mg, or about 420 mg to about 3000 mg, or about 430 mg to about 3000 mg, or about 440 mg to about 3000 mg, or about 450 mg to about 3000 mg, or about 460 mg to about 3000 mg, or about 470 mg to about 3000 mg, or about 480 mg to about 3000 mg, or about 490 mg to about 3000 mg, or about 500 mg to about 3000 mg, or about 510 mg to about 3000 mg, or about 520 mg to about 3000 mg, or about 530 mg to about 3000 mg, or about 540 mg to about 3000 mg, or about 550 mg to about 3000 mg, or about 560 mg to about 3000 mg, or about 570 mg to about 3000 mg, or about 580 mg to about 3000 mg, or about 590 mg to about 3000 mg, or about 600 mg to about 3000 mg, or about 610 mg to about 3000 mg, or about 620 mg to about 3000 mg, or about 630 mg to about 3000 mg, or about 640 mg to about 3000 mg, or about 650 mg to about 3000 mg, or about 660 mg to about 3000 mg, or about 670 mg to about 3000 mg, or about 680 mg to about 3000 mg, or about 690 mg to about 3000 mg, or about 700 mg to about 3000 mg, or about 710 mg to about 3000 mg, or about 720 mg to about 3000 mg, or about 730 mg to about 3000 mg, or about 740 mg to about 3000 mg, or about 750 mg to about 3000 mg, or about 760 mg to about 3000 mg, or about 770 mg to about 3000 mg, or about 780 mg to about 3000 mg, or about 790 mg to about 3000 mg, or about 800 mg to about 3000 mg, or about 810 mg to about 3000 mg, or about 820 mg to about 3000 mg, or about 830 mg to about 3000 mg, or about 840 mg to about 3000 mg, or about 850 mg to about 3000 mg, or about 860 mg to about 3000 mg, or about 870 mg to about 3000 mg, or about 880 mg to about 3000 mg, or about 890 mg to about 3000 mg, or about 900 mg to about 3000 mg, or about 910 mg to about 3000 mg, or about 920 mg to about 3000 mg, or about 930 mg to about 3000 mg, or about 940 mg to about 3000 mg, or about 950 mg to about 3000 mg, or about 960 mg to about 3000 mg, or about 970 mg to about 3000 mg, or about 980 mg to about 3000 mg, or about 990 mg to about 3000 mg, or about 1000 mg to about 3000 mg, or about 1000 mg to about 2500 mg, or about 1000 mg to about 2000 mg, or about 400 mg to about 2400 mg, or about 800 mg to about 2400 mg, or about 800 mg to about 1600 mg, or about 1600 mg to about 2400 mg.

In some such embodiments, a unit dose is 50 mg to about 1600 mg, or about 50 mg to about 1500 mg, or about 50 mg to about 1400 mg, or about 50 mg to about 1300 mg, or about 50 mg to about 1200 mg, or about 50 mg to about 1100 mg, or about 50 mg to about 1000 mg, or about 50 mg to about 900 mg, or about 50 mg to about 800 mg, or about 50 mg to about 700 mg, or about 50 mg to about 400 mg, or about 50 mg to about 300 mg, or about 50 mg to about 200 mg, or about 50 mg to about 100 mg, or about 100 mg to about 400 mg, or about 100 mg to about 300 mg, or about 100 mg to about 200 mg, or about 200 mg to about 1000 mg, or about 200 mg to about 900 mg, or about 200 mg to about 800 mg, or about 200 mg to about 700 mg, or about 200 mg to about 600 mg, or about 200 mg to about 500 mg, or about 200 mg to about 400 mg.

In some embodiments, a unit dose of compound A, or pharmaceutically acceptable salt thereof, is about 50 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, about 2000 mg, about 2050 mg, about 2100 mg, about 2150 mg, about 2200 mg, about 2250 mg, about 2300 mg, about 2350 mg, about 2400 mg, about 2450 mg, about 2500 mg, about 2550 mg, about 2600 mg, about 2650 me, about 2700 mg, about 2750 mg, about 2800 mg, about 2850 mg, about 2900 mg, about 2950 mg, or about 3000 mg. In some such embodiments, a unit dose of compound A, or pharmaceutically acceptable salt thereof, comprises about 150, about 300, about 400, about 600, about 800, about 1000, about 1600, about 2400 mg, or about 3000 mg.

In some embodiments, a unit dose of compound A, or pharmaceutically acceptable salt thereof, is administered as a single dose (QD). In some such embodiments, a unit dose is about 150, about 300, about 400, about 600, about 800, about 1000, about 1600, about 2400 mg, or about 3000 mg. In some such embodiments, a unit dose is any of those described above and herein. In some embodiments, the unit dosage form is administered as a liquid. For instance, in some embodiments a unit dosage form comprises compound A, or pharmaceutically acceptable salt thereof, and one or more pharmaceutically acceptable liquids for dissolving or suspending compound A, or pharmaceutically acceptable salt thereof. In some embodiments, the one or more pharmaceutically acceptable liquids for dissolving or suspending compound A, or pharmaceutically acceptable salt thereof, comprises water. In some embodiments, the one or more pharmaceutically acceptable liquids for dissolving or suspending compound A, or pharmaceutically acceptable salt thereof, comprises a flavoring agent. In some such embodiments, a unit dosage form contains between about 10 mg and about 100 mg, or between about 10 mg and about 90 mg, or between about 10 mg and about 80 mg, or between about 10 mg and about 70 mg, or between about 15 mg and about 60 mg, or between about 15 mg and about 55 mg, or between about 15 mg and about 50 mg, or between about 20 and about 50 mg of compound A per gram of total solution weight. In some such embodiments, a unit dosage form contains about 5, 10, 15, 20, 25, 30, 35, 40, 45, 50, 55, 60, 65, 70, 75, 80, 85, 90, 95, or 100 mg of compound A per gram of total solution weight.

In some embodiments, a unit dose of compound A is a liquid formulation for oral administration, wherein compound A is present in a concentration of about 10 mg/mL, or about 15 mg/mL, or about 20 mg/mL, or about 25 mg/mL, or about 30 mg/mL, or about 35 mg/mL, or about 40 mg/mL, or about 45 mg/mL, or about 50 mg/mL, or about 55 mg/mL, or about 60 mg/mL of total solution. In certain embodiments, a unit dose is a liquid formulation for oral administration, wherein compound A is present in a concentration of about 40 mg/mL of total solution.

Pharmaceutically Acceptable Compositions

In some embodiments, a method of the present invention comprises administering a composition comprising a therapeutically effective amount of compound A, or a pharmaceutically acceptable salt thereof, and a pharmaceutically acceptable carrier, adjuvant, or vehicle. In certain embodiments, compositions for use in methods provided herein are formulated for administration to a patient in need of such composition, for instance a patient suffering from depression. In some embodiments, such compositions are formulated for oral administration to a patient.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions for use in provided methods may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

In some embodiments, pharmaceutically acceptable compositions for use in provided methods are formulated for oral administration. Such formulations may be administered with or without food. In some embodiments, pharmaceutically acceptable compositions for use in provided methods are administered without food. In some embodiments, pharmaceutically acceptable compositions for use in provided methods are administered with food.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The compound can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Alternatively, pharmaceutically acceptable compositions for use in provided methods may be administered in the form of suppositories for rectal or vaginal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions for use in provided methods may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, pharmaceutically acceptable compositions for use in provided methods may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Pharmaceutically acceptable compositions for use in provided methods may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound A that may be combined with the carrier materials to produce a composition in a single dosage form will vary depending upon the host treated and the particular mode of administration. In some embodiments, compositions for use in provided methods should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the age, body weight, general health, sex, diet, time of administration, rate of excretion, drug combination, and the judgment of the treating physician and the severity of the particular disease being treated.

As described above and herein, pharmaceutically acceptable compositions for use in provided methods can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, Compound A may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

All features of each of the aspects of the invention apply to all other aspects mutatis mutandis.

In order that the invention described herein may be more fully understood, the following examples are set forth. It should be understood that these examples are for illustrative purposes only and are not to be construed as limiting this invention in any manner.

EXEMPLIFICATION

Example 1: A Randomized, Double-Blind, Placebo-Controlled Study of the Safety, Tolerability, Pharmacokinetics, and Preliminary Efficacy of Single Doses of Compound A in Healthy Volunteers and Subjects with Treatment-Resistant Depression Compound A [(S)-2-amino-5,5-difluoro-4,4-dimethylpentanoic acid] is a novel, orally bioavailable, specific, small molecule that activates mTORC1 pathway signaling in the brain, including those centers responsible for mood. In multiple preclinical rodent models of stress-induced depressive behavior, when compared head-to-head with ketamine, compound A demonstrated rapid antidepressant effects comparable to those of ketamine without producing significant adverse effects. The pharmacological activity of compound A was also found to be comparable to that of ketamine in a nonhuman primate model of anxiolytic/depressive behavioral responses. Lastly, like ketamine, the antidepressant effects of compound A were shown to be dependent on the post-synaptic activation of mTORC1 and were associated with an increase in mTORC1 downstream signaling, synaptic protein expression (e.g., GluR1 and synapsin), and synaptic arborization in layer V pyramidal neurons in the medial pre-frontal cortex of rats. Unlike ketamine, however, the pharmacological efficacy of compound A was not associated with N-methyl-D-aspartate (NMDA) receptor modulation. Taken together, these data demonstrate the antidepressant potential for compound A for the treatment of TRD.

Study Objectives:

Primary Objective: The primary objective of this study was to assess the safety and tolerability of single ascending dosage levels of compound A versus placebo in healthy volunteers and a single dose of compound A versus placebo in subjects with TRD.

Secondary Objectives: Secondary objectives were to assess the pharmacokinetics of compound A in healthy volunteers and subjects with TRD, and to assess the preliminary efficacy of compound A in subjects with TRD.

Study Endpoints:

Safety Endpoints:

safety and tolerability of single ascending dosage levels of compound A vs. placebo in healthy volunteers were assessed safety and tolerability of a single dose of compound A vs. placebo in subjects with TRD were assessed Preliminary Efficacy Endpoints:

Primary Efficacy Endpoint: The primary efficacy endpoint was the difference between the compound A group and the placebo group in change from baseline in the Montgomery Asberg Depression Rating Scale (MADRS) total score at Day 2 (24 hours post dose).

Secondary Efficacy Endpoints: Secondary preliminary efficacy endpoints were the difference between the compound A group and the placebo group in:

change from baseline in the MADRS total score at each time point change from baseline in the Hamilton Depression Rating Scale-6 Item (HAM-D6) total score at each time point change from baseline in the IDS-SR30 total score and domain scores at each time point change from baseline in the Clinical Global Impression-Severity (CGI-S) score at each time point Pharmacokinetic Endpoints:

the pharmacokinetics of compound A in healthy volunteers was assessed the pharmacokinetics of compound A in subjects with TRD was assessed Pharmacodynamic Endpoint (Subjects in Part B Only):

the potential relationships between compound A plasma concentrations and efficacy parameters was assessed Pharmacogenetic Endpoint (Subjects in Part B Only):

the potential relationships between single-nucleotide polymorphism in the BDNF gene (a methionine [Met] substitution for valine [Val] at codon 66; Val66Met) and efficacy parameters were assessed Overall Study Design:

This was a randomized, two-part, double-blind, placebo-controlled study of single ascending dosage levels of compound A in healthy volunteers (Part A) and a single dose of compound A in subjects with TRD (Part B). Subjects were randomized at different study sites, including 48 healthy subjects and 32 subjects with TRD. The duration of each subject's participation was up to 39 days, including screen/washout and follow-up. Total duration for the study is expected to be approximately 12 months.

Overall Design of Part A of the Study (Single-Ascending-Dose [SAD] Portion in Healthy Volunteers): Part A was a randomized, two-part, double-blind, placebo-controlled, single-site study of single ascending dosage levels of compound A in healthy volunteers. The study included an up to 28-day screening period, an in-house period during which compound A or placebo was administered, and a 3- to 7-day follow-up period after discharge. Up to approximately 48 healthy volunteers were randomly assigned to double-blind treatment. Eight (8) subjects were randomized in each of six dosage-level cohorts (150, 300, 600, 1000, 1600, or 2400 mg compound A, or placebo, administered as an oral solution). Within each cohort, six subjects were randomized to receive compound A and two subjects were randomized to receive placebo. Each subject received only one dose of either compound A or placebo on Day 1. Within each cohort, initially one subject received compound A and one subject received placebo. As no clinically significant safety issues were noted in the 24 hours after dosing the initial two subjects in the cohort, the six subjects remaining in the cohort were dosed. The in-house period was 6 days/5 nights. The duration of each subject's participation was up to 39 days, including screen/washout and follow-up.

The chart for Part A of the study is shown in Table 1, and the dose ascension scheme for Part A is shown in FIG. 1.

TABLE 1

| Chart for Part A of the Study (SAD Portion in Healthy Volunteers) | | | | | | |
|---|---|---|---|---|---|---|
| Screening Visit, Days | Residential/In-House Period (6 days/5 nights) | | | | | Follow-Up Visit |
| −28 to −3 | Day −2 | Day −1 | Day 1 | Days 2 and 3 | Day 4 | (Days 7-11) |
| Clinic visit | Admission to study unit | Acclimation, observation | Randomization; single dose of compound A | Observation, assessments | Discharge from study | Clinic visit 5 ± 2 days |

TABLE 1-continued

Chart for Part A of the Study (SAD Portion in Healthy Volunteers)

| Screening Visit, Days | Residential/In-House Period (6 days/5 nights) | | | | | Follow-Up Visit |
|---|---|---|---|---|---|---|
| −28 to −3 | Day −2 | Day −1 | Day 1 | Days 2 and 3 | Day 4 | (Days 7-11) |
| | inclusion/ exclusion | | or placebo (double-blind) | | unit | after discharge |

Overall Design of Part B of the Study (Single-Dose Portion in Subjects with TRD): Part B was a randomized, two-part, double-blind, placebo-controlled, multi-site, single-dose study of compound A in subjects with TRD. The study included an up to 28-day screening period, an in-house period during which compound A or placebo was administered, and a 3- to 7-day follow-up period after discharge. The dosage level for this cohort (2400 mg) was based on the preliminary safety, tolerability, and PK data from Part A of the study. Within this cohort, potential eligibility was confirmed by a site-independent review process. The site-independent review process consisted of a telephone interview with the potential subject (to occur after the subject has passed initial screening and before admission to the clinical unit), and a review of symptom stability (to occur on Day −2).

In Part B of the study, approximately 32 subjects were randomly assigned to double-blind treatment in one cohort. Within this cohort, sixteen (16) subjects were randomized to receive compound A and sixteen (16) subjects were randomized to receive placebo. Each subject received placebo once daily (QD) in a single-blind manner from Day −3 to Day −1, and one dose of either compound A or placebo (double-blind) on Day 1. The single-blind placebo lead-in treatment was intended to facilitate screening out placebo responders.

In Part B of the study, after signing the informed consent, potential subjects discontinued the use of antidepressants at least 14 days prior to dose administration (Day 1). For fluoxetine, a predose washout period of at least 3 weeks for ≤20 mg/day and at least 4 weeks for >20 mg/day was required. Subjects were instructed to contact the site if they experience any adverse events, including worsening of depression, during the screening period.

The in-house period was 8 days/7 nights. The duration of each subject's participation was up to 39 days, including screen/washout and follow-up. The chart for Part B of the study is shown in Table 2, below.

Study Design Rationale:

This study was designed to evaluate the safety, tolerability, PK, and preliminary efficacy of compound A. As this was the first clinical trial of compound A, in Part A of the study, healthy volunteers were enrolled. After the safety, tolerability, and PK of compound A was evaluated in healthy volunteers in Part A of the study, the safety, tolerability, PK, and preliminary efficacy of compound A was evaluated in subjects with TRD in Part B of the study.

Initially, in Part A of the study, single ascending doses were administered and evaluated. To ensure subject safety, a safety review committee (SRC) assessed safety, tolerability, and plasma PK data prior to ascending from one dosage-level cohort to the next-higher dosage-level cohort, and prior to transitioning from Part A of the study to Part B of the study.

The study included standard safety and tolerability assessments—e.g., physical, neurological, and psychiatric examinations, vital signs, oral temperature, respiration rate, weight, 12-lead paper electrocardiograms (pECGs), dECGs, clinical laboratory tests, monitoring of adverse events (AEs) and concomitant medications, and, in Part A of the study, cardiovascular (CV) telemetry and safety EEGs. The study also included safety and tolerability assessments specific for drugs that may have psychiatric effects—e.g., the Columbia-Suicide Severity Rating Scale (C-SSRS; Part B only), the Brief Psychiatric Rating Scale-Positive Symptom Subscale [BPRS (+)], and the Clinician Administered Dissociative States Scale (CADSS).

Frequent PK sampling was included in the study to evaluate single-dose PK. Part B of the study included assessments designed to assess preliminary efficacy.

Dose Selection Rationale:

Human dose selection for compound A was based on nonclinical compound A safety pharmacology, toxicology, and PK findings with compound A, together with human compound A exposure predictions.

TABLE 2

Chart for Part B of the Study (Single-Dose Portion in Subjects with TRD)

| Screening Visit, Days | Residential/In-House Period (8 days/7 nights) | | | | | Follow-Up Visit |
|---|---|---|---|---|---|---|
| −28 to −5 | Day −4 | Day −3 through Day −1 | Day 1 | Days 2 and 3 | Day 4 | (Days 7-11) |
| Clinic visit [a] | Admission to study unit | Inclusion/exclusion; single dose of placebo daily (single-blind) [a] | Randomization; Single dose of compound A or placebo (double-blind) | Observation, assessments | Discharge from study unit | Clinic visit 5 ± 2 days after discharge |

[a] Potential eligibility was confirmed by a site-independent review process. The site-independent review process consisted of a telephone interview with the potential subject (to occur after the subject has passed initial screening and before admission to the clinical unit), and a review of symptom stability (to occur on Day −2).

Factors Influencing Starting and Stopping Dose for compound A: The proposed starting dose of compound A (150 mg) was based on considering the NOAEL dose of compound A in the most sensitive species (160 mg/kg dosed Q3D for 14 days in rat), determining the human equivalent dose (HED) based on the body surface area difference between the two species (~26 mg/kg, or ~1560 mg for a 60 kg human), followed by applying a safety factor of 10 to yield the maximum recommended starting dose (MRSD). Based on the above considerations, the starting dose of compound A in the present study was 150 mg. Based on an integrated assessment of nonclinical findings with compound A, the planned maximum dose for compound A in the first-time-in-humans (FTIH) study was 2400 mg. Extrapolated on the basis of body surface area, the 2400 mg dose is equivalent to 247 mg/kg in rats and 123 mg/kg in monkeys. At a higher dose level in rats (500 mg/kg), effects included lymphoid atrophy and decreased leucocytes. At 160 mg/kg in monkeys, the only effect was a slight decrease in heart rate (approximately 18%, or approximately 30 beats per minute, compared with vehicle). In conclusion, the completed toxicology and safety pharmacology studies supported administration of compound A with a low starting dose of 150 mg, a planned maximum dose of 2400 mg, and careful and comprehensive monitoring.

Control Group Rationale:

Placebo was included to permit comparative assessment of compound A's safety, tolerability, and preliminary efficacy, and to facilitate evaluation of the balance of benefit and risk provided by compound A.

Subject Selection Criteria:
Inclusion Criteria (Subjects in Part A or Part B):
Subjects had to understand the nature of the study and had to provide signed and dated written informed consent before the conduct of any study-related procedures.
Female subjects had to be postmenopausal or surgically sterile or agreed to use one or more of the following forms of contraception from the time of signing the informed consent form through at least 30 days following the administration of test article: hormonal (i.e., oral, transdermal, implant, or injection); double barrier (i.e., condom, diaphragm with spermicide); intrauterine device (IUD); or vasectomized partner (6 months minimum). Postmenopausal women had to have had ≥12 months of spontaneous amenorrhea with follicle-stimulating hormone (FSH) ≥30 mIU/mL. Surgically sterile women were defined as those who have had a hysterectomy, bilateral ovariectomy, or bilateral tubal ligation. All women had to have a negative pregnancy test result before administration of test article.
Male subjects who were biologically capable of having children (i.e., non-vasectomized) had to agree to use one or more of the above forms of birth control for either themselves or their partner(s), as appropriate, from the time of signing the informed consent form through at least 90 days following the administration of test article.
Subjects had to be, in the opinion of the investigator, able to participate in all scheduled evaluations, likely to complete all required tests, and likely to be compliant.
Subjects had to be fluent in English.
Inclusion Criteria (Subjects in Part A Only):
Subjects had to be age 18-55, inclusive.
Subjects had to have a body mass index (BMI) between 19 and 30, inclusive.
Inclusion Criteria (Subjects in Part B Only):
Subjects had to be age 18-65, inclusive.
Subjects had to have a BMI between 19 and 35, inclusive.
Subjects had to have a diagnosis of major depressive disorder (MDD) without psychotic features, according to the *Diagnostic and Statistical Manual of Mental Disorders,* 5$^{th}$ Edition (DSM-5) criteria, based on clinical assessment and confirmed by the Mini International Neuropsychiatric Interview (MINI).
Subjects had to have had an inadequate response to at least one but no more than four antidepressants (stable, adequate dose, at least 6 weeks treatment) in the current episode of depression. The Massachusetts General Hospital Antidepressant Treatment Response Questionnaire (ATRQ) was used to assess antidepressant treatment response. Less than 50% improvement was considered inadequate response.
Subjects had to have a Montgomery-Asberg Depression Rating Scale (MADRS) total score ≥21 at screen and at all evaluations between screen and dose administration (Day 1).
Subjects had to have a Raskin Depression Rating Scale score ≥9 at screen and at all evaluations between screen and dose administration (Day 1).
Subjects had to be willing to discontinue the use of antidepressants at least 2 weeks prior to dose administration (Day 1). For fluoxetine, a predose washout period of at least 3 weeks for ≤20 mg/day and at least 4 weeks for >20 mg/day was required.
Exclusion Criteria: Subjects were not entered into the study if any of the following exclusion criteria were fulfilled:
Exclusion Criteria (Subjects in Part A or Part B):
A positive pregnancy test result or be breastfeeding.
A clinically significant illness (including chronic, persistent, or acute infection), medical/surgical procedure, or trauma within 30 days prior to screen or between screen and dose administration (Day 1).
A history or presence of a clinically significant hepatic, renal, gastrointestinal, cardiovascular, endocrine, respiratory, immunologic, hematologic, dermatologic, or neurologic abnormality.
A history or presence of any disease, condition, or surgery likely to affect drug absorption, distribution, metabolism, or excretion.
A clinically significant abnormality on physical examination, neurological examination, electrocardiogram (ECG), or laboratory evaluations at screen or between screen and dose administration (Day 1).
Alanine aminotransferase (ALT) or aspartate aminotransferase (AST) levels greater than 1.5 times the upper limit of normal (ULN) at screen or between screen and dose administration (Day 1).
Creatine kinase (CK) level greater than 1.5×ULN at screen or between screen and dose administration (Day 1). In addition, any clinically significant CK level (as determined by the investigator) at screen or between screen and dose administration (Day 1) was exclusionary.
Creatinine clearance <60 mL/min, according to the Cockcroft-Gault equation.
Leukocyte or neutrophil counts less than the lower limit of normal (LLN) at screen or between screen and dose administration (Day 1).
A clinically significant vital signs abnormality at screen or between screen and dose administration (Day 1). This included, but was not limited to, the following, in the supine position (after at least 5 minutes supine controlled rest): (a) systolic blood pressure >150 mmHg, (b) diastolic blood pressure >95 mmHg, or (c) heart rate <45 or >85 beats per minute.

A corrected QT interval measurement corrected according to the Fridericia rule (QT$_c$F)>450 msec for men and >470 msec for women during controlled rest at screen or between screen and dose administration (Day 1), or family history of long QT syndrome.

Any clinically significant abnormalities in rhythm, conduction, or morphology of the resting ECG and any abnormalities in the 12-lead ECG that, in the judgement of the investigator, could interfere with the interpretation of QT$_c$ interval changes, including abnormal ST-T-wave morphology or left ventricular hypertrophy.

PR (PQ) interval shortening <120 msec (PR<120 msec but >110 msec was acceptable if there was no evidence of ventricular pre-excitation).

PR (PQ) interval prolongation (>240 msec), intermittent second-degree (Wenckebach block while asleep or in deep rest was not exclusionary) or third-degree atrioventricular block.

Persistent or intermittent complete bundle branch block (BBB), or intraventricular conduction delay (IVCD) with QRS>110 msec. Subjects with QRS>110 msec but <115 msec were acceptable if there was no evidence of ventricular hypertrophy or pre-excitation.

Significant (>10%) weight loss or gain within 30 days prior to screen or between screen and dose administration (Day 1).

A history of seizure.

A history of clinically significant head trauma, including closed head injury with loss of consciousness.

A history of clinically significant symptomatic orthostatic hypotension (i.e., postural syncope).

A history of neuroleptic malignant syndrome.

A history of chronic urinary tract infections.

A history of cancer within 5 years prior to screen or between screen and randomization (with the exception of non-metastatic basal and/or squamous cell carcinoma of the skin), any history of renal cell carcinoma or breast cancer, or a family history of lymphangioleiomyomatosis in association with tuberous sclerosis complex (TSC-LAM).

Any illness or condition that, in the opinion of the investigator, (a) significantly increased the potential risk associated with the subject's participation in the study, (b) decreased the likelihood the subject would complete the study, and/or (c) could confound the results of the study.

A diagnosis of intellectual disability (intellectual developmental disorder) or mental retardation.

Used prescription or nonprescription medications for attention-deficit hyperactivity disorder (ADHD), narcolepsy, or cognitive enhancement (e.g., methylphenidate, atomoxetine, modafinil, *Ginkgo biloba*, and huperzine A) within 1 month prior to screen or between screen and dose administration (Day 1).

Used any vitamin or herbal supplement within 2 weeks prior to dose administration (Day 1), unless approved by the investigator and medical monitor.

Consumed alcohol or used any over-the-counter medication (other than up to 3 g per day paracetamol/acetaminophen) within 7 days prior to screen or between screen and dose administration (Day 1).

Regularly consumed (e.g., more days than not) excessive quantities of xanthine-containing beverages (e.g., more than five cups of coffee or the equivalent per day) within 30 days prior to screen or between screen and dose administration (Day 1).

Donated blood or plasma within 6 weeks prior to screen or between screen and dose administration (Day 1).

Used any experimental medication, device, or biologic within 3 months or five half-lives (whichever was longer) prior to dose administration (Day 1).

Was currently employed by Navitor Pharmaceuticals, Inc. or by a clinical trial site participating in this study, or a first-degree relative of a Navitor Pharmaceuticals, Inc. employee or of an employee at a participating clinical trial site.

Any condition that, in the opinion of the investigator or medical monitor, made the subject unsuitable for the study.

Strenuous physical activity within 1 week prior to dose administration (Day 1).

Unsatisfactory venous access.

Known or suspected hypersensitivity or idiosyncratic reaction to study drug or study drug excipients.

Exclusion Criteria (Subjects in Part A Only):

A clinically significant abnormality on EEG at screen (e.g., epileptiform activity).

Urine drug screen positive for a drug of abuse.

Used any prescription drug (other than hormonal contraceptive) within 2 weeks prior to screen, or between screen and dose administration (Day 1).

Frequently used any tobacco-containing (e.g., cigar, cigarette, or snuff) or nicotine-containing product (e.g., nicotine chewing gum, nicotine plasters, or other product used for smoking cessation) within 3 months prior to screen. Frequent use is defined as 3 or more days per week. Use of any tobacco- or nicotine-containing product was prohibited within 1 week of dose administration (Day 1).

Any history of psychiatric disorders, including substance use disorders, according to the DSM-5 criteria.

Exclusion Criteria (Subjects in Part B Only):

Urine drug screen positive for a drug of abuse, except *Cannabis*. Prior use of *Cannabis* was permitted provided the subject agreed to abstain from smoking or ingesting *Cannabis* within 1 week of dose administration (Day 1) and during the study (including the follow-up period), and provided that in the judgement of the investigator, the subject was likely to be compliant regarding this restriction.

Used any psychopharmacologic drug (including antidepressants) within 2 weeks prior to dose administration (Day 1), except for sleep medication, if used less than 4 days/week within 1 month prior to screen and between screen and dose administration (Day 1). For fluoxetine, a predose washout period of at least 3 weeks for ≤20 mg/day and at least 4 weeks for >20 mg/day was required.

Any history of a psychotic disorder, MDD with psychosis, bipolar or related disorders, post-traumatic stress disorder, obsessive-compulsive disorder (if primary), intellectual disability (DSM-5 diagnostic code 319), borderline personality disorder, antisocial personality disorder, histrionic personality disorder, or narcissistic personality disorder, according to the DSM-5 criteria, or any other psychiatric or neurologic disorder or symptom that could pose undue risk to the subject or compromise the study.

Moderate or severe substance use disorder within 1 year prior to screen, according to the DSM-5 criteria.

Acute suicidality as evidenced by answering "yes" for Question 4 ("In the Past Year") or Question 5 ("In the Past Year") on the C-SSRS, indicating active suicidal ideation with any intent to act, at screen or between screen and dose administration (Day 1).

History of suicidal behavior such that a determination of "yes" is made on the Suicidal Behavior section of the C-SSRS ("In the Past Year") for "Actual Attempt," "Interrupted Attempt," "Aborted Attempt," or "Preparatory Acts or Behavior."

MADRS item 10 score of 5 at screen or between screen and dose administration (Day 1).

MADRS total score change >25% from Day −4 (admission) to baseline (Day 1, predose).

Covi Anxiety scale score ≥Raskin Depression Rating Scale score at screen or between screen and dose administration (Day 1).

History of clinically significant physical, sexual, or psychological abuse (age ≤7 years).

Determined to be ineligible by site-independent review.

Study Conduct:

Concomitant Treatment and Study Restrictions (Subjects in Part A Only)

Prohibited during the study and during the indicated periods:

Frequent use of any tobacco- or nicotine-containing product within 3 months prior to screen, and any use of any tobacco- or nicotine-containing product within 1 week prior to dose administration (Day 1).

Any experimental medication, device, or biologic within 3 months or five half-lives (whichever is longer) prior to dose administration (Day 1).

Any prescription or nonprescription medication for ADHD, narcolepsy, or cognitive enhancement (e.g., methylphenidate, atomoxetine, modafinil, *Ginkgo biloba*, and huperzine A) within 1 month prior to screen or between screen and dose administration (Day 1).

Any vitamin or herbal supplement within 2 weeks prior to dose administration (Day 1), unless approved by the investigator and medical monitor.

Any prescription drug (other than hormonal contraceptive) within 2 weeks prior to screen or between screen and dose administration (Day 1).

Alcohol or any over-the-counter medication (other than up to 3 g paracetamol/acetaminophen per day) within 7 days prior to screen or between screen and dose administration (Day 1).

Concomitant Treatment and Study Restrictions (Subjects in Part B Only)

Prohibited during the study and during the indicated periods:

Any experimental medication, device, or biologic within 3 months or five half-lives (whichever is longer) prior to dose administration (Day 1).

Any prescription or nonprescription medication for ADHD, narcolepsy, or cognitive enhancement (e.g., methylphenidate, atomoxetine, modafinil, *Ginkgo biloba*, and huperzine A) within 1 month prior to screen or between screen and dose administration (Day 1).

Any vitamin or herbal supplement within 2 weeks prior to dose administration (Day 1), unless approved by the investigator and medical monitor.

Any psychopharmacologic drug (including antidepressants) within 2 weeks of dose administration (Day 1), except for sleep medication, if used less than 4 days/week within 1 month prior to screen and between screen and dose administration (Day 1). For fluoxetine, a predose washout period of at least 3 weeks for ≤20 mg/day and at least 4 weeks for >20 mg/day was required. Sleep medication could be used during the study, but should not have been administered more than 3 days/week, and should not have been administered on Day −1 or Day 1 if possible. The investigator should have contacted the medical monitor prior to administering sleep medication to discuss the intended treatment.

Alcohol or any over-the-counter medication (other than up to 3 g paracetamol/acetaminophen per day) within 7 days prior to screen or between screen and dose administration (Day 1).

Treatments:

Compound A was provided as powder in bottles to be compounded by the site pharmacist or other appropriately qualified staff member, according to local regulations. For the compound A oral solution, the compounded materials consisted of compound A (20-50 mg/g; this represents milligrams of compound A per gram of total solution weight), USP purified water (70%), and FlavorSweet-SF™ (a flavor-masking agent; 30%). The placebo oral solution contained USP purified water (70%) and Flavor Sweet-SF™ (30%). To maintain the double-blind requirements, the placebo volume administered was equivalent to the compound A volume administered for each dosing. The identity of the investigational products is presented in Table 3, below.

TABLE 3

Identity of Investigational Product

| Investigational Product | Dosage Form and Strength | Manufacturer of Active Ingredient |
| --- | --- | --- |
| Compound A | Oral solution: 20-50 mg/g [a] | Aptuit, Verona, Italy |
| Placebo | Matching oral solution | [No active ingredient] |

[a] This represents milligrams of compound A per gram of total solution weight.

Doses and Treatment Regimens:

Part A of the study (SAD portion in healthy volunteers):

Subjects randomized to receive compound A: A single fixed dose of 150, 300, 600, 1000, 1600, or 2400 mg compound A was administered orally as a solution on Day 1. Subjects were required to abstain from eating or drinking for two hours prior to and after dosing.

Subjects randomized to receive placebo (purified water and Flavor Sweet-SF™): Single dose placebo was administered orally as a solution on Day 1. Subjects were required to abstain from eating or drinking for two hours prior to and after dosing.

Part B of the study (single-dose portion in subjects with TRD):

Subjects randomized to receive compound A: Each subject received placebo QD in a single-blind manner from Day −3 to Day −1, and a single fixed dose of 2400 mg compound A on Day 1. Compound A and placebo were administered orally as a solution. The compound A dosage level (2400 mg) was based on the safety, tolerability, and PK data from Part A of the study.

Subjects randomized to receive placebo (purified water and Flavor Sweet-SF™): Each subject received placebo QD in a single-blind manner from Day −3 to Day −1, and a single dose of placebo on Day 1. Placebo was administered orally as a solution.

Collection of Study Variables:

The following were assessed for each patient, unless otherwise specified:

1. ECG
2. Respiration rate and oral temperature
3. Blood pressure and pulse rate
4. PK blood sample
5. EEG (Part A only)
6. Clinical laboratory safety samples
7. Neurological and physical examinations
8. Psychiatric assessment Definition of Adverse Events (AEs), Treatment-Emergent AEs (TEAEs), and Adverse Drug Reactions (ADRs)

An AE is any unfavorable and unintended sign (including an abnormal laboratory finding), symptom, or disease temporally associated with the use of a medical treatment or procedure, whether or not considered related to the medical treatment or procedure. In clinical studies, an AE can include an undesirable medical condition occurring at any time, including run-in or washout periods, even if no study treatment has been administered. An AE term is a unique representation of a specific event used for medical documentation and scientific analyses.

A TEAE is an AE that either commenced following initiation of study treatment or was present prior to study treatment but increased in frequency or severity following initiation of study treatment.

An adverse drug reaction (ADR) is any AE considered related to any dose of a medicinal product—that is, a causal relationship between the medicinal product and the AE is at least a reasonable possibility (the relationship cannot be ruled out).

Definitions of Serious Adverse Events (SAEs): A serious adverse event (SAE) is an AE occurring during any study phase (i.e., run-in, treatment, washout, or follow-up) that fulfills one or more of the following criteria:

Results in death

Is immediately life-threatening

Requires in-patient hospitalization or prolongation of existing hospitalization

Results in persistent or significant disability/incapacity or substantial disruption of the ability to conduct normal life functions Is a congenital abnormality or birth defect Is an important medical event that may jeopardize the subject or may require medical intervention to prevent one of the outcomes listed above Psychiatric Evaluations:

Brief Psychiatric Rating Scale-Positive Symptom Subscale [BPRS (+)]: The BPRS (+) is a clinician-administered scale used to measure psychotic behaviors not generally seen in healthy people ("positive" symptoms). The scale includes 4 items, each scored on a scale of 1 to 7.

Clinician Administered Dissociative States Scale (CADSS): The CADSS is a clinician-administered instrument used to measure present-state dissociative symptoms. It consists of 23 items, all rated on a 0-4 scale. It has three factors that assess symptoms of amnesia, depersonalization, and derealization.

Columbia-Suicide Severity Rating Scale (C-SSRS): The C-SSRS is a unique, simple, and short method of assessing both behavior and ideation that tracks all suicidal events and provides a summary of suicidality. It assesses the lethality of attempts and other features of ideation (frequency, duration, controllability, reasons for ideation, and deterrents), all of which are significantly predictive of completed suicide. The C-SSRS was performed at screen, on each day of confinement at the study site, and at the follow-up visit to determine the presence of suicidality.

Childhood Trauma Questionnaire-Short Form (CTQ-SF): The CTQ-SF is a self-administered inventory used to assess a broad range of maltreatment experiences. The CTQ-SF, which includes 28 items (25 clinical items and three validity items) scored on a scale of 1 to 5, is derived from a longer (78-item) questionnaire.

Covi Anxiety and Raskin Depression Scales (Covi-Raskin): The Covi Anxiety and Raskin Depression scales are clinician-administered scales used to assess overall levels of anxiety and depression. Each scale includes 3 items, each scored 1 to 5.

Preliminary Efficacy Evaluations: Other psychiatric evaluations were performed to assess preliminary efficacy in Part B only. These evaluations included the Montgomery-Asberg Depression Rating Scale (MADRS), the Hamilton Depression Rating Scale-6 Item (HAM-D6), the Clinical Global Impression-Severity (CGI-S), and the Inventory of Depressive Symptomatology (30-item, self-rated version) (IDS-SRN). Montgomery-Asberg Depression Rating Scale (MADRS).

The MADRS is a clinician-administered scale used to assess the range of symptoms that are most frequently observed in patients with major depression. The scale includes 10 items, each scored on a scale of 0 to 6. The MADRS was administered centrally by a third-party independent rater blinded to protocol, visit, and treatment.

Hamilton Depression Rating Scale-6 Item (HAM-D6): The HAM-$D_6$ is a clinician-administered scale used to assess key domains of depressive symptomatology. The HAM-$D_6$ was derived from the original 17-item version of the scale (HAM-$D_{17}$). Five of the six items are scored on a scale of 0 to 4, and one item is scored on a scale of 0 to 2.

Clinical Global Impression-Severity (CGI-S): The CGI-S is a 7-point clinician-administered scale used to assess the severity of the patient's illness at the time of assessment relative to the clinician's past experience with patients who have the same diagnosis.

Inventory of Depressive Symptomatology (30-Item, Self-Rated Version) (IDS-$SR_{30}$): The IDS-$SR_{30}$ is a self-rated scale used to assess the severity of depressive symptomatology. The scale includes 30 items, each scored on a scale of 0 to 3.

Study Results

Disposition: 48 randomized subjects; 6 drug groups (n=36 total) and 1 placebo group (n=12). All subjects completed the study.

Part A—Safety: Compound A: Compound A was well tolerated, with no serious adverse events, and no discontinuations due to adverse events. All adverse events were mild and typical of Phase 1 studies. A maximally tolerated dose was not reached. Vitals, labs, and ECG findings were unremarkable. BPRS+ and CADSS scores were comparable as between the treatment groups. TEAE data are provided for each cohort in Table 4, below.

TABLE 4

| Preferred Term | Compound A 150 mg N = 6 n (%) | 300 mg N = 6 n (%) | 600 mg N = 6 n (%) | 1000 mg N = 6 n (%) | 1600 mg N = 6 n (%) | 2400 mg N = 6 n (%) | Total N = 36 n (%) | Placebo Total N = 12 n (%) |
|---|---|---|---|---|---|---|---|---|
| Total number of TEAEs | 3 | 2 | 1 | 1 | 10 | 5 | 22 | 2 |
| Number of subjects with ≥1 TEAE | 2 (33.3) | 2 (33.3) | 1 (16.7) | 1 (16.7) | 4 (66.7) | 3 (50.0) | 13 (36.1) | 2 (16.7) |
| Nausea | — | — | — | — | 1 | 2 | 3 | — |
| Abdominal pain | — | — | — | — | 1 | — | 1 | — |
| Abdominal pain lower | 1 | | — | | | | 1 | — |
| Diarrhea | — | — | — | — | 1 | — | 1 | — |
| Dry mouth | — | — | — | — | 1 | — | 1 | — |
| Vomiting | — | — | — | — | — | 1 | 1 | — |
| Dermatitis contact | — | — | — | — | 2 | 1 | 3 | — |
| Tonsillitis | — | — | — | — | — | — | — | 1 |
| Blood creatine phosphokinase increased | — | 1 | — | — | — | — | 1 | — |
| Lipase increased | — | 1 | — | — | — | — | 1 | — |
| Neutrophil count decreased | — | — | — | — | — | — | — | 1 |
| Dizziness | 1 | — | 1 | 1 | 2 | — | 4 | — |
| Headache | — | — | — | — | 1 | 1 | 2 | — |
| Presyncope | — | — | 1 | — | — | — | 1 | — |
| Somnolence | — | — | — | — | 1 | — | 1 | — |
| Hot flush | — | — | — | — | — | — | 1 | — |

Disposition: 40 planned subjects; study finalized with 32 subjects randomized, of which 31 were included in the efficacy sample. See Table 5, below.

TABLE 5

| Category | Compound A 2400 mg n (%) | Placebo n (%) | Total n (%) |
|---|---|---|---|
| Screened | | | 93 |
| Screen failures | | | 61 |
| Rescreened | | | 1 |
| Randomized | 16 (100) | 16 (100) | 32 (100) |
| Safety set | 16 | 16 | 32 |
| Efficacy set | 16 | 15 | 31 |
| Completed 4 days in unit | 16 (100) | 16 (100) | 16 (100) |
| Completed follow-up visit | 16 (100) | 15 (93.8) | 31 (96.9) |

Part B—Patient demographics in the ITT (Intention to Treat) population: See Table 6, below.

TABLE 6

| Category | Compound A 2400 mg n = 16 | PBO N = 16 | Total N = 32 |
|---|---|---|---|
| Age - mean (SD) | 50.4 (10.8) | 54.6 (6.4) | 52.5 (9.0) |
| Female (%) | 7 (43.8) | 5 (31.3) | 12 (37.5) |
| Race | | | |
| White | 10 (62.5) | 10 (62.5) | 20 (62.5) |
| Black or AA | 6 (37.5) | 6 (37.5) | 12 (37.5) |
| Weight (mean kg) | 85.5 | 83.9 | 84.7 |
| BMI | 29.7 | 28.3 | 29.0 |
| BPRS (+) score | 4.0 | 4.0 | 4.0 |
| CADSS score | 0.3 | 0.3 | 0.3 |

TABLE 6-continued

| Category | Compound A 2400 mg n = 16 | PBO N = 16 | Total N = 32 |
|---|---|---|---|
| BDNF genotype (V66M) | 11 VV/ 5 VM/ 0 MM | 12 VV/ 4 VM/ 0 MM | 23 VV/ 9 VM/ 0 MM |
| MADRS total score | 34.7 (5.3) | 36.8 (5.2) | 35.7 (5.3) |
| HAM-D6 total score | 12.3 (2.6) | 12.6 (2.7) | 12.5 (2.6) |
| IDS-SR total score | 39.1 (7.9) | 38.9 (11.6) | 39.0 (9.7) |
| CGI-S score | 4.4 (0.5) | 4.6 (0.5) | 4.5 (0.5) |
| C-SSRS | | | |
| Lifetime | 3 (18.8) | 3 (18.8) | 6 (18.8) |
| Past 12 months | 1 (6.3) | 2 (12.5) | 3 (9.4) |

Part B—Safety: Compound A: Compound A was well tolerated, with no serious adverse events, and no discontinuations due to adverse events. All adverse events were mild-moderate. Vitals, labs, and ECG findings were unremarkable. BPRS+ and CADSS scores were comparable as between the treatment groups. A safety summary is provided in Table 7, below, and TEAE data are provided in Table 8, below.

TABLE 7

Safety Summary

| TEAE Category | Compound A n = 16 | PBO n = 16 |
|---|---|---|
| Total number of TEAES | 24 | 6 |
| Subjects with at least 1 AE | 11 (68.8) | 6 (37.5) |
| Discontinuations due to AE | 0 | 0 |
| Serious AEs | 0 | 0 |
| Deaths | 0 | 0 |

TABLE 8

Treatment Emergent Adverse Events

| Preferred Term | Compound A n = 16 | PBO n = 16 |
|---|---|---|
| Somnolence | 4 | 2 |
| Headache | 2 | 1 |
| Dizziness | 2 | — |
| Dizziness postural | 1 | — |
| Sensory disturbance | 1 | — |
| Hyperthyroidism | 1 | — |
| Dry mouth | 1 | — |
| Dyspepsia | 1 | — |
| Flatulence | 1 | — |
| Frequent bowel movements | 1 | — |
| Nausea | 1 | — |
| Feeling abnormal | 1 | — |
| Upper respiratory infection | — | 1 |
| Skin abrasion | 1 | — |
| T-wave inversion | 1 | — |
| Blood pressure increased | — | 1 |
| Increased appetite | — | 1 |
| Back pain | 1 | — |
| Myalgia | 1 | — |
| Nipple pain | 1 | — |
| Hypertension | 1 | — |
| Orthostatic hypotension | 1 | — |

Table 9, below, depicts the timing of the efficacy assessments. The MADRS total score was centrally administered. The HAM-D6 was site-administered. The CGI-S was site physician administered. The IDS-SR was patient self-administered. MADRS-6 and MADRS-8 scores were then extrapolated post hoc from the MADRS total scores.

TABLE 9

| | Pre-dose | Dose | 2 h | 4 h | 8 h | 12 h | 24 h | 36 h | 48 h | 72 h |
|---|---|---|---|---|---|---|---|---|---|---|
| MADRS, CGI-S, IDS-SR | X | | | | | | X | | X | X |
| HAM-D6 | X | | X | X | X | X | X | X | X | X |

MADRS-10 items include apparent sadness, reported sadness, inner tension, reduced sleep, reduced appetite, concentration difficulties, lassitude, inability to feel, pessimistic thoughts, and suicidal thoughts. MADRS-6 items include apparent sadness, reported sadness, inner tension, lassitude, inability to feel, and pessimistic thoughts. MADRS-8 items include apparent sadness, reported sadness, inner tension, concentration difficulties, lassitude, inability to feel, pessimistic thoughts, and suicidal thoughts. HAM-D6 items include depressed mood, low self-esteem/guilt, work and interests, psychomotor retardation, psychic anxiety, and somatic symptoms.

When determining clinically significant antidepressant effect, it is recommended to use standardized effect size statistics. The correct use of depression rating scales in clinical trials of antidepressants is to indicate the effect size of the specific items of depression and to accept an effect size of 0.40 or higher as being the clinically significant effect. Effect sizes for the present study are shown in Table 10, below. An effect size of ≥0.2 indicates early improvement. An effect size of ≥0.4 indicates a clinical response.

TABLE 10

| Scale | 2 h | 4 h | 8 h | 12 h | 24 h | 36 h | 48 h | 72 h |
|---|---|---|---|---|---|---|---|---|
| PRESPECIFIED ANALYSES (N = 31) | | | | | | | | |
| MADRS Total Score (prelim. primary @24 h) | | | | | 0.1 | | 0.2 | -0.1 |
| HAM-D6 | 0.6 | 0.8 | 0.7 | 0.8 | 0.5 | 0.5 | 0.5 | 0.4 |
| IDS-SR 30 Total Score | | | | | 0.3 | | 0.3 | 0.3 |
| CGI-S Change from baseline | | | | | -0.1 | | 0.1 | 0.2 |
| SELECT POST-HOC ANALYSES | | | | | | | | |
| MADRS-06 (core), N = 31 | | | | | 0.3 | | 0.3 | 0.1 |
| MADRS-08 (core-plus), N = 31 | | | | | 0.3 | | 0.3 | 0.1 |
| IDS-SR Psychomotor Domain, N = 31 | | | | | 0.8 | | 0.3 | 0.6 |

Efficacy signals for younger and more severely depressed patients as measured at baseline are shown in Table 11, below.

TABLE 11

| Scale | 2 h | 4 h | 8 h | 12 h | 24 h | 36 h | 48 h | 72 h |
|---|---|---|---|---|---|---|---|---|
| Select Post-hoc Analyses | | | | | | | | |
| MADRS Total for ≤55 years old, N = 14 | | | | | 0.6 | | 0.6 | 0.3 |
| HAM-D6 for ≤55 years old, N = 14 | 0.8 | 1.0 | 1.1 | 1.3 | 0.9 | 1.3 | 1.2 | 1.1 |
| CGI-S for ≤55 years old, N = 14 | | | | | 0.2 | | 0.4 | 0.2 |
| MADRS Total for ≥36 MADRS at baseline, N = 16 | | | | | 0.4 | | 0.3 | 0.3 |
| HAM-D6 for ≥36 MADRS at baseline, N = 16 | 1.0 | 1.1 | 0.8 | 0.9 | 0.8 | 0.9 | 0.9 | 0.8 |
| CGI-S for ≥36 MADRS at baseline, N = 16 | | | | | 0.2 | | 0.7 | 1.0 |

Figure 2:
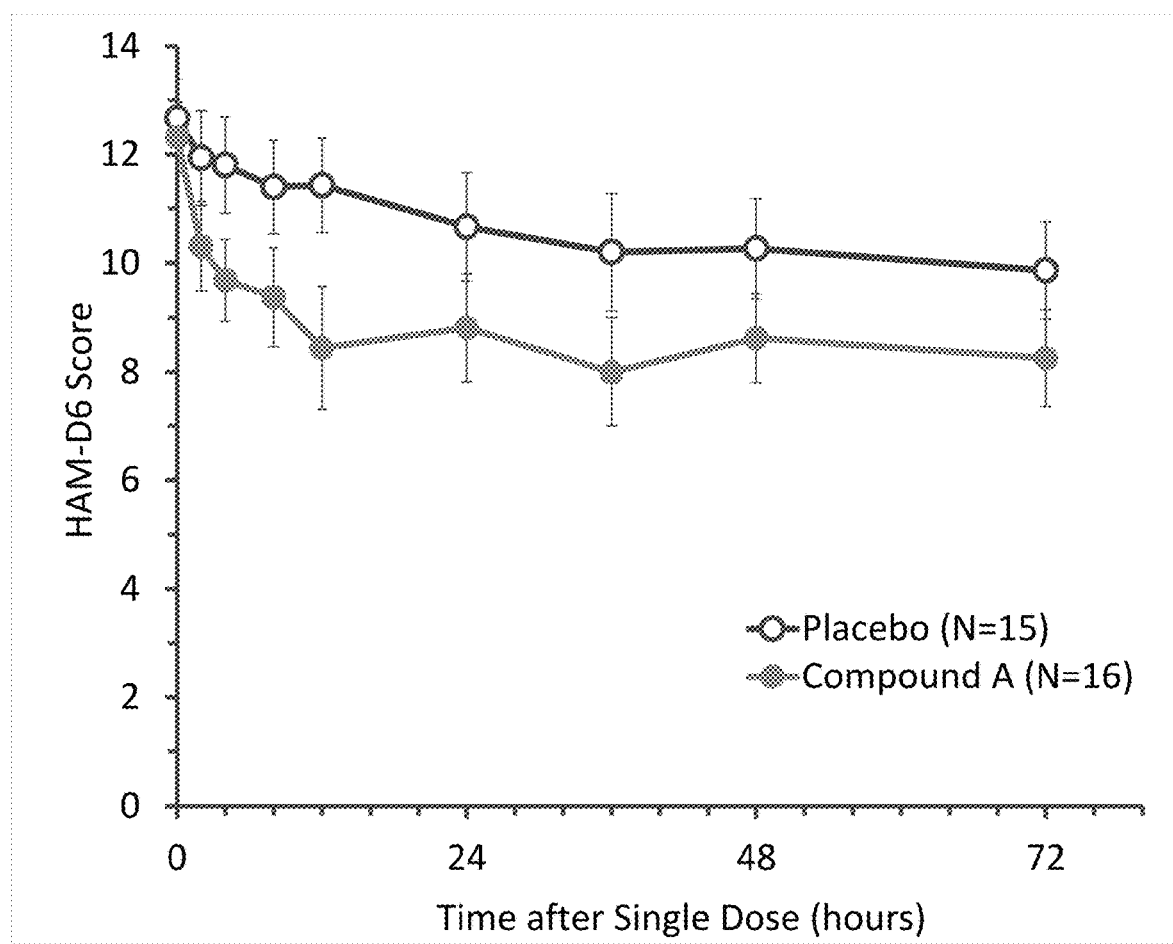
FIG. 2 depicts the HAM-D6 scores showing rapid and sustained efficacy with a single dose of compound A.

FIG. 2 depicts the HAM-D6 scores showing rapid and sustained efficacy with a single dose of compound A. Efficacy was observed as early as two hours post-dose, with numerical benefits continuing for up to 24-72 hours. Table 12 outlines the effect size at each time interval.

TABLE 12

| Change in HAM-D6 | Compound A | Placebo | Difference | P-Value | Effect Size |
|---|---|---|---|---|---|
| Total Score at 2 h | -2.0 | -0.7 | -1.3 | 0.066 | 0.6 |
| Total Score at 4 h | -2.6 | -0.9 | -1.8 | 0.017 | 0.8 |
| Total Score at 8 h | -2.9 | -1.3 | -1.7 | 0.051 | 0.7 |

TABLE 12-continued

| Change in HAM-D6 | Compound A | Placebo | Difference | P-Value | Effect Size |
|---|---|---|---|---|---|
| Total Score at 12 h | −3.9 | −1.1 | −2.7 | 0.020 | 0.8 |
| Total Score at 24 h | −3.5 | −2.0 | −1.5 | 0.172 | 0.5 |
| Total Score at 36 h | −4.3 | −2.5 | −1.8 | 0.145 | 0.5 |
| Total Score at 48 h | −3.7 | −2.4 | −1.3 | 0.135 | 0.5 |
| Total Score at 72 h | −4.1 | −2.8 | −1.3 | 0.214 | 0.4 |

Figure 3:
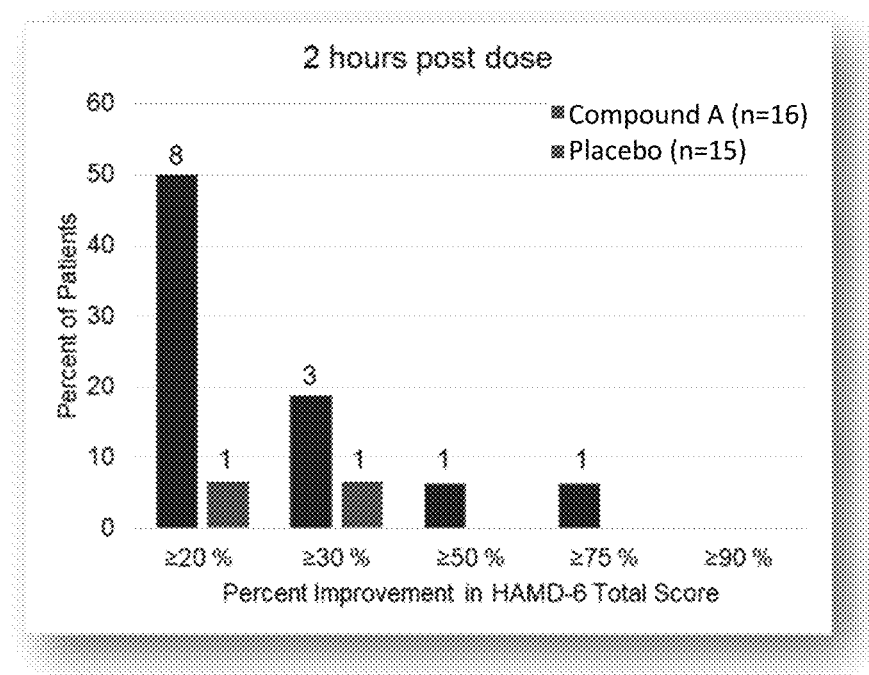
FIG. 3 depicts compound A response rates at 2 hours post dose as measured by HAM-D6.
Figure 4:
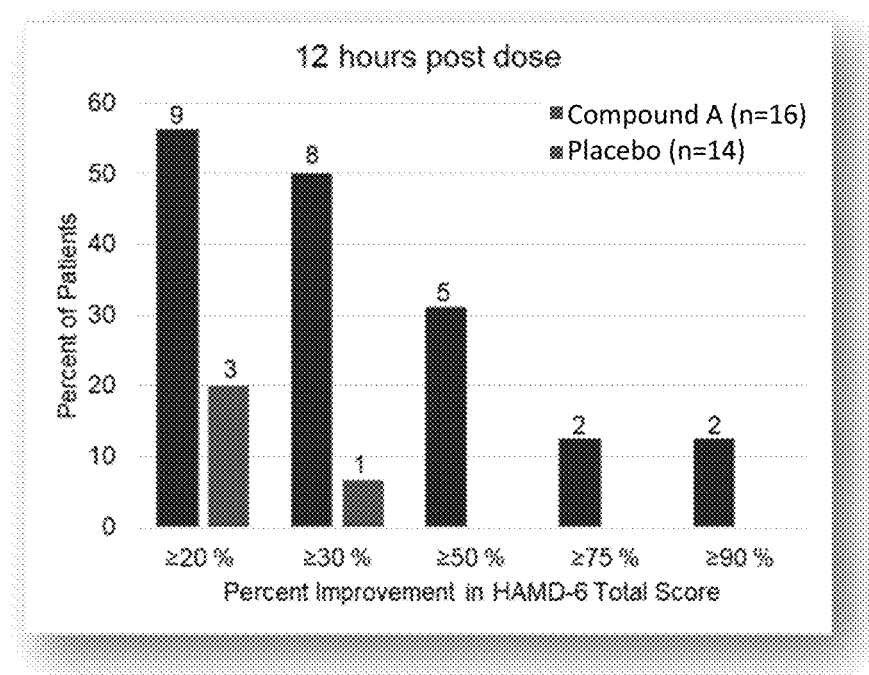
FIG. 4 depicts compound A response rates at 12 hours post dose as measured by HAM-D6.
Figure 5:
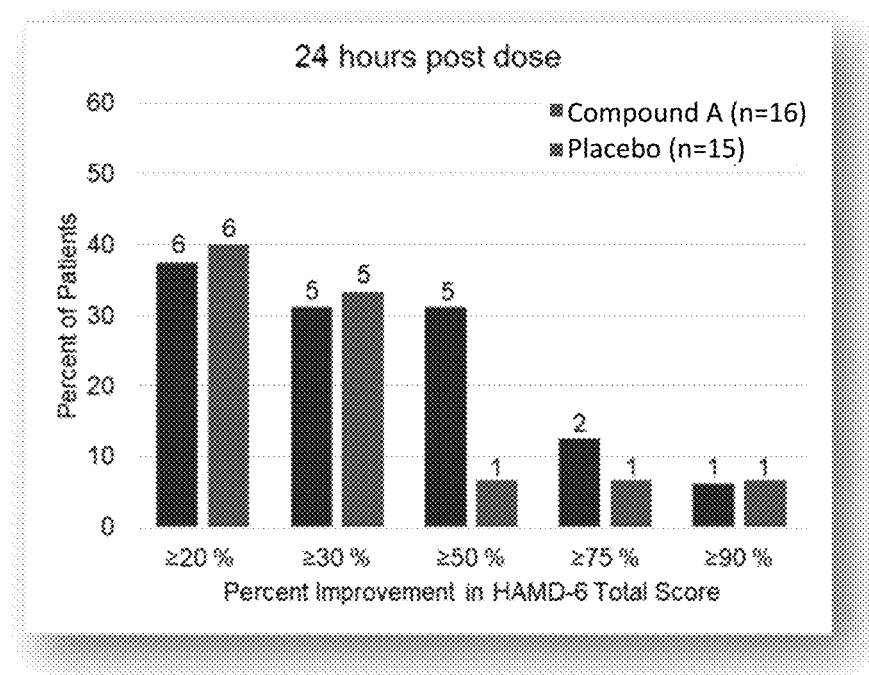
FIG. 5 depicts compound A response rates at 24 hours post dose as measured by HAM-D6.

FIG. 3 depicts compound A response rates at 2 hours post dose as measured by HAM-D6. FIG. 4 depicts compound A response rates at 12 hours post dose as measured by HAM-D6. FIG. 5 depicts compound A response rates at 24 hours post dose as measured by HAM-D6.

Figure 6:
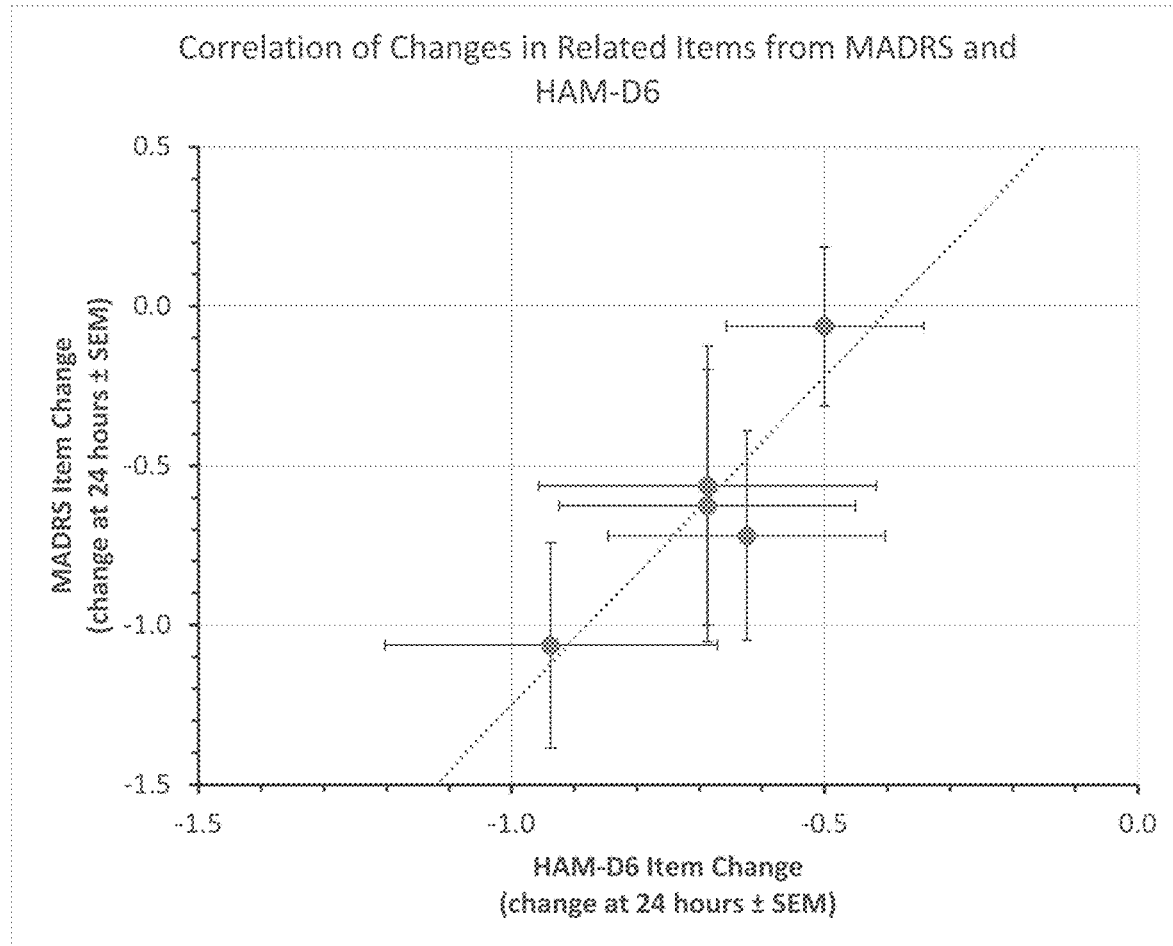
FIG. 6 depicts the correlation between HAM-D6 and MADRS scales in measuring core symptoms of depression.

Five of six items in the HAM-D6 address the same symptoms in a similar or overlapping manner as the MADRS. For the five items in common, changes in the HAM-D6 item scores correlated well with changes in the MADRS item scores in subjects treated with compound A. See Table 13, below, for common items as between scales, and FIG. 6, depicting the correlation between HAM-D6 and MADRS scales in measuring core symptoms of depression.

TABLE 13

| Domain | HAM-D6 Item (0-4)* | MADRS Item (0-6) |
|---|---|---|
| Anxiety | Psychic anxiety | Inner tension |
| Energy | Psychomotor retardation | Lassitude |
| Depression | Depressed mood | Reported + apparent sadness |
| Loss of Interest | Work and interests | Inability to feel |
| Esteem/Guilt | Low self esteem | Pessimistic thoughts |

*Somatic Symptoms, general (HAM-D6 item 6) has no correlate in the MADRS

Table 14, below, provides MADRS item scores at 24 hours post dose. MADRS-6 items are indicated with a double asterisk (**). Compound A showed marked improvement on concentration scores despite having substantially lower baseline scores. Placebo subjects had more severe symptoms overall.

TABLE 14

| MADRS-10 Item | Compound A | | | | Placebo | | | |
|---|---|---|---|---|---|---|---|---|
| | Baseline | Day 1 | CFB | % CFB | Baseline | Day 1 | CFB | % CFB |
| TOTAL SCORE | 34.7 (5.3) | | −5.5 | | 37.1 (5.2) | | −4.8 | |
| Reported Sadness** | 4.88 | 3.94 | −0.94 | −19.2% | 4.73 | 4.27 | −0.47 | −9.9% |
| Apparent Sadness** | 4.56 | 4.00 | −0.56 | −12.3% | 4.53 | 4.13 | −0.40 | −8.8% |
| Inner Tension** | 2.63 | 1.56 | −1.06 | −40.5% | 2.80 | 2.20 | −0.60 | −21.4% |
| Reduced Sleep | 4.25 | 3.94 | −0.31 | −7.4% | 4.27 | 3.60 | −0.67 | −15.6% |
| Reduced Appetite | 3.06 | 2.63 | −0.44 | −14.3% | 4.20 | 3.33 | −0.87 | −20.6% |
| Concentration | 4.06 | 3.13 | −0.94 | −23.1% | 4.60 | 4.13 | −0.47 | −10.1% |
| Lassitude** | 3.50 | 3.44 | −0.06 | −1.8% | 4.33 | 3.73 | −0.60 | −13.9% |
| Inability to Feel** | 4.38 | 3.81 | −0.56 | −12.9% | 4.20 | 3.93 | −0.27 | −6.4% |
| Pessimistic Thoughts** | 2.69 | 2.06 | −0.63 | −23.3% | 2.87 | 2.60 | −0.27 | −9.3% |
| Suicidal Thoughts | 0.69 | 0.63 | −0.06 | −9.1% | 0.53 | 0.40 | −0.13 | −25.0% |

Table 15, below, contains efficacy signal data observed for compound A on several MADRS items associated with core symptoms of depression. MADRS-6 items are indicated with a double asterisk (**).

TABLE 15

| MADRS-10 Item | Compound A | | | | Placebo | | | |
|---|---|---|---|---|---|---|---|---|
| | Baseline | Day 1 | CFB | % CFB | Baseline | Day 1 | CFB | % CFB |
| TOTAL SCORE | 34.7 (5.3) | | −5.5 | | 37.1 (5.2) | | −4.8 | |
| Reported Sadness** | 4.88 | 3.94 | −0.94 | −19.2% | 4.73 | 4.27 | −0.47 | −9.9% |
| Apparent Sadness** | 4.56 | 4.00 | −0.56 | −12.3% | 4.53 | 4.13 | −0.40 | −8.8% |
| Inner Tension** | 2.63 | 1.56 | −1.06 | −40.5% | 2.80 | 2.20 | −0.60 | −21.4% |
| Reduced Sleep | 4.25 | 3.94 | −0.31 | −7.4% | 4.27 | 3.60 | −0.67 | −15.6% |

TABLE 15-continued

|  | Compound A | | | | Placebo | | | |
| --- | --- | --- | --- | --- | --- | --- | --- | --- |
| MADRS-10 Item | Baseline | Day 1 | CFB | % CFB | Baseline | Day 1 | CFB | % CFB |
| Reduced Appetite | 3.06 | 2.63 | −0.44 | −14.3% | 4.20 | 3.33 | −0.87 | −20.6% |
| Concentration | 4.06 | 3.13 | −0.94 | −23.1% | 4.60 | 4.13 | −0.47 | −10.1% |
| Lassitude** | 3.50 | 3.44 | −0.06 | −1.8% | 4.33 | 3.73 | −0.60 | −13.9% |
| Inability to Feel** | 4.38 | 3.81 | −0.56 | −12.9% | 4.20 | 3.93 | −0.27 | −6.4% |
| Pessimistic Thoughts** | 2.69 | 2.06 | −0.63 | −23.3% | 2.87 | 2.60 | −0.27 | −9.3% |
| Suicidal Thoughts | 0.69 | 0.63 | −0.06 | −9.1% | 0.53 | 0.40 | −0.13 | −25.0% |

Compound A was found to have a greater impact than placebo on inner tension, concentration, pessimistic thoughts, and inability to feel.

Example 2. A Randomized, Double-Blind, Placebo-Controlled, Single-Dose Pharmacokinetic Study of Oral Compound A in Plasma and Cerebrospinal Fluid in Healthy Male Volunteers The blood brain barrier restricts the flow of not only proteins to and from the brain but also that of many small molecular substances. Approximately 150 mL CSF is in direct contact with the extracellular space of the brain. Systemically administered drugs can reach the central nervous system (CNS) either by direct passage across the choroid plexus or by indirect passage across blood-brain barrier. Once across these barriers, the drug will diffuse through the interstitial fluid towards the CSF. When the drug reaches the CSF, it is transported throughout the CNS by convection through the ventricular system. Upon exiting the fourth ventricle, the drug then flows through the cerebellomedullary cistern down the spinal cord and over the cerebral hemispheres. Because CSF is in direct contact with the brain tissue, it is assumed to readily equilibrate with brain interstitial fluid concentration. CSF has been used as a useful surrogate for in vivo assessment of CNS exposure in clinical pharmacology studies.

While seizures have not been observed in nonclinical studies with compound A, to mitigate the potential risk of seizure, subjects with a history of seizure were excluded from the present clinical study.

NMDA antagonists, in particular ketamine, are associated with mental status changes that have similarity to psychotic or dissociative symptoms seen in psychiatric disorders. While in nonclinical studies compound A did not demonstrate NMDA antagonist activity, the present study included precautions related to potential dissociative effects and other adverse psychiatric effects by excluding subjects with a psychiatric history.

Study Objectives:
  Primary Objective: The primary objectives of this study were to evaluate the PK profile of compound A in plasma and CSF in healthy normal male volunteers.
  Secondary Objectives: The secondary objectives of this study were to evaluate the safety and tolerability of a single, oral, 2400-mg dose of compound A in healthy normal male volunteers.
  Exploratory Objective(s): The exploratory objectives of this study were as follows using CSF and plasma samples collected over the same time frame as the PK samples:
    conducted unbiased metabolomic analysis using validated methods as described: https://www.metabolon.com/what-we-do/our-technology.
    conducted unbiased proteomic analysis using validated methods as described: https://www.biognosys.com/technology.

Figure 7:
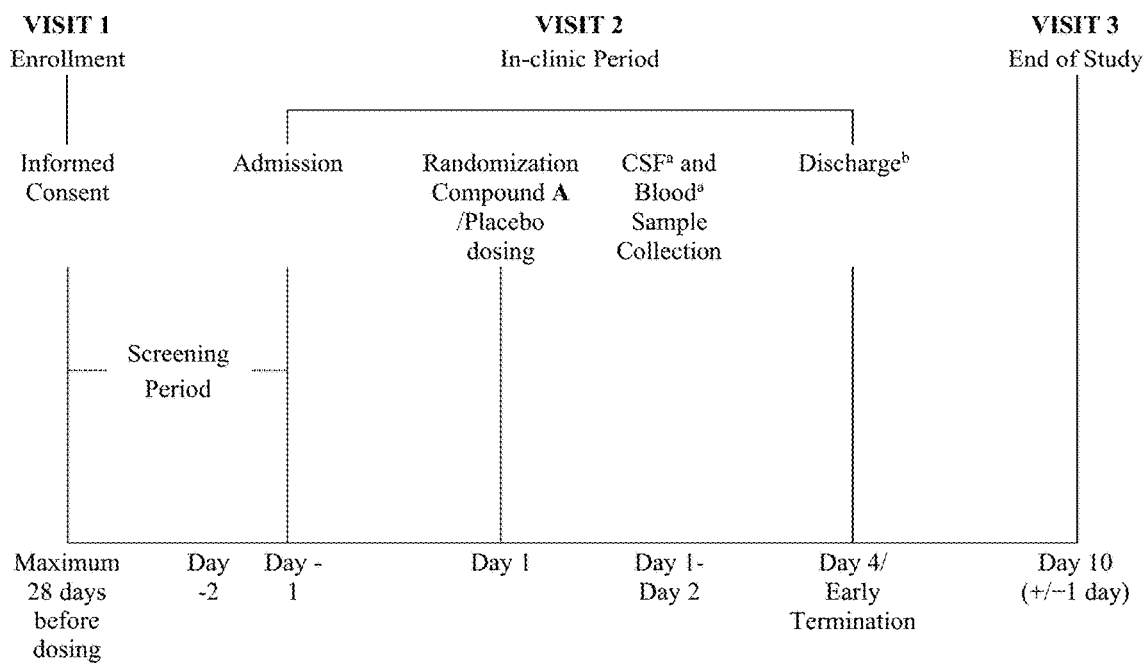
FIG. 7 depicts the clinical trial study flow chart for the clinical trial described in Example 2.

Study Endpoints:
  Safety Endpoints: The following safety variables were recorded at regular intervals during the study:
    Vital signs (supine BP, HR, body temperature, and respiratory rate [RR])
    12-lead electrocardiograms: PR interval, QRS interval, RR interval, QT interval, and QT interval corrected for heart rate (QTc) (Bazett's correction [QTcB] and Fridericia's correction [QTcF])
    Clinical laboratory tests (clinical chemistry, hematology, and coagulation)
    AE assessments
    Neurological examination
    Physical examinations
  Pharmacokinetics Endpoints: The following PK parameters for compound A were determined in serum and CSF, as appropriate:
    $C_{max}$: Maximum compound A concentration determined directly from the concentration-time profile
    $T_{max}$: Time of maximum compound A concentration determined directly from the concentration-time profile
    $AUC_{last}$: Area under the concentration-time curve from pre-dose (time 0) to the time of the last quantifiable concentration ($t_{last}$) calculated using the linear-log trapezoidal rule
    $AUC_{inf}$: Area under the concentration-time curve from pre-dose (time 0) extrapolated to infinite time ($AUC_{last}+C_{last}/\lambda_z$) calculated using the linear-log trapezoidal rule
    $AUC_{\% \, extrap}$: Percentage of $AUC_{inf}$ that is due to extrapolation beyond $t_{last}$
    $\lambda_z$: The terminal elimination rate constant determined by selection of at least 3 data points on the terminal phase of the concentration-time curve.
    $t_{1/2}$: Terminal elimination half-life calculated as: $\ln 2/\lambda_z$
    CL/F: Apparent body clearance calculated as: Dose/$AUC_{inf}$
    Vz/F: Apparent volume of distribution calculated as: Dose/($AUC_{inf}*\lambda_z$)
    MRT: Mean residence time (of the unchanged drug in the systemic circulation) as: AUMC/AUC
    $R_{A \, (AUC)}$: Accumulation CSF/plasma ratio calculated as the ratios of the $AUC_{inf,ss}$ at steady state and $AUC_{\tau,sd}$ after single dosing calculated as: $AUC_{\tau,ss}/AUC_{\tau,sd}$ $R_{A\ (Cmax)}$: Accumulation CSF/plasma ratio calculated as ratio of $C_{max,ss}$ at steady state and $C_{max,sd}$ after single dosing calculated as: $C_{max,ss}/C_{max,sd}$ CSF compound A concentrations over time and the ratio compared with time-matched plasma concentrations were also evaluated CSF compound A concentrations over time and the ratio compared with time-matched plasma concentrations were also evaluated Overall Study Design:

This study was a Phase 1, double-blind, placebo-controlled, single-dose study to evaluate the PK, metabolomic, and proteomic profiles of compound A in plasma and CSF in healthy male subjects between the ages of 18 and 55 years. Subjects had a screening visit within 28 days prior to study drug administration. Once eligibility criteria were met and the ICF had been signed, subjects were admitted to the CRU on Day-1. On Day 1, intradural and venous catheters were inserted and subjects were randomly assigned to double-blind treatment with a single oral 2400 mg dose of compound A or placebo. The catheter insertion site was assessed on regular basis for early signs of local infection or CSF leakage. Time-matched CSF and blood samples were then collected for 36 hours, after which, the intradural and venous catheters were removed. See FIG. 7 for the study flow chart.

Study Design Rationale:

This study was conducted to assess the safety, tolerability, and PK of a single dose of compound A versus placebo. The design of this clinical study followed the recommendation of the United States Food and Drug Administration (FDA) guidance document for a double-blind, placebo-controlled study. This study evaluated the safety, tolerability, PK, metabolomics, and proteomics of compound A administered in solution as a single oral dose (2400 mg).

Dose Selection Rationale:

The dosage level for this study (2400 mg) was based on the preliminary safety, tolerability, and PK data from a single ascending-dose study (see part A of Example 1, above).

Study Duration:

The duration of participation for each subject was approximately 38 days. The estimated study duration included:
1. The screening period: Up to 28 days
2. Treatment period: Up to Day 2
3. Discharge: at least 36 hours post removal of intradural catheter
4. EOS: 7 days (+/−1 day) after discharge from the CRU Study Completion:

A subject was considered to have completed the study if he had completed all scheduled procedures of the study and had provided all scheduled CSF and blood samples. The end of the study was defined as the date of the last scheduled procedure shown in the Schedule of Activities for the last subject in the study.

Subject Selection Criteria:

The study population consisted of healthy male volunteers. Subjects had to be able to provide written informed consent and meet all the inclusion criteria and none of the exclusion criteria. 13 subjects were randomized, 13 subjects were evaluated for safety, and 12 subjects were evaluated for CSF.

Inclusion Criteria: Subjects who met the following criteria were considered eligible to participate in the clinical study:

Subjects had to understand the nature of the study and provided signed and dated written informed consent before the conduct of any study-related procedures.

Subjects had to be between 18 and 55 years of age, inclusive, at time of signing informed consent.

Subjects had to be non-smokers (ie, have abstained from any tobacco [eg, cigar, cigarette, or snuff] or nicotine-containing [eg, nicotine chewing gum, nicotine plasters, or other product used for smoking cessation] or e-cigarette products) within 12 months prior to screening.

Subjects had to have a BMI between 19 and 30 kg/m², inclusive.

Subjects who were biologically capable of having children (ie, non-vasectomized) had to agree to use one or more appropriate forms of birth control for either themselves or their partner(s), from the time of signing the informed consent through at least 90 days following the administration of test article.

Subjects had to be, in the opinion of the Principal Investigator, able to participate in all scheduled evaluations, likely to complete all required tests, and likely to be compliant.

Exclusion Criteria: Subjects were not entered into the study if any of the following exclusion criteria were fulfilled:

A clinically significant illness (including chronic, persistent, or acute infection), medical/surgical procedure, or trauma within 30 days prior to screening or between screening and before randomization (Day 1).

A history or presence of a clinically significant hepatic, renal, gastrointestinal, cardiovascular, endocrine, respiratory, immunologic, hematologic, dermatologic, or neurologic abnormality.

A history or presence of any disease, condition, or surgery likely to affect drug absorption, distribution, metabolism, or excretion.

A clinically significant physical, neurological, electrocardiogram (ECG), or laboratory test abnormality at screening or between screening and Day −1. Procedures were to be repeated once as per Principal Investigator discretion.

A history of seizure.

A history of clinically significant head trauma, including closed head injury with loss of consciousness.

Positive serology test results for human immunodeficiency virus antibodies, hepatitis B surface antigen, or hepatitis C antibody.

Positive urine drug screen, alcohol test, or cotinine test at screening or Day −1.

A clinically significant vital signs abnormality at screening or between screening and Day −1. This included the following after at least 5 minutes supine controlled rest: a) systolic BP>150 mmHg, b) diastolic BP>95 mmHg, or c) heart rate <50 or >90 beats per minute (bpm). Vitals were to be repeated once as per Principal Investigator discretion.

Unexplained (>10%) weight loss or gain within 6 months prior to screening or between screening and before admission to the CRU (Day −1).

A history of clinically significant symptomatic orthostatic hypotension (ie, postural syncope).

A history of neuroleptic malignant syndrome.

A history of cancer within 5 years prior to screening or between screening and randomization (with the exception of non-metastatic basal and/or squamous cell carcinoma of the skin), any history of renal cell carcinoma or breast cancer, or a family history of lymphangioleiomyomatosis in association with tuberous sclerosis complex.

Any illness or condition at screening or between screening and before randomization (Day 1) that, in the opinion of the Principal Investigator, a) significantly increased the potential risk associated with the subject's participation in the study, b) decreased the likelihood the subject would complete the study, and/or c) could confound the results of the study.

A diagnosis of intellectual disability (intellectual developmental disorder) or mental retardation; history of psychiatric disorders, including substance use disorders, according to the DSM-5 criteria; and a history of prescription or nonprescription medications for attention-deficit hyperactivity disorder, narcolepsy, or cognitive enhancement (eg, methylphenidate, atomoxetine, modafinil, Ginkgo biloba, and huperzine a) within 1 month prior to screening or b) between screening and before randomization (Day 1).

Used any vitamin or herbal supplement within 2 weeks prior to randomization (Day 1), unless approved by the Principal Investigator and Medical Monitor.

Consumed alcohol or used any over-the-counter medication (other than up to 2 grams per day paracetamol/acetaminophen) within 7 days prior to randomization (Day 1).

Regularly consumed (eg, more days than not) excessive quantities of xanthine-containing beverages (eg, more than 5 cups of coffee or the equivalent per day) 72 hours prior to randomization (Day 1).

Donated blood or plasma within 6 weeks prior to randomization (Day 1).

Used any experimental medication, device, or biologic within 30 days for non-biologicals, 3 months for biologicals or 5½ lives, whichever is longer, prior to randomization (Day 1).

Was currently employed by Navitor or at the CRU participating in this study, or a first-degree relative of a Navitor employee or of an employee at the CRU.

Any condition that, in the opinion of the Principal Investigator or Medical Monitor, made the subject unsuitable for the study.

Strenuous physical activity within 1 week prior to randomization (Day 1).

Unsuitable or difficult venous access or unwilling or unable to undergo direct venipuncture or catheter insertion.

Known or suspected hypersensitivity or idiosyncratic reaction to study drug or study drug excipients.

Known or suspected hypersensitivity or idiosyncratic reaction to the anesthetic agent (eg, lidocaine) used during lumbar puncture.

Used any prescription drug within 2 weeks before randomization (Day 1).

Contraindications to lumbar puncture or CSF collection (eg, lumbar scoliosis, coagulopathy, infected skin at puncture site, etc) as determined by the Principal Investigator and/or anesthesiologist.

Unwilling or unable to comply with the required lifestyle restrictions

Treatments:

Compound A and placebo bottles were provided by Sherpa Clinical Packaging (a PCI Company) as powder in bottles and empty bottles to be reconstituted by the site pharmacist or other appropriately qualified staff member, according to local regulations. For the compound A oral solution, the clinical dose consisted of 2400 mg compound A, reconstituted in approximately 42 mL United States Pharmacopeia (USP) purified water, and 18 mL Flavor Sweet-SF™ (a flavor-masking agent). Placebo doses contained these same components absent the active ingredient. The identity of the investigational products is presented in Table 16, below.

TABLE 16

Identity of Investigational Product

| Drug Name | Dose | Concentration | Route | Manufacturer of Active Ingredient |
|---|---|---|---|---|
| Compound A | 2400 mg | 40 mg/mL | Oral | Aptuit, Verona, Italy |
| Placebo | N/A | N/A | Oral | No active ingredient |

Doses and Treatment Regimens: Subjects abstained from all food and drink (except water) at least 8 hours prior to dosing on Day 1. Water was permitted until 1 hour prior to study medication administration. Fasting restrictions continued for at least 2 hours post dose. Water was allowed to be consumed without restriction beginning 1 hour after dosing.

Pharmacokinetic, Metabolomic, and Proteomic Variables: Blood and CSF samples for the PK, metabolomics, and proteomic analysis of compound A were collected at various time points and were processed and analyzed by a validated method for determining concentrations of compound A.

Figure 8:
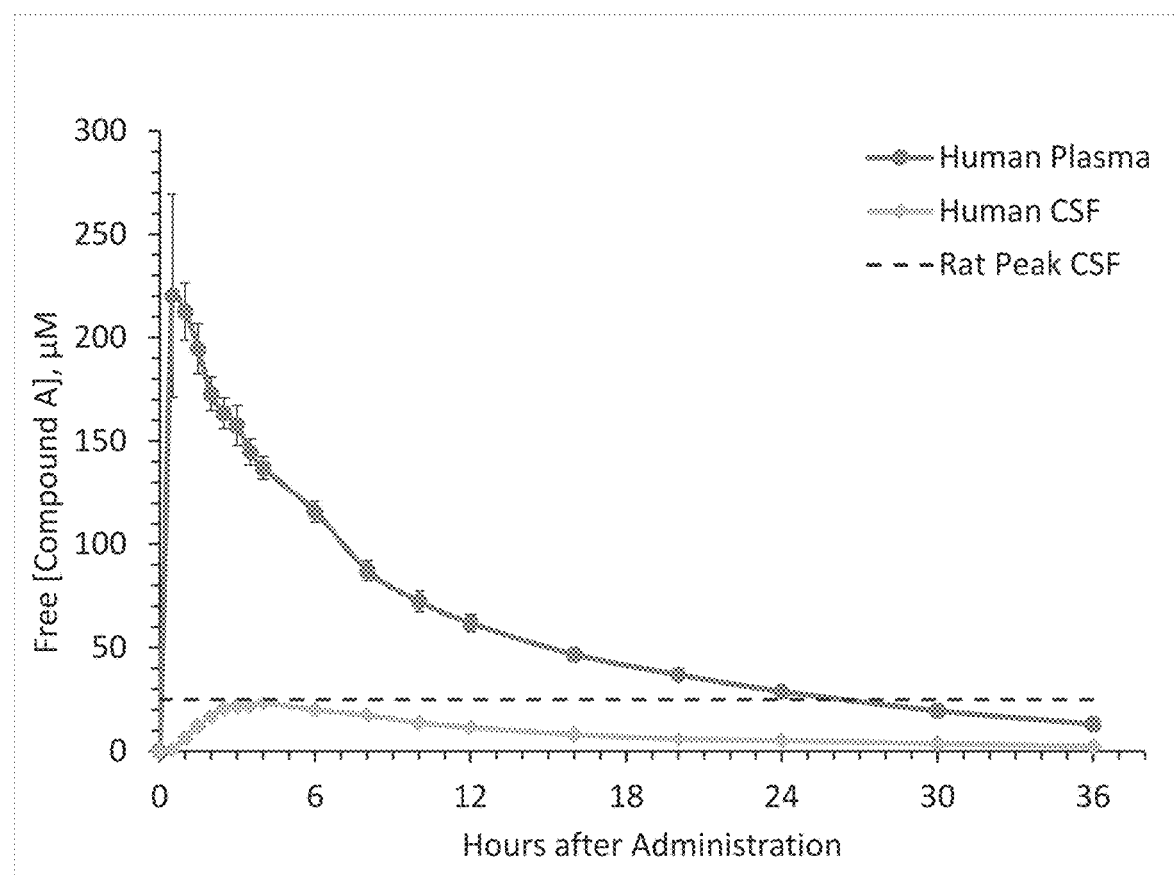
FIG. 8 shows human CSF levels consistent with rodent levels at the effective dose of compound A.
Figure 9:
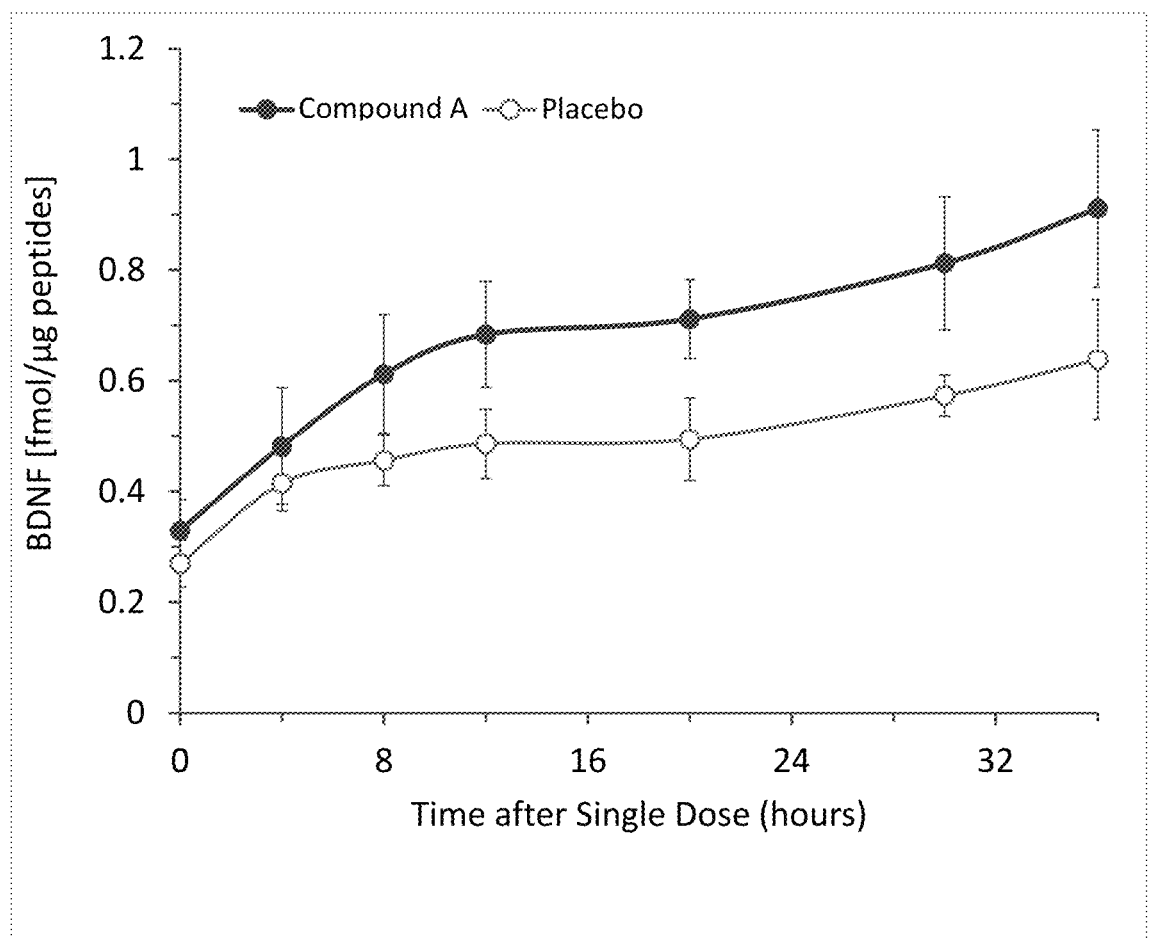
FIG. 9 shows CSF BDNF levels after a single dose of compound A.
Figure 10:
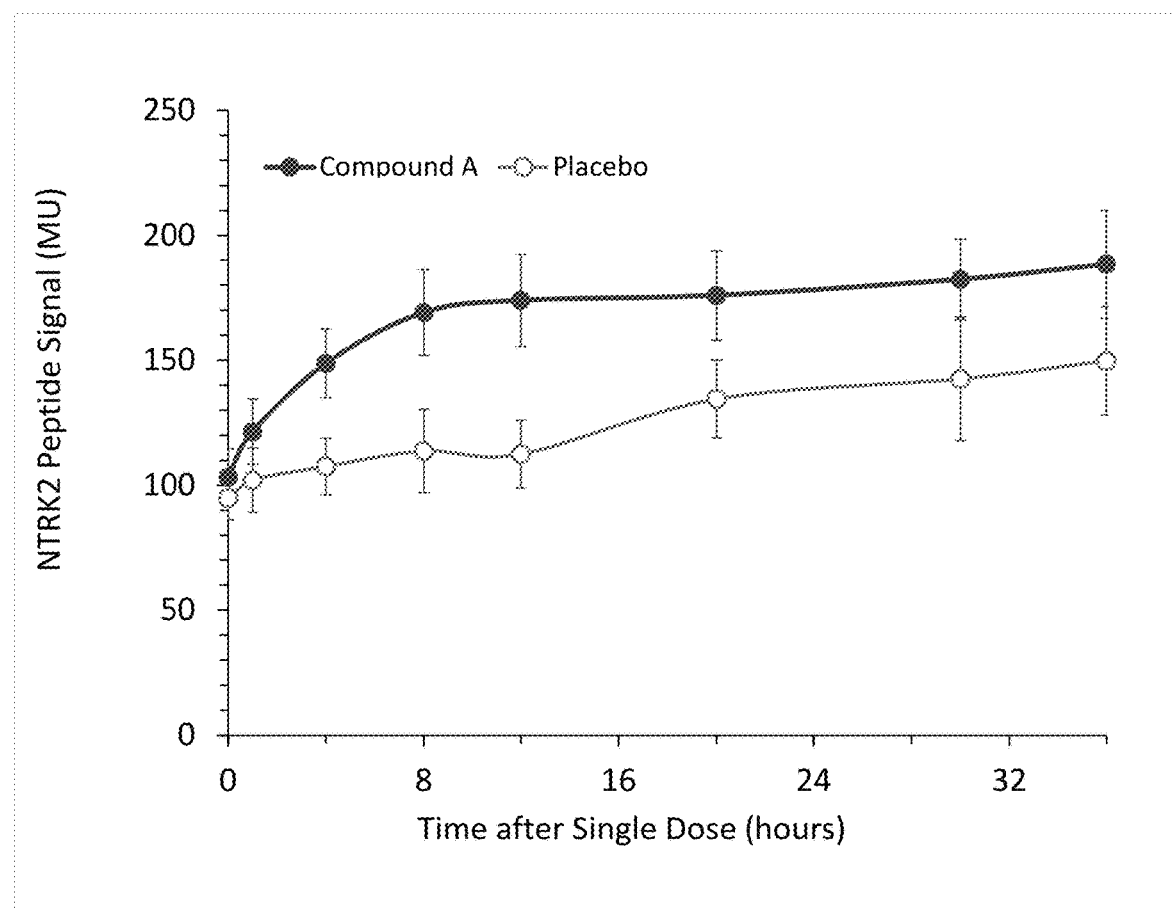
FIG. 10 shows BDNF receptor (NTRK2) fragment levels after a single dose of compound A.

Study Results:

Results show rapid uptake of compound A into circulation with rapid brain exposure. Results also indicate a half-life of 10-13 h suitable for daily administration. See FIG. 8, showing human CSF levels consistent with rodent levels at the effective dose. FIGS. 9 and 10 show CSF BDNF and BDNF receptor (NTRK2) fragment levels, respectively, after a single dose. mTORC1 activation led to rapid release of BDNF and receptor degradation.

Single dose compound A rapidly affected key neurotransmitter turnover, e.g., GABA, histamine, serotonin, and dopamine, within two hours of treatment, and was sustained for 36 hours post-dose. Low CSF concentrations of HVA have been reported to be a marker of depressive symptoms. Table 17 shows CSF neurotransmitter metabolomics after a single dose. Values represent the ratio of metabolite concentrations for each time point relative to baseline. An increase from baseline is indicated with a single asterisk (*).

TABLE 17

| Biochemical Name/Hours | Placebo (n = 4) | | | | | | | Compound A (n = 12) | | | | | | |
|---|---|---|---|---|---|---|---|---|---|---|---|---|---|---|
| Post-Dose | 1 h | 2 h | 4 h | 8 h | 12 h | 24 h | 36 h | 1 h | 2 h | 4 h | 8 h | 12 h | 24 h | 36 h |
| Carboxyethyl-GABA | 1.05 | 1.16* | 0.99 | 1.14 | 1.06 | 1.21* | 1.03 | 1.12 | 1.29* | 1.38* | 1.38* | 1.4* | 1.24* | 1.22* |
| 1-methyl-4-imidazoleacetate | 0.94 | 1.22 | 1.38 | 1.37 | 1.35 | 1.21 | 1.34 | 1.08 | 1.35* | 1.52* | 1.47* | 1.56* | 1.33* | 1.75* |

TABLE 17-continued

| Biochemical Name/Hours | Placebo (n = 4) | | | | | | | Compound A (n = 12) | | | | | | |
|---|---|---|---|---|---|---|---|---|---|---|---|---|---|---|
| Post-Dose | 1 h | 2 h | 4 h | 8 h | 12 h | 24 h | 36 h | 1 h | 2 h | 4 h | 8 h | 12 h | 24 h | 36 h |
| Homovanillate (HVA) | 1.07 | 1.35* | 1.31 | 1.13 | 1.11 | 1.24 | 1.33* | 1.08 | 1.41* | 1.56* | 1.3* | 1.46* | 1.34* | 1.41* |
| Hydroxyindole-acetic acid (HIAA) | 0.98 | 1.13 | 1.2* | 1.12 | 1.03 | 1.16 | 1.17 | 1.09 | 1.28* | 1.1* | 1.22 | 1.21 | 1.21* | 1.28* |

Conclusion: In summary, this study provides key biomarker evidence that a single 2400 mg dose of Compound A achieves effective concentrations in the brain and activates neural pathways that are important to depression.

Example 3. A Randomized, Double-Blind, Placebo-Controlled Study of the Effects on Quantitative Electroencephalography and Event-Related Potential of Two Sequential Doses of Compound A in Healthy Adult Males Single ascending doses of compound A were assessed in healthy adult males and females in Part A of a two-part, randomized, double-blind, placebo-controlled, first-in-humans Study (see Example 1, Part A). Based on preliminary blinded results from Part A, single ascending doses of compound A up to, and including, 2400 mg were found to be generally safe and well tolerated. Preliminary assessments of dose linearity as well as PK parameters vs. dose from Part A of the Study (see Example 1) revealed the following:

Plasma compound A concentrations increased rapidly. Median $T_{max}$ values ranged from 0.5 to 1.5 hours post dose.

Plasma compound A exposure parameters ($C_{max}$ and $AUC_\infty$) increased with dose in slightly less than dose-proportional manner from 150 mg to 2400 mg.

Compound A CL/F and Vz/F estimates increased with dose, while the terminal elimination half-life estimates were similar among cohorts (12.7 to 15.9 hours). This is consistent with decreases in relative bioavailability with increasing doses.

Modeling based on the single-dose pharmacokinetic data support that minimal accumulation would be expected with dosing every other day or every third day.

The research hypothesis for this study was that, compared to placebo, two sequential oral doses of 2400 mg compound A administered approximately 48 hours apart would be generally safe and well tolerated, and associated with specific spectral power changes on qEEG, supporting the safety and tolerability of sequential oral doses of compound A, and the utility of qEEQ as a functional indicator (biomarker) of compound A pharmacodynamic activity. The qEEG preclinical changes are suggestive of activity in depression and in greater higher frequency activity on spectral analysis.

The preclinical data suggest that downstream signaling changes in the mTORC1 pathway should result in improved signal processing of stimuli as reflected in changes in the ERP paradigms selected.

Compound A is intended to be developed for the treatment of TRD. As described above, single ascending doses of compound A were assessed in healthy adult males and females in the first part of a two-part, randomized, double-blind, placebo-controlled study (see Example 1, Part A). Based on preliminary results from the first part of that study, single ascending doses of compound A up to and including 2400 mg were found to be safe and well tolerated. This study was designed to investigate the safety, tolerability, pharmacodynamics, and pharmacokinetics of two sequential doses of 2400 mg compound A (separated by 2 days), compared with placebo, in 24 healthy adult males (12 receiving compound A, 12 receiving placebo). Pharmacodynamic assessments included qEEG and event-related potential (ERP) measurements.

While seizures have not been observed in nonclinical studies with compound A or in the limited clinical experience to date, to mitigate the potential risk of seizure, subjects with a history of seizure were excluded from the present clinical study. In addition, safety EEGs at screening were read by a neurologist prior to first dose administration to rule out subjects with possible seizure potential, and the EEG were collected continuously for 8 hours post dose (Day 1 and Day 3). These continuous EEG records were reviewed post hoc by an experienced registered EEG technologist (R.EEG T). Records with signs of epileptiform activity noted during review were sent to a neurologist. Suspicious clinical signs indicative of seizure observed by any clinical staff during EEG acquisition also potentially precipitated review of the EEG record by a neurologist and/or transfer of the subject to a hospital facility at the discretion of the principal investigator.

NMDA antagonists, in particular ketamine, are associated with mental status changes that have similarity to psychotic or dissociative symptoms seen in psychiatric disorders. While in nonclinical studies compound A did not demonstrate NMDA antagonist activity, the present study included precautions related to potential dissociative effects and other adverse psychiatric effects, including the exclusion of subjects with a psychiatric history, clinical assessments of psychiatric symptoms during the course of the study, and psychiatric symptom ratings.

Some drugs, including the NMDA antagonist ketamine, are associated with a risk of abuse. While the potential for abuse liability with compound A appears low based the available nonclinical data, specific nonclinical and clinical abuse liability studies have not yet been performed with compound A. Thus, the present study contained precautions related to potential abuse liability, including the exclusion of subjects with a history of psychiatric disorders (including substance use disorders) and clinical assessments of psychiatric symptoms throughout the study.

In nonclinical studies (rat), oral administration of high doses of compound A (≥500 mg/kg Q3D for 14 days) was associated with lymphoid atrophy and decreased leucocyte counts. In this clinical study, precautions related to hematology findings in nonclinical studies with compound A included exclusion of subjects with white blood cell or absolute neutrophil counts that were clinically significantly below the normal range. In addition, the present clinical study included frequent clinical laboratory tests.

In a cardiovascular study in cynomolgus monkeys, oral administration of a single dose of compound A (≥160 mg/kg) was associated with decreased heart rate and body temperature. Increased blood pressure was noted at higher dosage levels (≥500 mg/kg). In a toxicology study in cynomolgus monkeys, oral administration of compound A (≥500 mg/kg Q3D for 14 days) was associated with decreased heart rate. Precautions related to cardiovascular safety in this clinical study included frequent measurement of vital signs (e.g., blood pressure, pulse, and body temperature) and frequent electrocardiograms (ECGs).

Study Objectives:

Primary Objective: The primary objectives of this study were (1) to assess the safety and tolerability and (2) to assess the pharmacodynamics (assessed by qEEG) of two sequential doses of 2400 mg compound A versus placebo in healthy male volunteers.

Secondary Objectives: Secondary objectives were (1) to assess the pharmacodynamics (assessed by ERP); (2) to assess the pharmacokinetics of two sequential doses of 2400 mg compound A in healthy male volunteers, and (3) to develop a PK/PD model that measures qEEG and ERP changes as a function of plasma concentration of compound A as well as determining whether there are any PK/PD differences between Dose 1 and Dose 2 effects.

Exploratory Objective(s): An exploratory objective was to assess the potential relationships between single-nucleotide polymorphism in the BDNF gene (a methionine [Met] substitution for valine [Val] at codon 66; Val66Met) and pharmacodynamic parameters.

Study Endpoints:

Safety Endpoints: The safety endpoint was to assess the safety and tolerability of sequential doses of compound A vs. placebo in healthy male volunteers, as assessed by clinical laboratory parameters, physical, neurologic, and psychiatric examinations, vital signs, ECGs, EEGs, and adverse events.

Pharmacodynamic Endpoints: The primary pharmacodynamic endpoint was the change from baseline in the difference between the compound A group and the placebo group on qEEG parameters, including:

Fractal and oscillatory EEG band amplitudes

Fractal and oscillatory EEG band intra- and interhemispheric coherences

The secondary pharmacodynamic endpoints were the changes from baseline in the difference between the compound A group and the placebo group in ERP parameters, including:

Mismatch negativity (MMN) amplitude and latency
P300a amplitude and latency
P300b amplitude and latency
N100 amplitude and latency
N200 amplitude and latency
P200 amplitude and latency
Auditory steady-state response (ASSR) peak-to-peak amplitude
ASSR event-related spectral perturbation (ERSP)
ASSR inter-trial phase coherence (ITPC)
Mean time scores of qEEG parallel factor analysis (PARAFAC) atoms endpoints Pharmacokinetic Endpoint: The pharmacokinetic endpoint was to assess the pharmacokinetics of sequential doses of compound A in healthy male volunteers.

Pharmacogenetic Endpoint: The pharmacogenetic endpoint was to assess the potential relationships between single-nucleotide polymorphism in the BDNF gene (Val66Met) and pharmacodynamic parameters.

Overall Study Design:

This study was a randomized, double-blind, placebo-controlled study of two doses, 48 hours ±30 minutes apart, of compound A in healthy adult male volunteers. The study included an up to 28-day screening period, an in-house period during which compound A or placebo was administered, and a 3- to 7-day follow-up period after discharge.

Up to approximately 24 healthy male volunteers were randomly assigned (1:1) to double-blind treatment with either compound A 2400 mg or placebo. Each subject received one dose of either 2400 mg compound A or placebo on Day 1 and a second dose of the same treatment on Day 3.

The initial dose of double-blind treatment was administered between 7:00 AM and 10:00 AM on Day 1. The second (Day 3) dose was given 48 hours ±30 minutes following the first (Day 1) dose. Predose assessments were performed up to 120 minutes prior to dosing on Day 1 and Day 3, except for the predose dECG, which was performed within 30 minutes prior to dosing on both Day 1 and Day 3, the predose qEEG and ERP, which was performed within 60 minutes prior to dosing on Day 1 and Day 3, and the predose PK blood draw, which was performed within 15 minutes prior to dosing on Day 3.

Initially, one subject received compound A (Day 1 and Day 3) and one subject received placebo (Day 1 and Day 3) in a blinded manner. Provided no clinically significant safety issues were noted in the 24 hours after dosing the initial two subjects, additional subjects were dosed. The in-house period was 8 days/7 nights. The duration of each subject's participation was up to 41 days, including screen and follow-up.

TABLE 18

The chart for this study

| Screening Visit, Days | Residential/In-House Period (8 days/7 nights) | | | | | | | Follow-Up Visit |
|---|---|---|---|---|---|---|---|---|
| −28 to −3 | Day −2 | Day −1 | Day 1 | Day 2 | Day 3 | Days 4-5 | Day 6 | (Days 9-13) |
| Clinic visit [a] | Admission to study unit, incl./excl., observation, assessments | Observation, assessments (vital signs, initial qEEG, ERP), incl./excl. | Randomization; incl./excl., DB dose of compound A or placebo, assessments | Observation, assessments | Second DB dose of compound A or placebo, assessments | Observation, assessments | EOS assessments, discharge from study unit | Clinic visit 5 ± 2 days after discharge |

Abbreviations:
DB, double-blind;
EOS, end-of-study;
excl., exclusion criteria;
ERP, event-related potential;
incl., inclusion criteria;
qEEG, quantitative EEG Study Design Rationale:

This study was designed to evaluate the safety, tolerability, pharmacodynamics, and pharmacokinetics of two sequential doses of 2400 mg compound A (separated by 2 days), compared with placebo, in 24 healthy adult males (12 receiving compound A, 12 receiving placebo). The study included standard safety and tolerability assessments—e.g., physical, neurological, and psychiatric examinations, vital signs, oral temperature, respiration rate, weight, 12-lead paper electrocardiograms (pECGs), dECGs, clinical laboratory tests, monitoring of adverse events (AEs) and concomitant medications, and safety EEGs. The study also included safety and tolerability assessments specific for drugs that may have psychiatric effects—e.g., the Columbia-Suicide Severity Rating Scale (C SSRS), the Brief Psychiatric Rating Scale-Positive Symptom Subscale [BPRS (+)], and the Clinician Administered Dissociative States Scale (CADS S).

Pharmacodynamics were assessed via qEEG and event-related potential (ERP). Frequent PK sampling was included in the study to evaluate the PK of two doses of compound A given approximately 48 hours apart. A PK/PD model was developed that measures qEEG and ERP changes as a function of plasma concentration of compound A as well as determines whether there are any PK/PD differences between Dose 1 and Dose 2 effects.

Dose Selection Rationale:

The selected dose of 2400 mg compound A was found to be generally safe and well tolerated in healthy adult male and female subjects in Example 1, part A, and is the highest dose tested.

Control Group Rationale:

Placebo was included to permit comparative assessment of compound A's safety, tolerability, and pharmacodynamics, and to facilitate evaluation of the balance of benefit and risk provided by compound A.

Subject Selection Criteria:

Inclusion Criteria: Subjects who met the following criteria were considered eligible to participate in the clinical study:
- Subjects had to understand the nature of the study and provided signed and dated written informed consent before the conduct of any study-related procedures.
- Subjects were male and age 18-55, inclusive.
- Subjects who were biologically capable of having children (i.e., non-vasectomized) had to agree to use one or more of the following forms of birth control for either themselves or their partner(s), as appropriate, from the time of signing the informed consent form through at least 90 days following the last administration of test article: hormonal (i.e., oral, transdermal, implant, or injection); double barrier (i.e., condom, diaphragm with spermicide); intrauterine device (IUD). Vasectomized men had to have been vasectomized at least 6 months prior to first dose administration (Day 1) or had to agree to use one or more of the above forms of birth control for either themselves or their partner(s), as appropriate, from the time of signing the informed consent form through at least 90 days following the last administration of test article.
- Subjects had to be, in the opinion of the investigator, able to participate in all scheduled evaluations (including qEEG and ERP), likely to complete all required tests, and likely to be compliant.
- Subjects had to be fluent in English.
- Subjects had to have a body mass index (BMI) between 19 and 30, inclusive.

Exclusion Criteria: Subjects were not entered into the study if any of the following exclusion criteria were fulfilled:
- A clinically significant illness (including chronic, persistent, or acute infection), medical/surgical procedure, or trauma within 30 days prior to screen or between screen and first dose administration (Day 1)
- A history or presence of a clinically significant hepatic, renal, gastrointestinal, cardiovascular, endocrine, respiratory, immunologic, hematologic, dermatologic, or neurologic abnormality
- A history or presence of any disease, condition, or surgery likely to affect drug absorption, distribution, metabolism, or excretion
- A history or presence of any psychiatric disorder, including but not limited to any psychotic disorder, substance use disorder, depressive disorder, anxiety disorder, bipolar disorder, or attention-deficit/hyperactivity disorder (ADHD), according to the DSM-5 criteria
- A history or presence of suicidality as evidenced by answering "yes" for Question 4 ("Lifetime") or Question 5 ("Lifetime") on the Columbia-Suicide Severity Rating Scale (C-SSRS), indicating active suicidal ideation with any intent to act, at screen or between screen and first dose administration (Day 1), or by answering "yes" for Question 3 ("In the Past Year") on the C-SSRS, indicating active suicidal ideation with any methods (not plan) without intent to act, at screen or between screen and first dose administration (Day 1)
- A history or presence of suicidal behavior such that a determination of "yes" is made on the Suicidal Behavior section of the C-SSRS ("Lifetime") for "Actual Attempt," "Interrupted Attempt," "Aborted Attempt," or "Preparatory Acts or Behavior.
- A clinically significant abnormality on physical examination, neurological examination, electrocardiogram (ECG), or laboratory evaluations at screen or between screen and first dose administration (Day 1).
- A clinically significant observation noted by the neurologist on the screening EEG of epileptiform activity or other finding(s) suggestive of a neurologic disorder or other abnormality that might put the subject at risk, interfere with qEEG or ERP testing, or confound data interpretation
- Alanine aminotransferase (ALT) or aspartate aminotransferase (AST) levels greater than 1.5 times the upper limit of normal (ULN) at screen or between screen and first dose administration (Day 1).
- Creatine kinase (CK) level greater than 1.5×ULN at screen or between screen and first dose administration (Day 1). In addition, any clinically significant CK level (as determined by the investigator) was exclusionary.
- Creatinine clearance <60 mL/min, according to the Cockcroft-Gault equation.* White blood cell or absolute neutrophil counts that were clinically significantly below the normal range at screen or between screen and first dose administration (Day 1).
- A clinically significant vital signs abnormality at screen or between screen and first dose administration (Day 1). This included, but was not limited to, the following, in the supine position (after at least 5 minutes supine controlled rest): (a) systolic blood pressure >150 mmHg, (b) diastolic blood pressure >95 mmHg, or (c) heart rate <45 or >95 beats per minute.
- A corrected QT interval measurement corrected according to the Fridericia rule (QTcF) >450 msec during controlled rest at screen or between screen and first dose administration (Day 1), or family history of long-QT syndrome.

Any clinically significant abnormalities in rhythm, conduction, or morphology of the resting ECG and any abnormalities in the 12-lead ECG that, in the judgement of the investigator, could have interfered with the interpretation of QTc interval changes, including abnormal ST-T-wave morphology or left ventricular hypertrophy.

PR (PQ) interval shortening <120 msec (PR<120 msec but >110 msec was acceptable if there was no evidence of ventricular pre-excitation).

PR (PQ) interval prolongation (>240 msec), intermittent second-degree (Wenckebach block while asleep or in deep rest was not exclusionary) or third-degree atrioventricular bloc.

Persistent or intermittent complete bundle branch block (BBB), or intraventricular conduction delay (IVCD) with QRS>110 msec.

Significant (>10%) weight loss or gain within 30 days prior to screen or between screen and first dose administration (Day 1).

A history of seizure, loss of consciousness for an unknown reason, or any other known neurological disorder placing the subject at risk for seizures.

A history of clinically significant head trauma, including closed head injury with loss of consciousness.

A history of clinically significant symptomatic orthostatic hypotension (i.e., postural syncope).

A history of neuroleptic malignant syndrome.

A history of cancer within 5 years prior to screen or between screen and randomization (with the exception of non-metastatic basal and/or squamous cell carcinoma of the skin), any history of renal cell carcinoma or breast cancer, or a family history of lymphangioleiomyomatosis in association with tuberous sclerosis complex (TSC-LAM).

Any illness or condition that, in the opinion of the investigator, (a) significantly increased the potential risk associated with the subject's participation in the study, (b) decreased the likelihood the subject will complete the study, and/or (c) could confound the results of the study.

A diagnosis of intellectual disability (intellectual developmental disorder) or mental retardation.

Consumed alcohol within 7 days prior to screen or between screen and first dose administration (Day 1).

Regularly consumed (e.g., more days than not) excessive quantities of xanthine-containing beverages (e.g., more than five cups of coffee or the equivalent per day) within 30 days prior to screen or between screen and first dose administration (Day 1).

Donated blood or plasma within 6 weeks prior to screen or between screen and first dose administration (Day 1).

Used any experimental medication, device, or biologic within 3 months or five half-lives (whichever is longer) prior to first dose administration (Day 1).

Was currently employed by Navitor Pharmaceuticals, Inc. or by a clinical trial site participating in this study, or a first-degree relative of a Navitor Pharmaceuticals, Inc. employee or of an employee at a participating clinical trial site.

Any condition that, in the opinion of the investigator or medical monitor, made the subject unsuitable for the study.

Strenuous physical activity (e.g., exercise, weight lifting, and moving furniture) within 1 week prior to first dose administration (Day 1).

Unsatisfactory venous access.

Known or suspected hypersensitivity or idiosyncratic reaction to study drug or study drug excipients.

Urine drug screen positive for a drug of abuse (including *Cannabis*) or cotinine, or positive urine alcohol screen.

Used any prescription drug within 2 weeks, or five half-lives (whichever is longer), prior to screen, or between screen and first dose administration (Day 1).

Used any non-prescription drug (other than up to 3 g per day paracetamol/acetaminophen) within 2 weeks, or five half-lives (whichever is longer), prior to first dose administration (Day 1).

Used any vitamin or herbal supplement within 2 weeks prior to first dose administration (Day 1), unless approved by the investigator and medical monitor.

Used any tobacco-containing (e.g., cigar, cigarette, or snuff) or nicotine-containing product (e.g., nicotine chewing gum, nicotine plasters, or other product used for smoking cessation) within 3 months prior to screen, or between screen and first dose administration.

Insufficient hearing, according to a hearing test administered at screen.

Treatments:

Compound A was provided as powder in bottles compounded by the site pharmacist or other appropriately qualified staff member, according to local regulations. For the compound A oral solution, the clinical dose consisted of 2400 mg compound A, reconstituted in approximately 42 mL United States Pharmacopeia (USP) purified water, and 18 mL Flavor Sweet-SF™ (a flavor-masking agent). Placebo doses contained these same components absent the active ingredient. The identity of the investigational products is presented in Table 19, below.

TABLE 19

Identity of Investigational Product

| Investigational Product | Dosage Form and Strength | Manufacturer of Active Ingredient |
|---|---|---|
| Compound A | Oral solution: 40 mg/mL | Aptuit, Verona, Italy |
| Placebo | Matching oral solution | [No active ingredient] |

Doses and Treatment Regimens: Subjects randomized to receive compound A: A single dose of 2400 mg compound A was administered orally as a solution on each of Days 1 and 3. Subjects were required to refrain from eating or drinking from 2 hours prior to dose administration until two hours after dose administration.

Subjects randomized to receive placebo (purified water and Flavor Sweet-SF™): A single dose of placebo was administered orally as a solution on each of Days 1 and 3.

Results:

A single dose of compound A showed rapid and significant neural activation on qEEG versus placebo. Increased band effects are associated with arousal or alertness, and suggestive of positive mood states and improved cognitive functioning. Increased coherence is associated with functional brain network activation. See FIGS. 11 and 12, showing changes in qEEG band amplitudes and changes in qEEG band coherences, respectively. Symbols indicate either no salient changes (−), small to large increases (↑, ↑↑, ↑↑↑), small to large decreases (↓, ↓↓, ↓↓↓) or mixed decreases and increases (↓↑) in mean value differences.

Changes that were confirmed to be significant treatment effects in formal ANOVA models are indicated with a double asterisk (**).

Regarding plasma concentration-time data for compound A, on day 1, quantifiable plasma compound A concentrations were attained in all subjects by the 0.5-hour sampling time, which was the first post-dose sample. All subjects had quantifiable concentrations through 24 hours post-dose, and all subjects but one had quantifiable concentrations at 36 hours post-dose. The peak concentration for the mean profile occurred at 1 hour post-dose, with mean plasma concentrations declining in a roughly bi-phasic manner afterwards.

Figure 13:
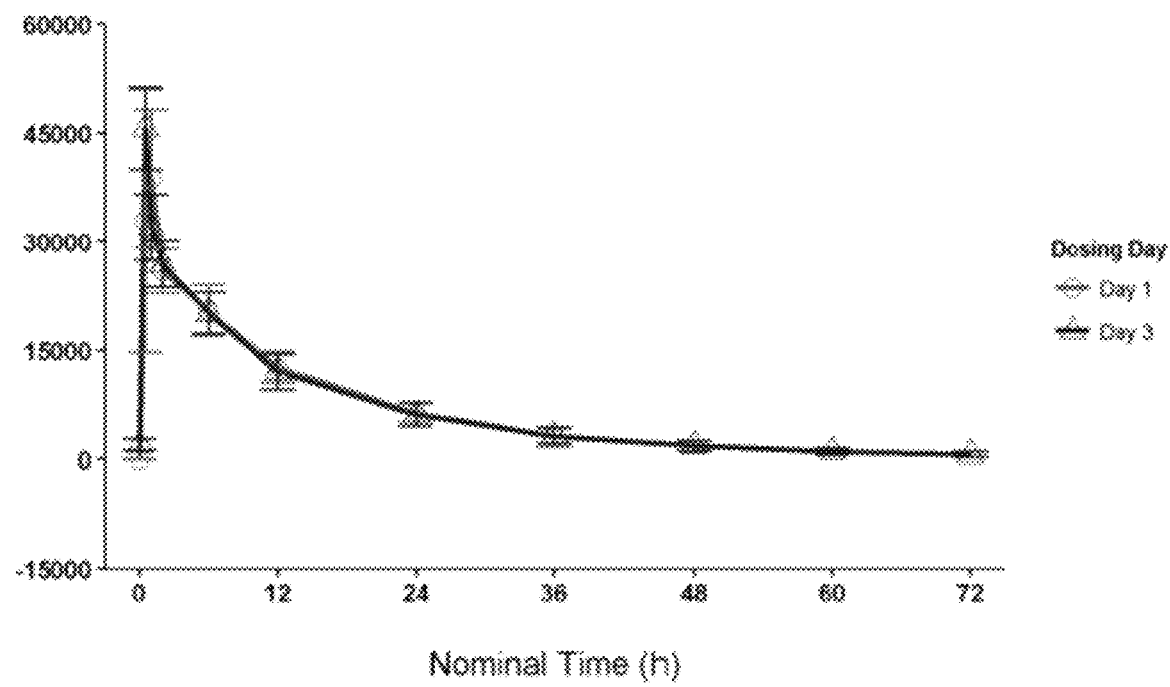
FIG. 13 depicts a graph showing mean (±SD) plasma compound A concentration (y-axis) vs. time (x-axis), overlaid by dosing day (linear scale).

All subjects had quantifiable pre-dose concentrations on day 3, and concentrations remained quantifiable in all subjects over the entire 72-hour sampling window. The highest concentration for the mean profile occurred 0.5 hours post-dose, and concentrations declined in a roughly bi-phasic manner thereafter. Mean plasma concentration versus time profiles of compound A on days 1 and 3 were nearly superimposable (see FIG. 13).

Key PK parameters for plasma compound A by dosing day are summarized in Table 20. Geometric mean exposure to compound A, as measured by Cmax, AUC(0-24), and AUC(0-48), was nearly identical (within 5%) on Day 1 and Day 3. The absorption of Compound A was rapid, as individual $T_{max}$ values were between 0.5 h and 1.0 h across all subjects on both dosing days. The geometric mean terminal elimination half-life value was approximately 20% larger on Day 3 than on Day 1. Intersubject variability was low, as the geometric CV % was less than 30% across all key parameters.

Pharmacodynamics: Nearly all salient qEEG, PARAFAC, and ASSR changes related to time after dosing were confined to the compound A group, with the placebo group showing little or no evidence of an effect of time after dosing in any measure. The compound A group showed significantly decreased delta and theta band amplitudes, decreased alpha band amplitudes within 1 hour after dosing, decreased theta-beta ratios, and increased high-frequency band amplitudes (higher beta and gamma bands). The compound A group also showed increased coherence in alpha, beta, and gamma bands.

Compound A produced dose-dependent decreases in low-frequency EEG bands (delta, theta) and increases in high-frequency EEG bands (gamma). In alpha bands, there were decreases in amplitudes (or desynchronization) at 1 hour after dosing. These changes are all signs of EEG activation, and they did not occur in the placebo group. Increased arousal, vigilance, and alertness are associated with "activated" EEG spectra, which are characterized by desynchronized alpha waves (low alpha amplitude) and absence of delta and theta waves, and which may also show increased high-frequency band amplitudes (higher beta and gamma bands). EEG activation occurred within 1 hour of the first and second doses, as indicated by decreases from baseline in delta, theta, and alpha band amplitudes. EEG activation was also evidenced by increases in beta-2, high beta, and all gamma band amplitudes. Activation is associated with increased alertness and arousal. Increased beta-gamma band amplitudes may also indicate increased levels of perceptual or cognitive processing.

TABLE 20

| Dosing Day | Statistic | Cmax (ng/mL) | Tmax (h) | AUClast (h*ng/mL) | AUC$_{(0-24)}$ (h*ng/mL) | AUC$_{(0-48)}$ (h*ng/mL) | T$_{1/2}$ (h) |
|---|---|---|---|---|---|---|---|
| Day 1 | N | 11 | 11 | 11 | 11 | 11 | 11 |
| | Mean | 45,100 | NC | 409,000 | 358,000 | 442,000 | 12.2 |
| | SD | 9,980 | NC | 60,200 | 41,500 | 60,200 | 1.62 |
| | CV % | 22.1 | NC | 14.7 | 11.6 | 13.6 | 13.3 |
| | Geometric mean | 43,900 | NC | 405,000 | 355,000 | 438,000 | 12.1 |
| | Geometric CV % | 26.1 | NC | 15.6 | 11.9 | 14.0 | 13.5 |
| | Min | 23,300 | 0.50 | 298,000 | 298,000 | 357,000 | 9.20 |
| | Median | 47,000 | 1.00 | 422,000 | 366,000 | 453,000 | 12.0 |
| | Max | 57,700 | 1.00 | 481,000 | 416,000 | 525,000 | 15.2 |
| Day 3 | | 11 | 11 | 11 | 11 | 11 | 11 |
| | Mean | 45,600 | NC | 462,000 | 353,000 | 436,000 | 15.6 |
| | SD | 5,700 | NC | 87,000 | 52,600 | 76,200 | 2.94 |
| | CV % | 12.5 | NC | 18.8 | 14.9 | 17.5 | 18.9 |
| | Geometric mean | 45,300 | NC | 455,000 | 350,000 | 430,000 | 15.3 |
| | Geometric CV % | 13.1 | NC | 18.5 | 14.7 | 17.2 | 19.0 |
| | Min | 35,700 | 0.50 | 369,000 | 294,000 | 353,000 | 10.9 |
| | Median | 47,400 | 0.50 | 460,000 | 340,000 | 428,000 | 15.6 |
| | Max | 52,300 | 0.50 | 632,000 | 449,000 | 584,000 | 21.1 |

Abbreviations:
AUC(0-24), area under the plasma concentration-time curve (AUC) from time 0 to 24 hours post-dose;
AUC(0-48), AUC from time 0 to 48 hours post-dose;
AUClast, AUC from time zero to the time of the last measurable non-zero concentration;
Cmax, maximum observed concentration;
CV % = arithmetic percent coefficient of variation;
geometric CV %, geometric percent coefficient of variation;
max, maximum;
mean, arithmetic mean;
min, minimum;
N, sample size;
NC, not calculated;
SD, standard deviation
t$_{1/2}$, terminal phase half-life;
Tmax time of maximum observed concentration Overall, the most salient and consistent changes in qEEG band coherences were treatment-related increases in higher frequency bands from alpha to gamma 3 in the eyes-closed condition and high beta to gamma 3 in the eyes-open condition.

Changes in Other qEEG and ERP Endpoints. Significant changes in PARAFAC atom time scores confirmed this pattern. compound A was associated with increased ASSR high-frequency harmonic resonances, which was not evident in the placebo group. This is consistent with increased gamma-band amplitudes and may indicate facilitation of functional networks for perception and cognition. In addition, compound A reduced the peak latency of N100, P200, P300A (also reduced AUC) components in auditory oddball tasks, which was not evident in the placebo group. This may indicate increased attention, alertness, or sensory-perceptual processing speed.

Changes in EEG Endpoints as a Function of Compound A Concentration in Plasma. Changes in EEG endpoints as functions of plasma concentration measures for compound A were generally consistent, with post-dose changes in means for placebo vs. compound A treatment groups. The dominant pattern of qEEG effects indicated (1) decreasing post-dose values for delta and theta band amplitudes with increasing plasma levels of compound A, (2) increased plasma concentrations of compound A associated with post-dose increases of gamma band amplitude, with different time constants for the eyes-closed and eyes-open condition, and (3) decreases of the PARAFAC Delta atom mean time-scores with increasing plasma concentrations of compound A.

Conclusions:

Pharmacokinetics:

compound A was rapidly absorbed, as observed by individual $T_{max}$ values ranging from 0.5 to 1.0 hours across dosing Days 1 and 3.

There was negligible accumulation of compound A between Day 1 and Day 3, as geometric mean values of the exposure parameters were within 5% between days.

Geometric mean t½ values were slightly (~20%) higher on Day 3 than Day 1, although this could be an artifact of the longer sampling window after the Day 3 dose.

Variability of compound A key PK parameters was low (geometric CV<30%) across both dosing days.

Pharmacodynamics:

Compound A produced dose-dependent decreases in low-frequency EEG bands (delta, theta) and increases in high-frequency EEG bands (gamma). In alpha bands, there were decreases in amplitudes (or desynchronization) at 1 hour after dosing. These changes are all signs of EEG activation, and they did not occur in the placebo group.

Increased arousal, vigilance, and alertness are associated with "activated" EEG spectra, which are characterized by desynchronized alpha waves (low alpha amplitude) and absence of delta and theta waves, and which may also show increased high-frequency band amplitudes (higher beta and gamma bands).

EEG activation occurred within 1 hour of the first and second doses, as indicated by decreases from baselines in delta, theta, and alpha band amplitudes.

EEG activation was also evidenced by increases in beta-2, high beta and all gamma band amplitudes.

Activation is associated with increased alertness and arousal.

Increased beta-gamma band amplitudes may also indicate increased levels of perceptual or cognitive processing.

Compound A was associated with increased ASSR high-frequency resonance, which was not evident in the placebo group.

This is consistent with increased gamma-band amplitudes.

It may indicate facilitation of functional networks for perception and cognition.

Compound A reduced the peak latency of N100, P200, and P300A components in auditory oddball tasks, which was not evident in the placebo group.

This may indicate increased attention, alertness, or sensory-perceptual processing speed.

Changes in EEG endpoints as functions of plasma concentration measures for compound A were generally consistent, with post-dose changes in means for placebo vs. compound A treatment groups. The dominant pattern of qEEG effects indicated:

Decreasing post-dose values for delta and theta band amplitudes with increasing plasma levels of compound A.

Increased plasma concentrations of compound A associated with post-dose increases of gamma band amplitude, with different time constants for the eyes-closed and eyes-open condition.

Decreases of the PARAFAC Delta atom mean time-scores with increasing plasma concentrations of compound A.

Safety:

Two doses of compound A 2400 mg administered 48 hours apart were generally safe and well tolerated in healthy male subjects.

There were no deaths or other SAEs, discontinuations due to TEAEs, or moderate (Grade 2) or severe (Grade 3) TEAEs in the study.

All TEAEs reported in compound A-treated subjects were mild (Grade 1).

The incidence of TEAEs was higher in the placebo group (15.4%) than in the compound A group (8.3%), as was the incidence of drug-related TEAEs (15.4% for placebo vs. 0 for compound A). No dissociative effects were reported.

There were no clinically meaningful abnormalities in laboratory test results, vital signs, ECG data, safety EEG data, BPRS (+) or CADSS scores or neurological or physical examination findings. There was no evidence on safety EEGs of proconvulsant activity.

Example 4. Blinded Safety and Tolerability Multiple Ascending Dose (MAD) Study

Navitor Pharmaceuticals, Inc. (Navitor) is currently conducting a study to assess the safety, tolerability, and PK of multiple ascending doses of compound A (400 mg, 800 mg, 1600 mg, 2400 mg, and potentially 3000 mg) versus matched placebo in healthy volunteers. This study also includes an assessment of CSF and clinical biomarkers, as well as a cognition test.

The study is planned for 4 cohorts and 1 additional optional cohort. Up to approximately 40 healthy volunteers will be randomly assigned to double-blind treatment. In the initial 4 cohorts, eight (8) subjects will be randomized (3:1; compound A:placebo) in each of the four dosage-level cohorts (800 mg, 1600 mg, 2400 mg, and 400 mg) administered as an oral solution. Within each cohort, six subjects will be randomized to receive compound A and two subjects will be randomized to receive placebo. Each subject randomized will receive compound A or placebo once daily for 7 days. Subjects will dose in the morning and will dose each day at the same time. For cohort 3 (2400 mg), each subject will return to the unit after a minimum 5-day washout to receive an additional single dose of compound A or placebo under fed conditions in Period 2. Assessments of safety, tolerability, and PK as well as exploratory biomarker and clinical measures will occur.

If adequate safety and tolerability are observed in the first four cohorts, an optional 5$^{th}$ cohort evaluating up to 3000 mg dose may be conducted in order to characterize the safety, tolerability and PK of daily doses greater than 2400 mg. In this 5$^{th}$ cohort, one subject will receive compound A and one subject will receive placebo in a blinded manner. Provided no clinically significant safety or tolerability issues are noted after 24 hours of dosing for the initial two subjects, the other 6 subjects may be dosed. In this optional cohort, only safety, tolerability and PK will be assessed. Exploratory biomarker and clinical measures will not be assessed. The PK samples may be analyzed after specific cohorts, and PK data analyses may be performed in a blinded fashion to generate PK parameters.

The study will be monitored by a Safety Review Committee (SRC). The SRC is intended to ensure that treatment does not pose undue risk to subjects. Safety and tolerability will be assessed by the SRC prior to ascending from one dosage-level cohort to the next-higher dosage-level cohort. Additionally, the SRC could choose to modify the dosages or the dose escalation schedule in response to review of the available data.

Inclusion Criteria: Subjects who met the following criteria were considered eligible to participate in the clinical study:

All volunteers must satisfy the following criteria to be considered for study participation:
1. Subjects must understand the nature of the study and must provide signed and dated written informed consent before the conduct of any study-related procedures.
2. Subjects must be 18-65 years of age, inclusive.
3. Subjects must have a body mass index (BMI) between 18 and 35 kg/m$^2$, inclusive.
4. Female subjects must be post-menopausal or surgically sterile or must agree to use one or more of the following forms of contraception from the time of signing the informed consent form through at least 30 days following the last administration of study drug: hormonal (i.e., oral, transdermal/subdermal, implant, or injection); double barrier (i.e., condom, diaphragm with spermicide); intrauterine device (IUD); or vasectomized partner (6 months minimum). Postmenopausal women must have had ≥12 months of spontaneous amenorrhea with follicle-stimulating hormone (FSH) ≥30 mIU/mL. Surgically sterile women are defined as those who have had a hysterectomy, bilateral oophorectomy, or bilateral tubal ligation. All women must have a negative pregnancy test result before administration of study drug.
5. Male subjects who are biologically capable of having children (i.e., non-vasectomized) must agree to use one or more of the above forms of birth control for themselves and their partner(s), as appropriate, from the time of signing the informed consent form through at least 90 days following the last administration of study drug. They must also agree to abstain from sperm donation from the first administration of study drug to 90 days after the last administration of study drug.
6. Potential subjects must be, in the opinion of the Principal Investigator, able to participate in all scheduled evaluations, likely to complete all required tests, and likely to be compliant.

Exclusion Criteria: Subjects who met the following criteria were considered to be not eligible to participate in the clinical study:

Volunteers will be excluded from study participation for any of the following:
1. Prior or ongoing medical condition, medical history, physical or neurological findings, ECG, EEG, laboratory or vital signs abnormality that, in the Principal Investigator's opinion, could adversely affect the safety of the subject.
2. History (within the last year) or presence of suicidality with suicidal ideation (Type 4-5) as determined by the Columbia-Suicide Severity Rating Scale (C-SSRS) at screening or prior to dosing on Day 1
3. Alanine aminotransferase (ALT) or aspartate aminotransferase (AST) levels greater than 1.5 times the upper limit of normal (ULN) at screening or Day −1
4. Creatine kinase (CK) level greater than 1.5×ULN at screening or Day −1
5. Creatinine clearance <80 mL/min, according to the Cockcroft-Gault equation
6. White blood cell or absolute neutrophil counts that are clinically significantly below the normal range at screening or Day −1
7. A QT interval measurement corrected according to the Fridericia rule ($QT_cF$) >450 msec for males and >470 msec for females during controlled rest at screen or between screen and first dose administration (Day 1), or family history of long-QT syndrome.
8. PR (PQ) interval shortening <120 msec (PR<120 msec but >110 msec is acceptable if there is no evidence of ventricular pre-excitation).
9. PR (PQ) interval prolongation (>240 msec), intermittent second-degree (Wenckebach block while asleep or in deep rest is not exclusionary) or third-degree atrioventricular block.
10. Persistent or intermittent complete bundle branch block (BBB), or intraventricular conduction delay (IVCD) with QRS>110 msec.
11. A history of seizure, loss of consciousness for an unknown reason, or any other known neurological disorder placing the subject at risk for seizures.
12. A history of clinically significant head trauma, including closed head injury with loss of consciousness.
13. A history of clinically significant symptomatic orthostatic hypotension (i.e., postural syncope or dizziness).
14. A history of neuroleptic malignant syndrome.
15. A history of cancer within 5 years prior to screening or between screening and randomization (with the exception of non-metastatic basal and/or squamous cell carcinoma of the skin), any history of renal cell carcinoma or breast cancer, or a family history of lymphangioleiomyomatosis in association with tuberous sclerosis complex (TSC-LAM).
16. A diagnosis of intellectual disability (intellectual developmental disorder) or mental retardation.
17. History of alcohol use disorder within 6 months prior to screening, defined by an average weekly intake of >21 units for men and >14 units for women. One unit is equal to a half pint of beer, 1 serving of hard liquor or one glass of wine.
18. Regularly consumed (e.g., more days than not) excessive quantities of xanthine-containing beverages (e.g., more than five cups of coffee or the equivalent per day) within 30 days prior to screening or between screening and administration of first dose of the study drug (Day 1).

19. Donated blood or plasma within 3 months prior to screening or between screening and administration of first dose of the study drug (Day 1).
20. Used any experimental medication, device, or biologic within 3 months or five half-lives (whichever is longer) prior to administration of first dose of study drug (Day 1).
21. Strenuous physical activity (e.g., exercise, weight lifting, and moving furniture) within 1 week prior to administration of first dose of study drug (Day 1).
22. Unsatisfactory venous access.
23. Known or suspected hypersensitivity or idiosyncratic reaction to study drug or study drug excipients.
24. Known or suspected substance use disorder as determined by positive urine drug screen for drugs of abuse (including but not limited to *Cannabis*, cotinine, alcohol, and psychostimulants) at screening.
25. Used any prescription drug within 2 weeks, or five half-lives (whichever is longer), prior to screening, or between screening and administration of first dose of the study drug (Day 1).
26. Used any non-prescription drug (other than up to 3 g per day paracetamol/acetaminophen) within 2 weeks, or five half-lives (whichever is longer), prior to first dose administration (Day 1).
27. Used any vitamin, herbal supplement, or grapefruit or berries (juice/capsules) within 2 weeks prior to first dose administration (Day 1), unless approved by the Principal Investigator and medical monitor.
28. Used any tobacco-containing (e.g., cigar, cigarette, or snuff) or nicotine-containing product (e.g., nicotine chewing gum, nicotine plasters, or other product used for smoking cessation) within 3 months prior to screening, or between screening and administration of first dose of the study drug.
29. Prior participation in a clinical trial in which Compound A was administered For Subjects in Cohort 3:

30. Unable to consume the full FDA standard high-fat, high-calorie meal within 30 minutes prior to dose.

Cohort 1 (800 mg) and Cohort 2 (1600 mg) have been completed. In these cohorts, healthy volunteers were randomized to either compound A or placebo (6:2)

Cohort 1a consisted of 2 subjects
Cohort 1b consisted of 3 subjects
Cohort 1c consisted of 3 subjects
Cohort 2a consisted of 2 subjects
Cohort 2b consisted of 3 subjects
Cohort 2c consisted of 3 subjects Preliminary safety data from these cohorts were reviewed by a Safety Review Committee. No clinically significant abnormalities were observed on labs, vital signs or ECG. All AEs were mild. None were serious. No subject experienced an event that met the pre-specified protocol stopping criteria that are listed below:

Pre-Specified Stopping Criteria Review:

| Criteria number | Criteria |
| --- | --- |
| 1 | One or more subjects who receive compound A experiences a treatment-related serious adverse event (SAE). |
| 2 | One (1) subject who receives compound A experiences a seizure. |
| 3 | Two (2) or more subjects who receive compound A experience a psychotic reaction. |
| 4 | Two (2) or more subjects who receive compound A exhibit symptomatic orthostatic hypotension, with a >30 mmHg reduction in systolic BP or a value of <90 mmHg, or a >40 mmHg reduction to a systolic BP <100 mmHg. |
| 5 | Two (2) or more subjects who receive compound A exhibit a clinically significant ECG abnormality. |
| 6 | One or more or more subjects who receive compound A have QTc prolongation, as defined by an average absolute (regardless of baseline value) QTcF >500 msec or an increase of QTcF >60 msec above baseline value, confirmed (persistent for at least 5 minutes), and determined post-dose either during continuous 12-lead digital ECG (dECG) monitoring or on a repeat 12-lead ECG. |
| 7 | Two (2) or more subjects who receive compound A exhibit hypotension, as defined by a resting supine diastolic blood pressure <45 mmHg, an asymptomatic decrease in systolic blood ≥ pressure 20 mmHg to below 70 mmHg, persisting for at least 10 minutes on repeated assessment, or a symptomatic decrease in resting supine systolic blood pressure ≥20 mmHg. |
| 8 | Two (2) or more subjects who receive compound A exhibit hypertension, defined as an increase in resting systolic blood pressure >40 mmHg to above 180 mmHg, and persisting for at least 10 minutes, or an increase in resting diastolic blood pressure >20 mmHg to above 105 mmHg, persisting for at least 10 minutes |
| 9 | Two (2) or more subjects who receive compound A exhibit tachycardia, defined as resting supine heart rate >125 beats per minute, and persisting for at least 10 minutes. |
| 10 | Two (2) or more subjects who receive compound A exhibit symptomatic bradycardia, defined as heart rate <45 beats per minute, or asymptomatic bradycardia, defined as resting supine heart rate <30 beats per minute while awake, and persisting for at least 10 minutes |
| 11 | One (1) or more subjects who receive compound A fulfills Hy's law, defined as (AST or ALT ≥3 × upper limit of normal [ULN]) and (total Bilirubin ≥2 × ULN), in the absence of a significant increase in alkaline phosphatase (ALP) and in the absence of an alternative diagnosis that explains the increase in total bilirubin. |
| 12 | Two (2) or more subjects who receive compound A exhibit ALT, total bilirubin, or ALP >2 × ULN. |
| 13 | Two (2) or more subjects who receive compound A exhibit CK >3 × ULN. |
| 14 | Two (2) or more subjects who receive compound A exhibit renal toxicity, defined as serum Creatinine ≥1.5 × ULN. |
| 15 | Two (2) or more subjects who receive compound A exhibit hematologic toxicity, defined as one or more of the following in the absence of an alternative diagnosis that explains the hematologic abnormality:<br>Leukocyte count <2.5 × 109/L<br>Absolute neutrophil count <1.0 × 109/L<br>Platelet count <75 × 109/L |

As no subject met the stopping criteria, it was decided to proceed to assess an elevated dose of 2400 mg.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A method of treating treatment resistant depression in a patient in need thereof, comprising administering to the patient a therapeutically effective amount of a pharmaceutically acceptable composition comprising compound A:

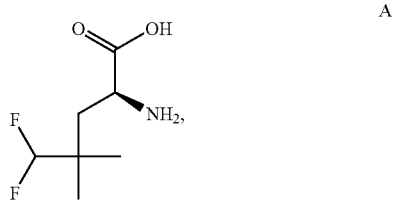

or a pharmaceutically acceptable salt thereof;
wherein the therapeutically effective amount comprises a total daily dose of about 100 mg to about 3000 mg; and
wherein the treatment resistant depression is resistant to one or more first line treatments.

2. The method according to claim 1, wherein the total daily dose is administered QD.

3. The method according to claim 1, comprising administering a single dose.

4. The method according to claim 1, comprising administering at least two doses.

5. The method according to claim 1, comprising administering compound A daily for at least two, three, four, five, six, or seven consecutive days.

6. The method according to claim 4, comprising administering a first dose about 48 hours prior to administering a second dose.

7. The method according to claim 1, wherein the total daily dose is administered under fasted conditions.

8. The method according to claim 1, wherein the total daily dose is administered under fed conditions.

9. The method according to claim 1, wherein the treatment resistant depression is resistant to second line treatments.

10. The method according to claim 1, wherein the patient is diagnosed with major depressive disorder ("MDD").

11. The method according to claim 1, wherein the patient is experiencing a depressive episode and has had at least one inadequate response to at least one antidepressant during the depressive episode.

12. The method according to claim 11, wherein the patient is experiencing a depressive episode and has had at least one inadequate response to at least two, three, or four different antidepressants during the depressive episode.

13. The method according to claim 1, wherein the patient is assessed to have a Montgomery-Asberg Depression Rating Scale (MADRS) total score of ≥21 prior to treatment.

14. The method according to claim 1, wherein the patient is assessed to have a Raskin Depression Rating Scale score of ≥9 prior to treatment.

15. The method according to claim 1, wherein administration is oral.

16. The method according to claim 1, wherein the total daily dose is a single unit dosage form.

17. The method according to claim 1, wherein the total daily dose comprises a liquid unit dosage form comprising about 150 mg, about 300 mg, about 400 mg, about 600 mg, about 800 mg, about 1000 mg, about 1600 mg, about 2400 mg, or about 3000 mg of compound A, or pharmaceutically acceptable salt thereof.

18. The method according to claim 17, wherein the total daily dose comprises a liquid unit dosage form comprising about 2400 mg of compound A, or pharmaceutically acceptable salt thereof.

* * * * *